United States Patent
Winderickx et al.

(10) Patent No.: US 9,447,179 B2
(45) Date of Patent: Sep. 20, 2016

(54) ANTIBODIES TO PHOSPHORYLATED TAU AGGREGATES

(75) Inventors: Joris Winderickx, Wilsele (BE); Eugeen Vanmechelen, Nazareth-Eke (BE); Fred Van Leuven, Lubbeek (BE)

(73) Assignees: KATHOLIEKE UNIVERSITEIT LEUVEN, KU RESEARCH & DEVELOPMENT, Leuven (BE); FUJIREBIO EUROPE N.V., Ghent (BE)

( * ) Notice: Subject to any disclaimer, the term of this patent is extended or adjusted under 35 U.S.C. 154(b) by 0 days.

(21) Appl. No.: 14/232,659

(22) PCT Filed: Jul. 16, 2012

(86) PCT No.: PCT/EP2012/063924
§ 371 (c)(1),
(2), (4) Date: Jan. 14, 2014

(87) PCT Pub. No.: WO2013/007839
PCT Pub. Date: Jan. 17, 2013

(65) Prior Publication Data
US 2014/0161875 A1 Jun. 12, 2014

(30) Foreign Application Priority Data
Jul. 14, 2011 (GB) .................................. 1112056.5

(51) Int. Cl.
*C07K 16/18* (2006.01)
*A61K 47/48* (2006.01)
(Continued)

(52) U.S. Cl.
CPC ......... *C07K 16/18* (2013.01); *A61K 47/48246* (2013.01); *A61K 47/48823* (2013.01);
(Continued)

(58) Field of Classification Search
None
See application file for complete search history.

(56) References Cited

U.S. PATENT DOCUMENTS

| 2004/0110938 A1* | 6/2004 | Parekh | C07K 14/705 536/23.5 |
| 2008/0050383 A1* | 2/2008 | Sigurdsson | A61K 9/0019 424/141.1 |

(Continued)

FOREIGN PATENT DOCUMENTS

| EP | 2243830 | * 10/2010 | ............. C12N 15/09 |
| WO | 2005080986 A1 | 9/2005 | |

(Continued)

OTHER PUBLICATIONS

Heng 2005 "making cell-permeable antibodies (transbody) through fusion of protein transduction domains (PTD) with single chain variable fragment (scFv) antibodies: potential advantages over antibodies expressed within the intracellular environment (intrabody)" Medical hypotheses 64:1105-1108.*

(Continued)

*Primary Examiner* — Adam M Weidner
(74) *Attorney, Agent, or Firm* — Amster, Rothstein & Ebenstein LLP

(57) ABSTRACT

This invention concerns affinity tools for oligomeric forms of tau protein. It relates to the field of neurodegeneration, more particularly to the field of tau-related diseases and tauopathy. The invention provides novel tau antibodies and antibody fragments, nucleic acids encoding such antibodies and antibody fragments, cell lines producing such antibodies and antibody fragments, antibody compositions, and kits for the detection of aggregated tau and for the diagnosis of diseases involving aggregated tau. The invention further provides methods for the detection of aggregated tau, for the diagnosis of diseases involving aggregated tau, and for the identification of compositions interfering with the formation and/or stability of tau aggregates.

1 Claim, 11 Drawing Sheets

Figure 1:
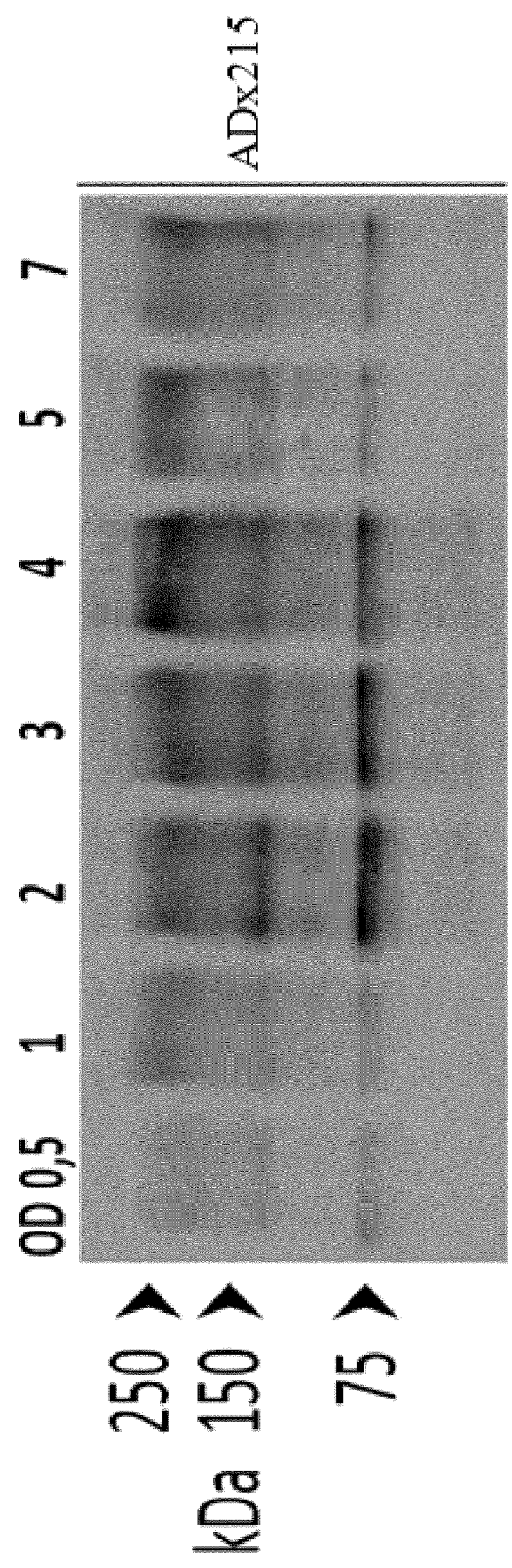

| | | | YT1.15 (10 µg/ml) | |
|---|---|---|---|---|
| aa | Aa | | Rampo 1/1000 | |
| 1 | 15 | MAEPRQEFEVMEDHA | 36 | SEQ. ID. No. 31 |
| 2 | 16 | AEPRQEFEVMEDHAG | 31 | SEQ. ID. No. 32 |
| 3 | 17 | EPRQEFEVMEDHAGT | 47 | SEQ. ID. No. 33 |
| 4 | 18 | PRQEFEVMEDHAGTY | 52 | SEQ. ID. No. 34 |
| 5 | 19 | RQEFEVMEDHAGTYG | 42 | SEQ. ID. No. 35 |
| 6 | 20 | QEFEVMEDHAGTYGL | 50 | SEQ. ID. No. 36 |
| 7 | 21 | EFEVMEDHAGTYGLG | 97 | SEQ. ID. No. 37 |
| 8 | 22 | FEVMEDHAGTYGLGD | 141 | SEQ. ID. No. 38 |
| 9 | 23 | EVMEDHAGTYGLGDR | 911 | SEQ. ID. No. 39 |
| 10 | 24 | VMEDHAGTYGLGDRK | 2055 | SEQ. ID. No. 40 |
| 11 | 25 | MEDHAGTYGLGDRKD | 2161 | SEQ. ID. No. 41 |
| 12 | 26 | EDHAGTYGLGDRKDQ | 2100 | SEQ. ID. No. 42 |
| 13 | 27 | DHAGTYGLGDRKDQG | 2082 | SEQ. ID. No. 43 |
| 14 | 28 | HAGTYGLGDRKDQGG | 2387 | SEQ. ID. No. 44 |
| 15 | 29 | AGTYGLGDRKDQGGY | 2434 | SEQ. ID. No. 45 |
| 16 | 30 | GTYGLGDRKDQGGYT | 2229 | SEQ. ID. No. 46 |
| 17 | 31 | TYGLGDRKDQGGYTM | 1364 | SEQ. ID. No. 47 |
| 18 | 32 | YGLGDRKDQGGYTMH | 171 | SEQ. ID. No. 48 |
| 19 | 33 | GLGDRKDQGGYTMHQ | 60 | SEQ. ID. No. 49 |
| 20 | 34 | LGDRKDQGGYTMHQD | 49 | SEQ. ID. No. 50 |
| 21 | 35 | GDRKDQGGYTMHQDQ | 49 | SEQ. ID. No. 51 |

(51) Int. Cl.
*C07K 14/47* (2006.01)
*G01N 33/566* (2006.01)

(52) U.S. Cl.
CPC ......... *C07K14/4711* (2013.01); *G01N 33/566* (2013.01); *C07K 2317/56* (2013.01); *C07K 2317/565* (2013.01)

(56) References Cited

U.S. PATENT DOCUMENTS

| | | | | |
|---|---|---|---|---|
| 2009/0104121 | A1* | 4/2009 | Madasamy | 424/9.2 |
| 2009/0155249 | A1 | 6/2009 | Pfeifer et al. | |
| 2010/0316564 | A1* | 12/2010 | Sigurdsson | 424/1.49 |
| 2011/0059093 | A1* | 3/2011 | Bohrmann | C07K 14/4711 424/139.1 |
| 2012/0276009 | A1 | 11/2012 | Pfeifer et al. | |

FOREIGN PATENT DOCUMENTS

| | | |
|---|---|---|
| WO | 2008070229 A2 | 6/2008 |
| WO | 2008156622 A1 | 12/2008 |
| WO | 2012045882 A2 | 4/2012 |

OTHER PUBLICATIONS

Horowitz 2004 "early n-terminal changes and caspase-6 cleavage of tau in alzheimer's disease" J Neurosci 24(36):7895-7902.*
Kussie 1994 "a single engineered amino acid substitution changes antibody fine specificity" J immunology p. 146-152.*
Rafii 2009 "recent developments in alzheimer's disease therapeutics" BMC medicine 7:7.*
Sadowsky 2014 "Diagnosis of alzheiemr's disease through the eye and its correlation with cognitive tests and brain imaging" JSM Alz Dis Related dementia 1(2):1008.*
Signet 2015 "tau (tau 12) monoclonal antibody: data sheet" accessed from eurogentec.com on Sep. 8, 2015.*
Voss 2014 "modulation of tau phosphorylation by environmental copper" translational neurodegeneration 3:24.*
International Preliminary Report on Patentability, dated Jan. 23, 2014 in connection with PCT International Patent Application No. PCT/EP2012/063924,8 pages.
International Preliminary Report on Patentability, dated Jan. 23, 2014 in connection with PCT International Patent Application No. PCT/EP2012/063676,10 pages.
Asuni A A et al., entitled "Immunotherapy targeting pathological tau conformers in a tangle mouse model reduces brain pathology with associated functional improvements," Journal of Neuroscience, vol. 27, No. 34, Aug. 1, 2007. 9115-9129.
Jicha G A et al., entitled "Sequence requirements for formation of conformational variants of tau similar to those found in Alzheimer's disease," Journal of Neuroscience Research, vol. 55, Mar. 15, 1999, 713-123.
Vanhelmont T et al., entitled "Serine-409 phosphorylation and oxidative damage define aggregation of human protein tau in yeast," FEMS Yeast Research, vol. 10, No. 8, Dec. 1, 2010, 992-1005.
Vanderbroek T et al., entitled "Identification and isolation of a Hyperphosphorylated, Conformationally Changed Intermediate of Human Protein Tau Expressed in Yeast," Biochemistry, vol. 44, No. 34, Aug. 2005, 11466-11475.
Decraemer H et al., entitled "Stable Tau and Phospho-Tau Levels in Plasma Normal Individuals," 9th International Conference—AD/PD 2009, Abstract, 1 page. Mar. 13, 2009 Conference, "Oral Presentations: Neuroimaging & Biomarkers," 1 page. ADPD Mar. 13, 2009 presentation entitled "Total tau and phospho-tau levels in plasma," 23 pages.
Brande J V et al., entitled "Measuring Oligomerisation of Tau Heterologously Expressed om Yeast Models for Tauopathies," ADPD 2011—Session Planner, 1 page. Mar. 11, 2011 & Mar. 12, 2011 Poster Session 2:(contd) Other Tauopathies, 1 page.
PCT International Search Report, dated Nov. 20, 2012 in connection with PCT International Patent Application No. PCT/EP2012/63924, 5 pages.
Office Action issued May 11, 2016 in corresponding Japanese Patent Application No. 2014-51981, 7 pages.

* cited by examiner

| | ADx215 coating (5µg/ml) | | | |
|---|---|---|---|---|
| pho85d yeast tau (ng/ml) | ADx210-bio (200ng/ml) | | ADx201-bio (200ng/ml) | |
| 5000 | 0,197 | 0,183 | 2,734 | 2,744 |
| 1000 | 0,203 | 0,196 | 2,920 | 3,056 |
| 200 | 0,207 | 0,207 | 3,558 | 3,308 |
| 40 | 0,201 | 0,200 | 0,913 | 0,854 |
| 8 | 0,203 | 0,200 | 0,226 | 0,200 |
| 1,6 | 0,205 | 0,208 | 0,193 | 0,170 |
| 0,32 | 0,207 | 0,202 | 0,192 | 0,163 |
| 0 | 0,192 | 0,196 | 0,181 | 0,169 |

| | | | | |
|---|---|---|---|---|
| WT e.v. ("5µg/ml") | 0,167 | 0,172 | 0,160 | 0,147 |
| rPeptide441 (1µg/ml) | 3,598 | 3,617 | 2,768 | 2,239 |

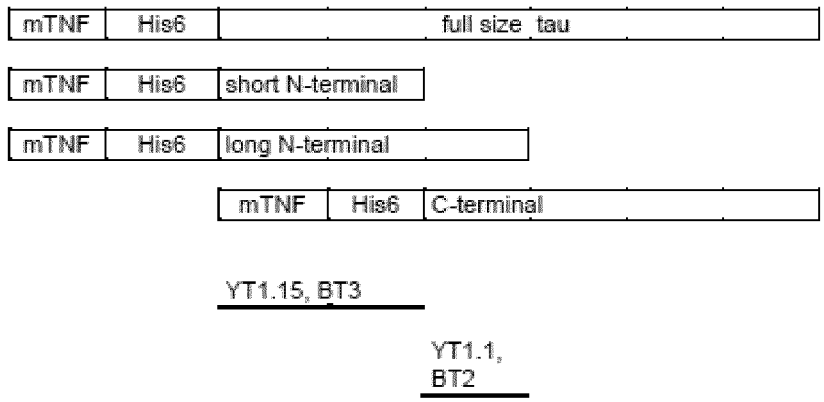

Fig. 5A

| aa | Aa | | YT1.15 (10 µg/ml) Rampo 1/1000 | |
|---|---|---|---|---|
| 1 | 15 | MAEPRQEFEVMEDHA | 36 | SEQ. ID. No. 31 |
| 2 | 16 | AEPRQEFEVMEDHAG | 31 | SEQ. ID. No. 32 |
| 3 | 17 | EPRQEFEVMEDHAGT | 47 | SEQ. ID. No. 33 |
| 4 | 18 | PRQEFEVMEDHAGTY | 52 | SEQ. ID. No. 34 |
| 5 | 19 | RQEFEVMEDHAGTYG | 42 | SEQ. ID. No. 35 |
| 6 | 20 | QEFEVMEDHAGTYGL | 50 | SEQ. ID. No. 36 |
| 7 | 21 | EFEVMEDHAGTYGLG | 97 | SEQ. ID. No. 37 |
| 8 | 22 | FEVMEDHAGTYGLGD | 141 | SEQ. ID. No. 38 |
| 9 | 23 | EVMEDHAGTYGLGDR | 911 | SEQ. ID. No. 39 |
| 10 | 24 | VMEDHAGTYGLGDRK | 2055 | SEQ. ID. No. 40 |
| 11 | 25 | MEDHAGTYGLGDRKD | 2161 | SEQ. ID. No. 41 |
| 12 | 26 | EDHAGTYGLGDRKDQ | 2100 | SEQ. ID. No. 42 |
| 13 | 27 | DHAGTYGLGDRKDQG | 2082 | SEQ. ID. No. 43 |
| 14 | 28 | HAGTYGLGDRKDQGG | 2387 | SEQ. ID. No. 44 |
| 15 | 29 | AGTYGLGDRKDQGGY | 2434 | SEQ. ID. No. 45 |
| 16 | 30 | GTYGLGDRKDQGGYT | 2229 | SEQ. ID. No. 46 |
| 17 | 31 | TYGLGDRKDQGGYTM | 1364 | SEQ. ID. No. 47 |
| 18 | 32 | YGLGDRKDQGGYTMH | 171 | SEQ. ID. No. 48 |
| 19 | 33 | GLGDRKDQGGYTMHQ | 60 | SEQ. ID. No. 49 |
| 20 | 34 | LGDRKDQGGYTMHQD | 49 | SEQ. ID. No. 50 |
| 21 | 35 | GDRKDQGGYTMHQDQ | 49 | SEQ. ID. No. 51 |

Fig. 5B

Fig. 6

Sequence ID 1 organism="Homo sapiens" /db_xref="taxon:9606" /chromosome="17" /map="17q21.1"

Protein        1..758

```
  1 maeprqefev medhagtygl gdrkdqggyt mhqdqegdtd aglkesplqt ptedgseepg
 61 setsdakstp taedvtaplv degapgkqaa aqphteipeg ttaeeagigd tpsledeaag
121 hvtqepesgk vvqegflrep gppglshqlm sgmpgapllp egpreatrqp sgtgpedteg
181 grhapellkh qllgdlhqeg pplkgaggke rpgskeevde drdvdesspq dsppskaspa
241 qdgrppqtaa reatsipgfp aegaiplpvd flskvsteip asepdgpsvg rakgqdaple
301 ftfhveitpn vqkeqahsee hlgraafpga pgegpeargp slgedtkead lpepsekqpa
361 aaprgkpvsr vpqlkarmvs kskdgtgsdd kkaktstrss aktlknrpcl spkhptpgss
421 dpliqpsspa vcpeppsspk yvssvtsrtg ssgakemklk gadgktkiat prgaappgqk
481 gqanatripa ktppapktpp ssgeppksgd rsgysspgsp gtpgsrsrtp slptpptrep
541 kkvavvrtpp kspssaksrl qtapvpmpdl knvkskigst enlkhqpggg kvqiinkkld
601 lsnvqskcgs kdnikhvpgg gsvqivykpv dlskvtskcg slgnihhkpg ggqvevksek
661 ldfkdrvqsk igsldnithv pgggnkkiet hkltfrenak aktdhgaeiv ykspvvsgdt
721 sprhlsnvss tgsidmvdsp qlatladevs aslakqgl
```

Sequence ID 2 organism="Homo sapiens" /db_xref="taxon:9606" /chromosome="17" /map="17q21.1" /

Protein        1..441

```
  1 maeprqefev medhagtygl gdrkdqggyt mhqdqegdtd aglkesplqt ptedgseepg
 61 setsdakstp taedvtaplv degapgkqaa aqphteipeg ttaeeagigd tpsledeaag
121 hvtqarmvsk skdgtgsddk kakgadgktk iatprgaapp gqkgqanatr ipaktppapk
181 tppssgeppk sgdrsgyssp gspgtpgsrs rtpslptppt repkkvavvr tppkspssak
241 srlqtapvpm pdlknvkski gstenlkhqp gggkvqiink kldlsnvqsk cgskdnikhv
301 pgggsvqivy kpvdlskvts kcgslgnihh kpgggqvevk sekldfkdrv qskigsldni
361 thvpgggnkk iethkltfre nakaktdhga eivykspvvs gdtsprhlsn vsstgsidmv
421 dspqlatlad evsaslakqg l
```

Fig. 6 (continuation)

Sequence ID 3

/organism="Homo sapiens" / db_xref="taxon:9606" / chromosome="17" /map="17q21.1" /
Protein     1..383

1 maeprqefev medhagtygl gdrkdqggyt mhqdqegdtd aglkaeeagi gdtpsledea
  61 aghvtqarmv skskdgtgsd dkkakgadgk tkiatprgaa ppgqkgqana tripaktppa
 121 pktppssgep pksgdrsgys spgspgtpgs rsrtpslptp ptrepkkvav vrtppkspss
 181 aksrlqtapv pmpdlknvks kigstenlkh qpgggkvqii nkkldlsnvq skcgskdnik
 241 hvpgggsvqi vykpvdlskv tskcgslgni hhkpgggqve vksekldfkd rvqskigsld
 301 nithvpgggn kkiethkltf renakaktdh gaeivykspv vsgdtsprhl snvsstgsid
 361 mvdspqlatl adevsaslak qgl

Sequence ID 4 organism="Homo sapiens" /db_xref="taxon:9606" /chromosome="17" /map="17q21.1" /
Protein     1..352

1 maeprqefev medhagtygl gdrkdqggyt mhqdqegdtd aglkaeeagi gdtpsledea
  61 aghvtqarmv skskdgtgsd dkkakgadgk tkiatprgaa ppgqkgqana tripaktppa
 121 pktppssgep pksgdrsgys spgspgtpgs rsrtpslptp ptrepkkvav vrtppkspss
 181 aksrlqtapv pmpdlknvks kigstenlkh qpgggkvqiv ykpvdlskvt skcgslgnih
 241 hkpgggqvev ksekldfkdr vqskigsldn ithvpgggnk kiethkltfr enakaktdhg
 301 aeivykspvv sgdtsprhls nvsstgsidm vdspqlatla devsaslakq gl

Sequence ID 5 organism="Homo sapiens" /db_xref="taxon:9606" /chromosome="17" /map="17q21.1"
Protein     1..412

1 maeprqefev medhagtygl gdrkdqggyt mhqdqegdtd aglkesplqt ptedgseepg
  61 setsdakstp taeaeeagig dtpsledeaa ghvtqarmvs kskdgtgsdd kkakgadgkt
 121 kiatprgaap pgqkgqanat ripaktppap ktppssgepp ksgdrsgyss pgspgtpgsr
 181 srtpslptpp trepkkvavv rtppkspssa ksrlqtapvp mpdlknvksk igstenlkhq
 241 pgggkvqiin kkldlsnvqs kcgskdnikh vpgggsvqiv ykpvdlskvt skcgslgnih
 301 hkpgggqvev ksekldfkdr vqskigsldn ithvpgggnk kiethkltfr enakaktdhg
 361 aeivykspvv sgdtsprhls nvsstgsidm vdspqlatla devsaslakq gl

Fig. 6 (continuation)

Sequence ID 6 organism="Homo sapiens" /db_xref="taxon:9606" /chromosome="17" /map="17q21.1"

Protein        1..776

1 maeprqefev medhagtygl gdrkdqggyt mhqdqegdtd aglkesplqt ptedgseepg
     61 setsdakstp taedvtaplv degapgkqaa aqphteipeg ttaeeagigd tpsledeaag
    121 hvtqepesgk vvqegflrep gppglshqlm sgmpgapllp egpreatrqp sgtgpedteg
    181 grhapellkh qllgdlhqeg pplkgaggke rpgskeevde drdvdesspq dsppskaspa
    241 qdgrppqtaa reatsipgfp aegaiplpvd flskvsteip asepdgpsvg rakgqdaple
    301 ftfhveitpn vqkeqahsee hlgraafpga pgegpeargp slgedtkead lpepsekqpa
    361 aaprgkpvsr vpqlkarmvs kskdgtgsdd kkaktstrss aktlknrpcl spkhptpgss
    421 dpliqpsspa vcpeppsspk yvssvtsrtg ssgakemklk gadgktkiat prgaappgqk
    481 gqanatripa ktppapktpp ssatkqvqrr pppagprser geppksgdrs gysspgspgt
    541 pgsrsrtpsl ptpptrepkk vavvrtppks pssaksrlqt apvpmpdlkn vkskigsten
    601 lkhqpggkv qiinkkldls nvqskcgskd nikhvpgggs vqivykpvdl skvtskcgsl
    661 gnihhkpggg qvevksekld fkdrvqskig sldnithvpg ggnkkiethk ltfrenakak
    721 tdhgaeivyk spvvsgdtsp rhlsnvsstg sidmvdspql atladevsas lakqgl

Sequence ID 7

/organism="Homo sapiens" /db_xref="taxon:9606" /chromosome="17"
/map="17q21.1"

Protein        1...381

1 maeprqefev medhagtygl gdrkdqggyt mhqdqegdtd aglkesplqt ptedgseepg
     61 setsdakstp taeaeeagig dtpsledeaa ghvtqarmvs kskdgtgsdd kkakgadgkt
    121 kiatprgaap pgqkgqanat ripaktppap ktppssgepp ksgdrsgyss pgspgtpgsr
    181 srtpslptpp trepkkvavv rtppkspssa ksrlqtapvp mpdlknvksk igstenlkhq
    241 pgggkvqivy kpvdlskvts kcgslgnihh kpgggqvevk sekldfkdrv qskigsldni
    301 thvpgggnkk iethkltfre nakaktdhga eivykspvvs gdtsprhlsn vsstgsidmv
    361 dspqlatlad evsaslakqg l

Sequence ID 8 organism="Homo sapiens" /db_xref="taxon:9606" /chromosome="17" /map="17q21.1"

Protein        1           410

Fig. 6 (continuation)

```
  1 maeprqefev medhagtygl gdrkdqggyt mhqdqegdtd aglkesplqt ptedgseepg
 61 setsdakstp taedvtaplv degapgkqaa aqphteipeg ttaeeagigd tpsledeaag
121 hvtqarmvsk skdgtgsddk kakgadgktk iatprgaapp gqkgqanatr ipaktppapk
181 tppssgeppk sgdrsgyssp gspgtpgsrs rtpslptppt repkkvavvr tppkspssak
241 srlqtapvpm pdlknvkski gstenlkhqp gggkvqivyk pvdlskvtsk cgslgnihhk
301 pgggqvevks ekldfkdrvq skigsldnit hvpgggnkki ethkltfren akaktdhgae
361 ivykspvvsg dtsprhlsnv sstgsidmvd spqlatlade vsaslakqgl
```

Seq ID's 9 – 14 on CDR's ICCGn°7301

Amino acid sequence of ADx210 CDR's of the light chain variable region (L1/L2/L3)

SEQ ID NO: 9 RSSESIVHSSGKTYLE

SEQ ID NO: 10 EVSNRFS

SEQ ID NO: 11 FQGSHVPWT

Amino acid sequence of ADx210 CDR's of the heavy chain variable region (H1/H2/H3)

SEQ ID NO: 12 GFTFSNFGMH

SEQ ID NO: 13 YITSGSSSIYYADTVKG

SEQ ID NO: 14 SVPYGYGLFDY

Sequence ID 15 : Amino acid sequence of the Heavy chain variable region of ADx210 (ICCGn°7301).

VQLQESGGGLVQPGGSRKLSCAASGFTFSNFGMHWVRQAPDKGLEWVAYITSG SSSIYYADTVKGRFTISRDNPKNTLFLQMTSLRSEDTAMYYCARSVPYGYGLFDYWGR GTTLTVSSAKTTPPSVYPLAPGSAAQT

Bold concerns the H1,H2 & H3

Sequence ID 17 : Amino acid sequence of a subpart of the Heavy chain variable region of ADx210 (ICCGn°7301).

Fig. 6 (continuation)

VQLQESGGGLVQPGGSRKLSCAASGFTFSNFGMHWVRQAPDKGLEWVAYIT SGSSSIYYADTVKGRFTISRDNPKNTLFLQMTSLRSEDTAMYYCARSVPYGYGLFDYW GRGTTLTVSSAKTTPPSVYPLAP

Bold concerns the H1,H2 & H3

Sequence ID 16 Amino acid sequence of the Light chain variable region of ADx210 (ICCGn°7301).

LPVRLLVLMSWIPASSSDVLMTQIPVSLSVSLGDQASISCRSSESIVHSSGKTYLEW YLQKPGQSPKLLIYEVSNRFSGVPDRFSGSGSGTDFTLKISR VEAEDLGVYYCFQGSHVPWTFGGGTKLEIKR

Bold concerns the L1,L2 & L3

Sequence ID 18 : Amino acid sequence of the Light chain variable region of an isoform of ADx210 (ICCGn°7301).

KLPVRLLVLMSWIPASSSDVLMTQIPVSLSVSLGDQASISCRSSESIVHSSGKTYLE WYLQKPGQSPKLLIYEVSNRFSGVPDRFSGSGSGTDFTLKISR VEAEDLGVYYCFQGSHVPWTFGGGTKLEIKR

Bold concerns the L1,L2 & L3

Amino acid sequence of ADx215 CDR's of the heavy chain variable region (H1/HL2/H3)

Sequence ID 19 : GFNFRSYGMS
Sequence ID 20 : TISSGGNYTYYPDSVKG
Sequence ID 21: SFYGAFDY

Amino acid sequence of ADx215 CDR's of the light chain variable region (L1/L2/L3)

Sequence ID 22: RSSQNILHSNGNTYLE
Sequence ID 23: KVSSRFS
Sequence ID 24: FQGSLVPWT Sequence ID 25: Amino acid sequence of ADx215 Heavy chain variable region

Fig. 6 (continuation)

DFGLSWVFLALILKGIQCEVQLVESGGDLVKPGGSLKLSCAASGFNFRSYGMSWV
RQTPDKRLEWVATISSGGNYTYYPDSVKGRFTISRDNAKNILYLQMSSLNSEDTALYY
CTYSFYGAFDYWGQGTTLTVSSAKTTPPSVYPLAPGSAAQTNSMVTLGCLVKGYFPEP
VTVTWNSGSLS

Sequence ID 26: Amino acid sequence of ADx215 Light chain variable region

KLPVRLLVLMFWIPASSSDVLMTQTPLSLPVSLGDQASISCRSSQNILHSNGNTYL
EWYLQKPGQSPKLLIYKVSSRFSGVPDRFSGSGSGTDFTLKITRVEAEDLGVYYCFQGS
LVPWTFGGGTKLEIRRADAAPTVSIFPPSSEQL

Tau epitope recognized by ADx215

Sequence ID 27: GTYGLGDRK

Sequence ID 28: EFEVMEDHA

Sequence ID 29: EFEVMEDHAGTYGLGDRK

ANTIBODIES TO PHOSPHORYLATED TAU AGGREGATES

CROSS-REFERENCE TO RELATED APPLICATIONS

This application is a U.S. national stage entry under 35 U.S.C. §371 of PCT International Patent Application No. PCT/EP2012/63924, filed Jul. 16, 2012, which claims priority to Great Britain Patent Application No. 1112056.5, filed Jul. 14, 2011, the contents of which are incorporated herein by reference in their entirety.

FIELD OF THE INVENTION

This invention concerns affinity tools for oligomeric forms of tau protein. It relates to the field of neurodegeneration, more particularly to the field of tau-related diseases and tauopathies. The invention provides novel tau antibodies and antibody fragments, nucleic acids encoding such antibodies and antibody fragments, cell lines producing such antibodies and antibody fragments, antibody compositions, and kits for the detection of aggregated tau and for the diagnosis of in diseases involving aggregated tau. The invention further provides methods for the detection of aggregated tau, for the diagnosis of diseases involving aggregated tau, and for the identification of compositions interfering with the formation and/or stability of tau aggregates.

BACKGROUND OF THE INVENTION

Alzheimer's dementia (AD) is the most prevalent neurodegenerative disorder, affecting about 2-5% of the population by the age of 65 years and more than 35% by the age of 85. The disease comprises more than 75% of all dementia cases. Worldwide there are an estimated 18 million AD patients and this number is expected to double in the next 20 years. Besides therapy, early and objective diagnosis remains the major clinical problem. Diagnosis of AD is only definite and certain by post-mortem pathological analysis of the brain for the presence of extracellular deposits of beta-amyloid (Aβ) peptides, known as amyloid plaques, and intracellular aggregates of hyperphosphorylated protein tau in the form of paired helical filaments (PHF) and neurofibrillary tangles (NFT). Based on clinical examination and on cognition tests, the diagnosis evolves from mild-cognitive impairment (MCI) to possible AD and probable AD. In the late stages, trained clinicians can only diagnose AD with 80-85% certainty, leaving a high number of false positive and false negative cases. Hence, there is an urgent need for early and accurate diagnosis as this would allow for proper and effective treatment. Such treatment is not yet available, in part due to the fact that experimental drugs must be tested in early stage of AD before the brain suffers from irreversible damage (Tarditi et al., 2009). Diagnosis based on the imaging of brain, such as MRI or PET, has improved enormously during the last decade but, nonetheless, also these diagnostic systems are only accurate at the later phases of AD and therefore are not useful for the recognition of early stage AD cases (van Berckel and Scheltens, 2007). Therefore, enormous efforts are put in searching for biomarkers that could allow for an objective differentiating measurement in body fluids such as blood plasma or cerebrospinal fluid (CSF).

For the latter, Innogenetics NV (INNX) provides diagnostic kits for clinical practice based on measurement of total tau protein, phosphorylated tau protein, and the amyloid peptide Aβ42 in the form of ELISA-kits INNOTEST® hTau, INNOTEST® phospho-Tau (P-Thr181) and INNOTEST® β-amyloid(1-42), respectively, as well as the multi-parametric immunotest INNO-BIA AlzBio3. These kits give satisfactory results when it comes to discriminate AD patients from healthy persons based on CSF measurements, with an accuracy up to 83%. However, they fall short when it comes to discriminate AD, especially early stage, from other types of dementia or to measure the biomarkers in plasma samples.

To date, there are no effective therapeutic drugs available for AD and the current treatment is limited to the administration of drugs that temporarily suppress the symptoms, such as the cholinesterase inhibitor Reminyl® or the NMDA antagonist Memantine®. For therapeutic intervention, research of the last decades placed a major focus on the prevention or clearance of Aβ deposits. However, more and more data are indicating that this may not be the best approach. Not only is there a poor correlation between Aβ plaque pathology and the clinical progression of AD, but several reports demonstrated the lack of a significant clinical benefit upon immunological clearance of Aβ deposits in the brain of transgenic (Tg) mice and AD patients (Weiner and Frenkel, 2006; Josephs et al., 2008; Tarawneh and Holtzman, 2009). In contrast, the accumulation of paired helical filaments (PHF or PHFtau) and neurofibrillary tangles (NFTs) in the AD brain is highly correlated with disease progression and it is commonly used to stage AD by post-mortem histopathology (Braak and Braak, 1991). Furthermore, the suppression of protein tau in Tg mice models, either genetically or by means of immunological interference, led to reduction of the brain pathology and functional improvement (Santacruz et al., 2005; Oddo et al., 2006; Asuni et al., 2007; Sigurdsson, 2008). Hence, it appears that protein tau might be a good target for therapeutic intervention, either alone or in combination with clearance of toxic Aβ peptides. Unfortunately, there is only limited knowledge about the pathways and molecular mechanisms that drive protein tau to form PHF and NFT, neither is there a profound insight in the structure of the actual toxic tau agent(s), which could be conformer(s), oligomers, paired helical filaments (PHF) and neurofibrillary tangles (NFT).

In contrast to small proteins such as prion, synuclein and peptides such as Aβ where relatively few post-translational modifications and pathological mutations are associated with disease and oligomerization, the microtubule-associated protein tau is a challenge. Many different post-translational modifications, alternative splicing and many different mutations define a wide range of disease associations ranging from Parkinson's disease over frontotemporal lobe dementia to Alzheimer's disease. To study the biochemistry and pathogenicity of protein tau, several model systems have been developed, which include flies and worms as well as cell lines, besides Tg mice.

Yeast is a well-characterized simple system in which the cellular biology is well-described in molecular terms and which can be used to express, purify and characterize specific molecular forms of specific proteins in a timely manner. Recently, so-called humanized yeast models were developed that recapitulated important aspects of a tauopathy. These yeast models displayed tau (hyper)phosphorylation, tau conformational changes and tau self-aggregation. Importantly, creation of the major pathogenic phospho-epitopes on human tau, such as the AD2 (P-Ser396/P-Ser404) and the PG5 (P-Ser409) epitopes, were found to be modulated by Mds1 and Pho85, the yeast orthologues of the two most important mammalian tau kinases, i.e. glycogen synthase kinase 3β (GSK-3β) and cyclin-dependent kinase 5 (cdk5), respectively. Negative and positive modulation of the phosphorylation status of protein tau by expression in the MDS1 and PHO85 deletion strains, respectively, allowed to confirm that hyperphosphorylation correlated with the immunoreactivity of tau to the conformation-dependent antibody MC1 and with the amount of sarkosyl-insoluble tau (Vandebroek et al., 2005). An inverse correlation between hyperphosphorylation of tau and the ability of tau to perform its normal physiological function, i.e. to bind and stabilize microtubuli, could also be demonstrated (Vandebroek et al., 2006).

A detailed analysis of several clinical tau mutants produced in these humanized yeast models demonstrated that the mutants tau-P301L and tau-R406W were less phosphorylated at Ser409 and that this coincided with a markedly lower level of the sarkosyl-insoluble fraction, suggesting that the PG5 epitope is an important determinant for tau aggregation. This finding was substantiated by the observation that the synthetic tau-S409A mutant failed to produce significant amounts of sarcosyl-insoluble tau, while its pseudo-phosphorylated counterpart tau-S409E yielded more or comparable sarkosyl-insoluble tau as wild-type tau. It was further shown that oxidative stress and mitochondrial dysfunction strongly induced tau-insolubility independent of the phosphorylation status (Vanhelmont et al., 2010).

In addition, the humanized yeast strains also allowed to further elucidate the role of the peptidyl-prolyl cis/trans isomerase Pin1 in the pathophysiology of protein tau. Reminiscent of data recently obtained with mammalian systems (Hamdane et al., 2006), it was found that Pin1 and its yeast orthologue Ess1 lower phosphorylation of tau at Thr231 and reduce the level of the in pathologic tau-conformation detectable by MC1 (De Vos et al., International Journal of Alzheimer's Disease Volume 2011 (2011), Article ID 428970, 16 pages).

In order to specifically detect pathogenic forms of tau, several strategies have been attempted. Specific detection of (hyper)phosphorylated tau is one of the approaches developed. These antibodies only recognize their epitopes in their phosphorylated state. Examples of antibodies specific for (hyper)phosphorylated tau are AT8, specific for P-Ser202/P-Ser205 (WO 1993/008302)(Mercken et al., 1992), AT100, specific for P-Thr212/P-Ser214 (Zheng-Fischhofer et al., 1998), AT180, specific for P-Thr231/P-Ser235 (WO 1995/017429), AT270, specific for P-Thr181 (WO 1995/017429), AD2, specific for P-Ser396/P-Ser404 (Buée-Scherrer et al., 1996), and PG5, specific for P-Ser409 (Jicha et al., 1999), anti-Tau pS422 specific for P-Ser422 (WO2012/142423), An alternative approach is the detection of pathogenic tau species with antibodies recognizing a conformational epitope of pathogenic tau. Examples of such antibodies are A1z50, whose conformational epitope encompasses the N-terminus and one or more microtubule-binding repeats of a single tau molecule (Carmel et al., 1996), and MC1 having a conformational epitope comprising amino acids 5-15 and 312-322 (Jicha et al., 1997). Conformational epitopes may be continuous or not, but typically, they are destroyed by denaturation, e.g. during SDS-PAGE.

Still another strategy has been the detection of processed tau by specific antibodies. Examples of such antibodies include mAb 423, which recognizes tau truncated at Glu391 (Novak et al., 1993), and DC11, which specifically binds to tau truncated at both the N- and C-terminal ends present in AD brains but not in normal brains (Vechterova et al., 2003).

In still a further approach, antibodies have been generated against tau-liposomal vaccines and were shown to specifically bind to phosphorylated tau peptides (WO2010/115843 and WO2012/045882).

In the case of Aβ, antibodies have been developed that preferentially recognize oligomers and/or aggregates, such as protofibrillar aggregates (WO 2004/024090; WO 2005/123775; (Kayed et al., 2010)), amylospheroids (WO 2006/016644), dimeric and higher order oligomeric Aβ (WO 2007/062088), dimers (WO 2008/084402) oligomers and fibrils (WO 2007/096076), and small soluble oligomers called Aβ-derived diffusible ligands (ADDLs; WO 2003/104437; WO 2006/014478; WO 2006/055178). Also for α-synuclein, aggregation of which in neuronal cytoplasmic inclusions known as Lewy bodies is a hallmark for Parkinson's Disease, antibodies have been disclosed that specifically detect oligomeric forms (Emadi et al., 2007; Emadi et al., 2009).

To date, despite several years of research on tau aggregation, no antibodies preferentially binding aggregated tau are available. The present invention provides tau antibodies or antibody fragments preferentially binding to phosphorylated tau aggregates, compositions comprising such antibodies or antibody fragments, nucleic acids encoding such antibodies or antibody fragments, and cell lines and hybridomas secreting such antibodies or antibody fragments. Also provided are methods to induce an immune response towards phosphorylated tau aggregates in an animal, as well as methods to obtain the antibodies or antibody fragments of the invention. The invention further provides methods and kits for the detection of aggregated tau and for the in vitro diagnosis of tauopathies using these antibodies or antibody fragments. Further provided are methods to identify compositions which interfere with formation or stability of such tau aggregates. Also provided are prophylactic or therapeutic compositions for the prevention or treatment of a tauopathy, comprising the antibody or antibody fragment of the invention.

SUMMARY OF THE INVENTION

The present invention relates to improved methods and/or assays for measuring phosphorylated tau and phosphorylated tau aggregates and/or tau fragments. The present invention further relates to certain types of therapy based on the treatment of patients identified as expressing or developing phosphorylated tau and phosphorylated tau aggregates in their body parts. The invention hereto provides for monoclonal antibodies binding to phosphorylated tau and/or phosphorylated tau aggregates and/or tau fragments, and for hybridoma's producing such monoclonal antibodies. The invention also provides for epitopes binding to the monoclonal antibodies of the present invention. Some embodiments of the invention are set forth in claim format directly below:

One embodiment (1) relates to an isolated tau antibody, antibody-like scaffold or antibody fragment, characterized in that it binds to phosphorylated tau aggregates.

One embodiment (2) relates to an antibody, antibody-like scaffold or antibody fragment according to embodiment 1, wherein the light chain variable region further comprises in a CDR1 region an amino acid sequence as set out in SEQ ID NO: 9, in a CDR2 region an amino acid sequence as set out in SEQ ID NO: 10 and in a CDR3 region an amino acid sequence as set out in SEQ ID NO: 11; and wherein a heavy chain variable region comprises in a CDR1 region an amino acid sequence as set out in SEQ ID NO: 12, in a CDR2 region an amino acid sequence as set out in SEQ ID NO: 13 and in a CDR3 region an amino acid sequence as set out in SEQ ID NO: 14.

One embodiment (3) relates to an antibody, antibody-like scaffold or antibody fragment according to embodiment 1, further characterized in that it comprises at least one complementarity determining region (CDR) having an amino acid sequence selected from the group consisting of SEQ ID NO. 12 to SEQ ID NO. 14 and SEQ ID NO. 9 to SEQ ID NO. 11, or an amino acid sequence which has at least 80% identity to an amino acid sequence selected from the group consisting of SEQ ID NO. 9 to SEQ ID NO. 11 and SEQ ID NO. 12 to SEQ ID NO. 14.

One embodiment (4) relates to an antibody, antibody-like scaffold or antibody fragment according to embodiment 1, further characterized in that it comprises at least one complementarity determining region (CDR) having an amino acid sequence selected from the group consisting of SEQ ID NO. 12 to SEQ ID NO. 14 and SEQ ID NO. 9 to SEQ ID NO. 11, or an amino acid sequence which has at least 90% identity to an amino acid sequence selected from the group consisting of SEQ ID NO. 9 to SEQ ID NO. 11 and SEQ ID NO. 12 to SEQ ID NO. 14.

One embodiment (5) relates to an antibody, antibody-like scaffold or antibody fragment according to embodiment 1, further characterized in that it comprises at least one variable domain having an amino acid sequence selected from the group consisting of SEQ ID NO. 15, 16, 17 and 18, or an amino acid sequence which has at least 80% identity to an amino acid sequence selected from the group consisting of SEQ ID NO. 15, 16, 17 and 18.

One embodiment (6) relates to an antibody, antibody-like scaffold or antibody fragment according to embodiment 1, further characterized in that it comprises at least one variable domain having an amino acid sequence which has at least 90% identity to an amino acid sequence selected from the group consisting of SEQ ID NO. 15, 16, 17 and 18.

One embodiment (7) relates to an antibody, antibody-like scaffold or antibody fragment according to embodiment 1, further characterized in that it comprises at least one variable domain having an amino acid sequence which has at least 95% identity to an amino acid sequence selected from the group consisting of SEQ ID NO. 15, 16, 17 and 18.

One embodiment (8) relates to an antibody, antibody-like scaffold or antibody fragment according to embodiment 1, further characterized in that it comprises at least one heavy chain variable domain having an amino acid sequence selected from the group consisting of SEQ ID NO. 15 and 17, or an amino acid sequence which has at least 80% identity to an amino acid sequence selected from the group consisting of SEQ ID NO. 15 and 17.

One embodiment (9) relates to an antibody, antibody-like scaffold or antibody fragment according to embodiment 1, further characterized in that it comprises at least one light chain variable domain having an amino acid sequence selected from the group consisting of SEQ ID NO. 16 and 18, or an amino acid sequence which has at least 80% identity to an amino acid sequence selected from the group consisting of SEQ ID NO. 16 and 18

One embodiment (10) relates to an antibody, antibody-like scaffold or antibody fragment according to embodiment 1, further characterized in that it comprises at least one heavy chain variable domain having an amino acid sequence selected from the group consisting of SEQ ID NO. 15 and 17, or an amino acid sequence which has at least 90% identity to an amino acid sequence selected from the group consisting of SEQ ID NO. 15 and 17.

One embodiment (11) relates to an antibody, antibody-like scaffold or antibody fragment according to embodiment 1, further characterized in that it comprises at least one light chain variable domain having an amino acid sequence selected from the group consisting of SEQ ID NO. 16 and 18, or an amino acid sequence which has at least 90% identity to an amino acid sequence selected from the group consisting of SEQ ID NO. 16 and 18

One embodiment (12) relates to an antibody, antibody-like scaffold or antibody fragment according to embodiment 1, wherein the light chain variable region further comprises in a CDR1 region an amino acid sequence as set out in SEQ ID NO: 22, in a CDR2 region an amino acid sequence as set out in SEQ ID NO: 23 and in a CDR3 region an amino acid sequence as set out in SEQ ID NO: 24; and wherein a heavy chain variable region comprises in a CDR1 region an amino acid sequence as set out in SEQ ID NO: 19, in a CDR2 region an amino acid sequence as set out in SEQ ID NO: 20 and in a CDR3 region an amino acid sequence as set out in SEQ ID NO: 21.

One embodiment (13) relates to an antibody, antibody-like scaffold or antibody fragment according to embodiment 1, further characterized in that it comprises at least one complementarity determining region (CDR) having an amino acid sequence selected from the group consisting of SEQ ID NO. 19 to SEQ ID NO. 21 and SEQ ID NO. 22 to SEQ ID NO. 24, or an amino acid sequence which has at least 80% or 90% or 95% identity to an amino acid sequence selected from the group consisting of SEQ ID NO. 19 to SEQ ID NO. 21 and SEQ ID NO. 22 to SEQ ID NO. 24.

One embodiment (14) relates to an antibody, antibody-like scaffold or antibody fragment according to embodiment 1, further characterized in that it comprises at least one variable domain having an amino acid sequence selected from the group consisting of SEQ ID NO. 25 and SEQ ID NO. 26, or an amino acid sequence which has at least 80% or 90% or 95% identity to an amino acid sequence selected from the group consisting of SEQ ID NO. 25 and SEQ ID NO. 26.

One embodiment (15) relates to an antibody, antibody-like scaffold or antibody fragment according to any one of the embodiments 1 to 14, which is a monoclonal antibody.

One embodiment (16) relates to an antibody, antibody-like scaffold or antibody fragment according to any one of the embodiments 1 to 14, which is a mouse monoclonal IgG1 subtype.

One embodiment (17) relates to an antibody, antibody-like scaffold or antibody fragment according to any one of the embodiments 1 to 14, which is a humanized antibody or fragment thereof of for instance a single-chain antibody, Fv" fragment, a Fab fragment (e.g. Fab' fragment or a F(ab') fragment) or a single domain antibodies.

One embodiment (18) relates to an antibody, antibody-like scaffold or antibody fragment according to any one of the embodiments 1 to 14, which is a human antibody or fragment thereof.

One embodiment (19) relates to an isolated tau antibody, antibody-like scaffold or antibody according to embodiment 1, characterized in that it preferentially binds to phosphorylated tau aggregate.

One embodiment (20) relates to an isolated tau antibody, antibody-like scaffold or antibody according to embodiment 1, characterized in that it binds to phosphorylated tau aggregate and to unphosphorylated tau.

One embodiment (21) relates to an antibody or antibody fragment of embodiment 1, further characterized in that it is secreted by the cell line selected from the group consisting of hybridoma cell line ADx210 deposited under the Budapest Treaty at the Belgian Coordinated Collections of Microorganisms BCCM™/LMBP Collection under No. LMBP 8347CB (name of depositor: Dr Eugeen Vanmechelen; address of the depositor at the time of deposit (7 Apr. 2011): Innogenetics N.V., Industriepark 7, box 4, B-9052 Zwijnaarde; current address of the depositor: ADx NeuroSciences, Industriepark Zwijnaarde 4, 9052 Gent-Zwijnaarde), and hybridoma cell line ADx211 deposited under the Budapest Treaty at the Belgian Coordinated Collections of Microorganisms BCCM™/LMBP Collection under No. LMBP 8348CB (name of depositor: Dr Eugeen Vanmechelen; address of the depositor at the time of deposit (7 Apr. 2011): Innogenetics N.V., Industriepark 7, box 4, B-9052 Zwijnaarde; current address of the depositor: ADx NeuroSciences, Industriepark Zwijnaarde 4, 9052 Gent-Zwijnaarde), and hybridoma cell line ADx215 deposited under the Budapest Treaty at the Belgian Coordinated Collections of Microorganisms BCCM™/LMBP Collection under No. LMBP 9679CB.

Deposit No. LMBP 9679CB was made on May 31, 2012 at the Belgian Coordinated Collections of Micro-organisms (BCCM) LMBP PLASMID COLLECTION, Ghent University—Department of Biomedical Molecular Biology, Technologiepark 927, 9052 Gent-Zwijnaarde, Belgium, under the Budapest Treaty on the International Recognition of the Deposit of Micro-Organisms for the Purposes of Patent Procedure.

One embodiment (22) relates to an antibody or antibody fragment according to any one of the embodiments 1 to 19, further characterized in that it is secreted by the hybridoma cell line ADx210 deposited under the Budapest Treaty at the Belgian Coordinated Collections of Microorganisms BCCM™/LMBP Collection under No. LMBP 8347CB.

One embodiment (23) relates to an antibody or antibody fragment according to embodiments 1 to 19, further characterized in that it is secreted by the hybridoma cell line ADx211 deposited under the Budapest Treaty at the Belgian Coordinated Collections of Microorganisms BCCM™/LMBP Collection under No. LMBP 8348CB.

One embodiment (24) relates to an antibody or antibody fragment according to embodiments 12 to 18 and 20, further characterized in that it is secreted by the hybridoma cell line ADx215 deposited under the Budapest Treaty at the Belgian Coordinated Collections of Microorganisms BCCM™/LMBP Collection under No. LMBP 9679CB One embodiment (25) relates to a tau antibody, antibody-like scaffold or antibody fragment according to any one of the previous embodiments 1 to 24, further comprising a protein-transduction domain (PTD).

One embodiment (26) relates to a tau antibody, antibody-like scaffold or antibody fragment according to any one of the previous embodiments 1 to 24, further comprising protein delivery system, for instance a peptide or protein motif crosses the cell plasma membrane, to deliver the tau antibody, tau antibody-like scaffold or tau antibody fragment intracellular.

One embodiment (27) relates to a tau antibody, antibody-like scaffold or antibody fragment according to any one of the previous embodiments 1 to 24, further comprising a protein-transduction domains (PTDs) to mediate delivery of said tau antibody, tau antibody-like scaffold or tau antibody fragment into cells.

One embodiment (28) relates to a tau antibody, antibody-like scaffold or antibody fragment according to any one of the previous embodiments 1 to 24, further comprising a carrier reagent such as lipid liposomes or the like that can complex with the tau antibody, tau antibody-like scaffold or tau antibody fragment for promoting delivery of said tau antibody, tau antibody-like scaffold or tau antibody fragment into cells.

One embodiment (29) relates to a tau antibody, antibody-like scaffold or antibody fragment according to any one of the previous embodiments 1 to 24, further comprising a carrier reagent to promote the delivery of the tau antibody, tau antibody-like scaffold or tau antibody fragment into the cell, thus transfecting the cells for instance the carrier reagent being a bioactive cell membrane-permeable reagent, or other peptides containing protein-transduction domains (PTDs) (i.e., single peptide sequences comprising about 15 to about 30 residues) and such membrane-transducing peptides being of the group consisting of Trojan peptides, human immuodeficiency virus (HIV)-1 transcriptional activator (TAT) protein or its functional domain peptides, and other peptides containing protein-transduction domains (PTDs) derived from translocation proteins such as *Drosophilia* homeotic transcription factor Antennapedia (Antp) and herpes simplex virus DNA-binding protein, VP22, and the like.

One embodiment (30) relates to a tau antibody, antibody-like scaffold or antibody fragment according to any one of the previous embodiments 1 to 24, further comprising a carrier reagent to promote the delivery of the tau antibody, tau antibody-like scaffold or tau antibody fragment into the cell, thus transfecting the cells for instance the carrier reagent being a bioactive cell membrane-permeable reagent, or other peptides containing protein-transduction domains (PTDs) (i.e., single peptide sequences comprising about 15 to about 30 residues) and such membrane-transducing peptides being of the group consisting of penetratin 1, Pep-1 (Chariot reagent, Active Motif Inc., CA) and HIV GP41 fragment (519-541).

One embodiment (31) relates to a tau antibody, antibody-like scaffold or antibody fragment according to any one of the previous embodiments 1 to 24, further comprising a helper reagent to enhance the efficiency of delivery of said tau antibody, tau antibody-like scaffold or tau antibody fragment into the cells for instance such helper reagent such as DEAE-dextran, dextran, polylysine, polyethylamine, polyethylene glycol, acrylamide, a RGD peptide, such as Arg-Gly-Asp-Ser (SEQ ID NO. 52), Arg-Gly-Asp-Ser-Pro-Ala-Ser-Ser-Lys-Pro (SEQ ID NO. 53), and a mixture of a hydrogel and a RGD peptide.

One embodiment (32) relates to an isolated nucleic acid comprising a polynucleotide encoding the antibody or antibody fragment according to any one of the embodiments 1 to 24.

One embodiment (33) relates to an isolated cell line producing the antibody or antibody fragment according to any one of embodiments 1 to 24.

One embodiment (34) relates to a cell line of embodiment 33, selected from the group consisting of hybridoma cell line ADx210 deposited under the Budapest Treaty at the Belgian Coordinated Collections of Microorganisms BCCM™/LMBP Collection under No. LMBP 8347CB, and hybridoma cell line ADx211 deposited under the Budapest Treaty at the Belgian Coordinated Collections of Microorganisms BCCM™/LMBP Collection under No. LMBP 8348CB, and hybridoma cell line ADx215 deposited under the Budapest Treaty at the Belgian Coordinated Collections of Microorganisms BCCM™/LMBP Collection under No. LMBP 9679CB.

One embodiment (35) relates to a method for inducing an immune response towards phosphorylated tau aggregates in an animal, comprising administering to said animal phosphorylated tau aggregates, obtainable by a method comprising expression of tau in a pho85Δ yeast strain.

One embodiment (36) relates to a method of embodiment 35 for obtaining a tau-specific antibody or antibody fragment binding to phosphorylated tau aggregates.

One embodiment (37) relates to a use of the antibody or antibody fragment a according to any one of embodiments 1 to 24 in the detection of phosphorylated tau aggregates or in the in vitro diagnosis of a tauopathy.

One embodiment (38) relates to a method for detecting phosphorylated tau aggregates in a sample or for the in vitro diagnosis or monitoring of a tauopathy in a subject, comprising the following steps:
  contacting an antibody or antibody fragment according to any one of embodiments 1 to 24 with a sample under conditions suitable for producing an antigen-antibody complex; and
  detecting the formation of said antigen-antibody complex.

One embodiment (39) relates to a kit for the detection of phosphorylated tau aggregates or for the in vitro diagnosis or monitoring of a tauopathy in a subject, comprising the antibody or antibody fragment according to any one of embodiments 1 to 24.

One embodiment (40) relates to a kit to discriminate early stage Alzheimer's dementia, especially from other types of dementia in a subject, comprising the antibody or antibody fragment according to any one of embodiments 1 to 24.

One embodiment (41) relates to a kit comprising the antibody or antibody fragment according to any one of embodiments 1 to 24 to identify compositions which interfere with formation or stability of such phosphorylated tau aggregates.

One embodiment (42) relates to a kit comprising the antibody or antibody fragment according to any one of embodiments 1 to 24 for the detection of phosphorylated aggregated tau and for the diagnosis of diseases involving phoshorylated aggregated tau.

One embodiment (43) relates to a method for the identification of a composition that interferes with the formation or stability of phosphorylated tau aggregates, comprising the following steps:
  incubating tau in the presence of a test composition under conditions known to allow the formation of phosphorylated tau aggregates, or incubating phosphorylated tau aggregates in the presence of a test composition;
  detecting phosphorylated tau aggregates according to the method of embodiment 38;
  comparing the amount of phosphorylated tau aggregates detected in the previous step to the amount of phosphorylated tau aggregates detected after incubation in the absence of a test composition;
  concluding from the comparison of the previous step whether said test composition interferes with the formation or stability of phosphorylated tau aggregates.

One embodiment (44) relates to an antibody or antibody fragment according to any one of embodiments 1 to 24, for use in the treatment of a disease.

One embodiment (40) relates to phosphorylated tau aggregates, for instance obtainable by a method comprising expression of tau in a pho85Δ yeast strain, for use in the treatment of a disease.

One embodiment (45) relates to a prophylactic or therapeutic composition for the prevention or treatment of a tauopathy, comprising the antibody, antibody like fragment or antibody fragment according to any one of embodiments 1 to 31.

One embodiment (46) relates to a prophylactic or therapeutic composition for the prevention or treatment of a tauopathy, comprising phosphorylated tau aggregates for instance such obtainable by a method comprising expression of tau in a pho85Δ yeast strain.

One embodiment (47) relates to a prophylactic or therapeutic composition for the prevention or treatment of a tauopathy, comprising the antibody, antibody like fragment or antibody fragment according to any one of embodiments 1 to 31, for use in a treatment of a tau-related diseases or a tauopathies One embodiment (48) relates to a nucleic acid encoding such antibodies, antibody like fragments or antibody fragments according to 1 to 24

One embodiment (49) relates to a peptide representing an epitope of the tau protein, which epitope is recognized by an antibody according to any one of the embodiments 1 to 24

One embodiment (50) relates to a peptide according to embodiment 49 comprising, consisting essentially of, or consisting of the sequence represented by SEQ ID NO. 27.

One embodiment (51) relates to a peptide according to embodiment 49 comprising, consisting essentially of, or consisting of the sequence represented by SEQ ID NO. 29.

One embodiment (52) relates to a peptide according to embodiment 49, which peptide is 9 to 19 amino acids in length.

One embodiment (53) relates to a peptide according to embodiment 49 consisting of the sequence represented by SEQ ID NO. 27 or 28, which peptide is specifically recognized by an antibody binding to phosphorylated tau aggregates.

One embodiment (54) relates to a peptide according to embodiment 49 consisting of the sequence represented by SEQ ID NO. 27 or 28, which peptide is specifically recognized by the antibody ADx215.

DETAILED DESCRIPTION OF THE INVENTION

The invention relates in generally to phosphorylated tau and antibodies directed towards phosphorylated tau and phosphorylated tau aggregates. The invention can be implemented in a number of ways, including as a method, an assay, a kit and a composition of matter. In general, the order of the steps of disclosed methods may be altered within the scope of the invention. Embodiments will be discussed with reference to the accompanying figures, which depict one or more exemplary embodiments. Embodiments may be embodied in many different forms and should not be construed as limited to the embodiments set forth herein, shown in the figures and/or described below. Rather, these exemplary embodiments are provided to allow a complete disclosure that conveys the principles of the invention, as set forth in the claim, to those skilled in the art. For the purpose of clarity, technical material that is known in the technical fields related to the invention has not been described in detail so that the invention is not unnecessarily obscured. Unless indicated or defined otherwise, all terms used have their usual meaning in the art, which will be clear to the skilled person. Reference is further made to the standard handbooks, such as (1994; Sambrook and Russell, 2001; Delves et al., 2006; Krebs et al., 2009), as well as to the general background art cited herein.

As used in the specification and the attached claims, the use of "a," "an" and "the" include references to plural subject matter referred to unless the context clearly dictates otherwise. Thus, for example, reference to "a protein" includes a single catalyst as well as a combination or mixture of two or more proteins, reference to "an antigen" encompasses a combination or mixture of different antigens as well as a single antigen, and the like.

A term which is subsumed under another term may be embraced by the broader term or by the more narrow specific term as appropriate within the context of the use of that term. All terms used to describe the present invention are used within context The present invention provides isolated tau antibodies and antibody fragments, characterized in that they preferentially bind to phosphorylated tau aggregates. The invention provides isolated tau antibodies and antibody fragments characterized in that they bind phosphorylated tau aggregates but not unphosphorylated tau. The invention also provides isolated tau antibodies and antibody fragments characterized in that they bind phosphorylated tau aggregates and unphosphorylated tau. The invention further provides epitopes recognized by the isolated tau antibodies and antibody fragments.

As used herein, "tau", "tau protein", "tau isoform", "tau molecule", "tau variant", "tau mutant", "tau homologue" and "tau isoform" are used interchangeable to denote a polypeptide or protein that is encoded by at least one exon of a tau gene, irrespective of whether post-translational modifications are present or not. Such gene can encode a protein of the tau protein family mentioned above and derivatives thereof. Such proteins are characterised as one family among a larger number of protein families which co-purify with microtubules during repeated cycles of assembly and disassembly (Shelanski et al., 1973), and known as microtubule-associated-proteins (MAPs). The tau family in addition is characterised by the presence of a characteristic N-terminal segment which is shared by all members of the family, sequences of ~50 amino acids inserted in the N-terminal segment, which are developmentally regulated in the brain, a characteristic tandem repeat region consisting of 3 or 4 tandem repeats of 31-32 amino acids, and a C-terminal tail. A tau protein can in an embodiment comprise the amino acid sequence of "T40" with the sequence described in Goedert et al., 1989.

The terms "tau gene", "tau nucleic acid", "tau polynucleotide", "tau gene construct", "tau gene variant", "tau gene homologue", are used interchangeably and mean a naturally occurring tau gene, an allelic variant thereof, a homologue thereof, a mutated variant thereof, a transcript thereof, a part thereof, or a recombinant derivative thereof, including but not limited to single strand DNA (ssDNA), complementary DNA (cDNA), synthetic DNA, messenger RNA, encoding for tau, a tau isoform, a tau variant, a tau homologue, a tau mutant, or a part thereof.

Tau is a microtubule-associated protein (MAP) synthesized in neurons. Six major isoforms of tau having different physiological roles are derived from a single gene by alternative splicing (Goedert et al., 1989). The isoforms can contain 0, 1, or 2 N-terminal insertions (denoted as 0N, 1N and 2N iso forms, respectively) encoded by exons 2 and 3, and further 0 or 1 extra C-terminal microtubule-binding domain encoded by exon 10 (denoted as 3R and 4R, respectively). As such, the isoforms are denoted as 0N/3R, 0N/4R, 1N/3R, 1N/4R, 2N/3R, and 2N/4R. For instance in an embodiment of present invention the iso form is microtubule-associated protein tau iso form 1 [*Homo sapiens*] with the NCBI Reference Sequence: NP_058519.3 as deposited with accession number NP_058519 w on 26 Jun. 2011 (SEQ ID NO: 1 in this application). For instance in another embodiment of present invention the isoform is microtubule-associated protein tau isoform 2 [*Homo sapiens*] with NCBI Reference Sequence: NP_005901.2 as deposited under accession number NP_005901 NP_776088 date 26 Jun. 2011 (SEQ ID NO: 2 in this application). For instance in another embodiment of present invention the iso form is microtubule-associated protein tau isoform 3 [*Homo sapiens*] with the NCBI Reference Sequence: NP_058518.1 date 26 Jun. 2011 as deposited with the accession number NP_058518, version NP_058518.1 GI:8400711 (SEQ ID NO: 3 in this application). For instance in another embodiment of present invention the iso form is microtubule-associated protein tau isoform 4 [*Homo sapiens*] with NCBI Reference Sequence: NP_058525.1 date 26 Jun. 2011 as deposited with the accession number NP_058525, version NP_058525.1 GI:8400715 (SEQ ID NO: 4 in this application). For instance in another embodiment of present invention the iso form is microtubule-associated protein tau isoform 5 [*Homo sapiens*] with NCBI Reference Sequence: NP_001116539.1 date 26 Jun. 2011 as deposited with the accession number NP_001116539 version NP_001116539.1 GI:178557736 (Ref ID: 5 in this application). For instance in another embodiment of present invention the iso form is microtubule-associated protein tau isoform 6 [*Homo sapiens*] with NCBI Reference Sequence: NP_001116538.2 date 26 Jun. 2011 as deposited with the accession number NP_001116538 version NP_001116538.2 GI:294862258 (SEQ ID NO: 6 in this application). For instance in another embodiment of present invention the iso form is microtubule-associated protein tau isoform 7 [*Homo sapiens*] with NCBI Reference Sequence: NP_001190180.1 date 26 Jun. 2011 as deposited with accession number NP_001190180 version NP_001190180.1 GI:322303720 (SEQ ID NO: 7 in this application). For instance in another embodiment of present invention the iso form is microtubule-associated protein tau isoform 8 [*Homo sapiens*] with NCBI Reference Sequence: NP_001190181.1 date 26 Jun. 2011 as deposited with accession number NP_001190181 version NP_001190181.1 GI:322303747 (SEQ ID NO: 8 in this application)

The physiological function of tau is further regulated by phosphorylation. The longest isoform, tau-2N/4R, is 441 amino acids long and has 85 putative phosphorylation sites, the majority of which are located in and adjacent to the microtubule-binding domains. In tauopathies, hyperphosphorylation and aggregation of tau are observed, leading to the formation of intraneuronal deposits of tau aggregates such as paired helical filaments (PHF or PHFtau) and neurofibrillary tangles (NFT) (Mandelkow et al., 2003; Drewes, 2004).

As used herein, "phosphorylated tau" and "phospho-tau" are used interchangeably to denote tau protein of which at least one amino acid is phosphorylated. By "hyperphosphorylated tau" is meant tau protein of which at least two amino acids are phosphorylated.

"Tau aggregate", "aggregated tau", "tau oligomer", "oligomeric tau", "oligomeric form of tau", and "tau conformer" are used interchangeably to denote protein structures comprising more than one tau molecule, as opposed to "monomeric tau" and "tau monomers". As such, these terms include but are not limited to dimers, trimers, tetramers, pentamers, hexamers, heptamers, octamers, enneamers, decamers, dodecamers, icosamers, triacontamers, tetracontamers, or higher-order oligomers and multimers of tau, non-limiting examples of which are granular aggregates, PHF, straight filaments and NFT. The monomers in tau aggregates can be in any form of tau, as described above. Individual monomers in tau aggregates may be homogenous, in that all monomers of an aggregate are alike, or heterogenous, in that individual aggregates comprise different forms of tau. The monomers in tau aggregates may be covalently linked to each other, or non-covalently by weak intermolecular forces, including but not limited to hydrophobic or hydrophylic interactions, hydrogen bonding, salt bridges, or van der Waals forces. A population of aggregates can be homogenous, in that all individual aggregates in that population are alike, or heterogenous, in that individual aggregates in the population may differ from others.

By "phosphorylated tau aggregates" is meant aggregates of phosphorylated tau.

Tau aggregates may be soluble or insoluble. In a particular embodiment, the phosphorylated tau aggregates are soluble. By "soluble" is meant that the tau aggregates will dissolve in fluid. The term "fluid" includes bodily fluids like CSF, blood, plasma, serum, urine, etc., physiological solutions, know to those skilled in the art and including but not limited to physiological salt solutions, and may comprise additional agents like buffering agents, detergents, surfactants, sugars, chelating agents, enzyme inhibitors, reducing agents, oxidizing agents, etc. By "insoluble" is meant that the tau aggregates will precipitate out of the fluid.

The solubility of tau aggregates can therefore be determined under physiological conditions, or for example in the presence of detergents like sarkosyl (synonyms: N-lauroyl-sarcosine sodium salt and N-dodecanoyl-N-methylglycine sodium salt) or SDS (synonym: lauryl sulfate sodium salt). The skilled person is aware of the existing protocols to determine solubility of tau aggregates in sarkosyl-containing fluids, and to isolate sarkosyl-soluble and -insoluble tau aggregates. Examples of such protocols are found in the Examples and in (Greenberg and Davies, 1990; Vandebroek et al., 2005).

Further, tau aggregates may be stable in the presence of SDS and/or reducing agents like β-mercaptoethanol (β-ME), or they may disintegrate into lower order oligomers or monomers and/or solubilize in the presence of SDS and/or β-ME. Disintegration and/or solubilization of tau aggregates may occur at a range between 0.1 to 10%, or more, SDS in the presence or absence of reducing agent. Preferably, it occurs at 0.1, 0.2, 0.4, 0.6, 0.8, 1.0, 1.2, 1.5, 2.0, 2.5, 3.0, 4.0, 5.0, 7.5, 10%, or more SDS in the presence or absence of reducing agent. Disintegration and/or solubilization of tau aggregates may occur at 0.1, 0.2, 0.4, 0.6, 0.8, 1.0, 1.2, 1.5, 2.0, 2.5, 3.0, 4.0, 5.0, 7.5, 10 mM, or more reducing agent in the presence or absence of SDS. Disintegration and/or solubilization of tau aggregates may occur without boiling or after boiling.

In a particular embodiment of the invention, the phosphorylated tau aggregates are obtainable by production of tau in a yeast strain in which the PHO85 gene has been deleted (pho85Δ strain). Phosphorylated tau aggregates may be used in total extracts of the producing yeast, or after purification. A possible protocol for purification of phosphorylated tau aggregates has been described in (Vandebroek et al., 2005), and is further described in the Examples. In a more preferred embodiment, tau being produced is human tau. In an even more preferred embodiment, tau being produced is the 2N/4R iso form of human tau.

In a particular embodiment, the phosphorylated tau aggregates have an apparent molecular weight which is greater than that of monomeric tau, as estimated by electrophoretic mobility. In a more preferred embodiment, the phosphorylated tau aggregates comprise dimers and/or trimers of phosphorylated tau. In an even more preferred embodiment, tau is the 2N/4R isoform of human tau and the phosphorylated tau aggregates have an apparent molecular weight which is greater than 75 kDa, more preferably greater than 80, 90, 100, 110, 120, 130, or 140 kDa.

Tauopathy is a class of degenerative diseases resulting from the pathological aggregation of tau protein cells in case of neurodegeneration cells of the human brain, and in case of type 2 diabetes taupathy in the β-cells. Frequent concomitant manifestation of type 2 diabetes mellitus (T2DM) and Alzheimer's disease (AD) has been recently demonstrated by epidemiological studies. There are functional similarities between β-cells and neurons, such as secretion on demand of highly specific molecules in a tightly controlled fashion. An additional similarity represents the age-related alteration of hyperphosphorylated tau in AD patients. Similarly, alterations have been identified in β-cells of T2DM patients. The islet amyloid polypeptide has been associated with β-cell apoptosis. As a consequence of increasing age, the accumulation of highly modified proteins together with decreased regenerative potential might lead to increasing rates of apoptosis. Moreover, reduction of β-cell replication capabilities results in reduction of β-cell mass in mammals, simultaneously with impaired glucose tolerance. The new challenge is to learn much more about age-related protein modifications. This can lead to new treatment strategies for reducing the incidence of T2DM and AD (Maj et al., 2011). The best known thauopaty is Alzheimer's disease (AD), where tau protein is deposited within neurons in the form of neurofibrillary tangles (NFTs). They were first described by the eponymous Alois Alzheimer in one of his patients suffering from the disorder. Tangles are formed by hyperphosphorylation of a microtubule-associated protein known as tau, causing it to aggregate in an insoluble form. The precise mechanism of tangle formation is not completely understood, and it is still controversial whether tangles are a primary causative factor in the disease or play a more peripheral role. AD is also classified as an amyloidosis because of the presence of senile plaques. The degree of aggregations of hyperphosphorylated tau protein (PHF), or "paired helical filaments") involvement in AD is defined by Braak stages. Braak stages I and II are used when NFT involvement is confined mainly to the transentorhinal region of the brain, stages III and IV when there's also involvement of limbic regions such as the hippocampus, and V and VI when there's extensive neocortical involvement. This should not be confused with the degree of senile plaque involvement, which progresses differently. Other conditions in which neurofibrillary tangles are commonly observed include: Dementia pugilistica (chronic traumatic encephalopathy), Frontotemporal dementia and parkinsonism linked to chromosome 17 however without detectable β-amyloid plaques, Lytico-Bodig disease (Parkinson-dementia complex of Guam), Tangle-predominant dementia, with NFTs similar to AD, but without plaques, tends to appear in the very old, Ganglioglioma and gangliocytoma, Meningioangiomatosis, Subacute sclerosing panencephalitis. As well as lead encephalopathy, tuberous sclerosis, Hallervorden-Spatz disease, and lipofuscinosis. In Pick's disease and corticobasal degeneration tau proteins are deposited in the form of inclusion bodies within swollen or "ballooned" neurons. Argyrophilic grain disease (AGD), another type of dementia, is marked by the presence of abundant argyrophilic grains and coiled bodies on microscopic examination of brain tissue. Some consider it to be a type of Alzheimer disease. It may co-exist with other tauopathies such as progressive supranuclear palsy and corticobasal degeneration. Some other tauopathies include: Frontotemporal dementia, Frontotemporal lobar degeneration, The non-Alzheimer's tauopathies are sometimes grouped together as "Pick's complex".

The terms "antibody" and "antibodies" are recognized in the art and refer to proteins also known as immunoglobulins that bind to antigens. It is to be understood that these terms encompass conventional vertebrate antibodies like IgA, IgD, IgE, IgG, IgM, IgT, IgX and IgY, composed of at least two heavy and two light chains, as well as antibodies only composed of two heavy chains ($V_{HH}$ antibodies, IgNAR, heavy-chain antibodies, single-domain antibodies or nanobodies), and single-chain antibodies. In the case of conventional antibodies, the antigen-binding sites are contributed to by the variable domains of both the heavy and light chains ($V_H$ and $V_L$). The term "variable domain" refers to the part or domain of an antibody which is partially or fully responsible for antigen binding. Generally, variable domains will be amino acid sequences that essentially consist of 4 framework regions (FR1 to FR4 respectively) and 3 complementarity determining regions (CDR1 to CDR3 respectively), or any suitable fragment of such an amino acid sequence which usually contains at least some of the amino acid residues that form at least one of the CDR's. Such variable domains and fragments are most preferably such that they comprise an immunoglobulin fold or are capable for forming, under suitable conditions, an immunoglobulin fold. Each CDR may contribute to a greater or lesser extent to antigen binding by the antibody. Single domain antibodies or heavy-chain antibodies can be found in camelids and sharks, and each of the antigen-binding sites of these antibodies is formed by a single heavy chain variable domain ($V_{HH}$) only. Therefore, only three CDRs contribute to a greater or lesser extent to each antigen-binding site. Single chain antibodies (scFv) are derived from conventional antibodies by translational fusion of the $V_H$ and $V_L$ domains, separated by a flexible linker, into a single antigen-binding domain. Framework sequences of an antibody may be altered without altering the antigenic specificity of the antibody, or in order to change the binding affinity of the antibody. Furthermore, conventional antibodies may switch classes or isotypes without substantially affecting antigen-binding characteristics.

By the term "antibody fragment" is meant a fragment of an antibody that largely retains antigen-binding capacity of the antibody from which it is derived. Therefore, a tau-specific antibody fragment of the invention is capable of preferentially binding to phosphorylated tau aggregates. Antigen-binding capacity is determined by the variable domain or domains, more particularly by 1, 2, 3, 4, 5 or 6 CDRs located in the $V_H$ and/or $V_L$ domains in the case of conventional and single-chain antibodies, and 1, 2 or 3 CDRs in the case of single-domain antibodies. Preferred antibody fragments of the invention therefore comprise antigen-binding sites comprising 1, 2, 3, 4, 5 or 6 CDRs. Two or more CDRs may be physically separated from each other by connecting regions to provide a framework structure for the CDRs. More preferred antibody fragments of the invention comprise antigen-binding sites comprising 1 or 2 variable domains. Examples of antibody fragments are well-known to the skilled person and include the monovalent antigen-binding fragments (Fab), bivalent F(ab')$_2$ fragments, Fv fragments (e.g. single chain antibodies scFv), miniaturized antibodies, single-domain antibody fragments like nanobodies (Nelson, 2010). Antibody fragments of the invention may be obtained by enzymatic or chemical proteolysis, or by recombinant DNA technology techniques well known to the skilled person.

Antibodies and antibody fragments of the invention may be further chemically conjugated, non-covalently bound, or translationally fused to other proteins. Single chain antibodies scFv are an example of translational fusion between a $V_H$ and a $V_L$ domain. Further examples are albumin-conjugated antibodies or antibody fragments, bivalent diabodies, and monospecific and bispecific tandem svFcs (Nelson, 2010).

Antibodies and antibody fragments of the invention may be further modified. Examples of such modifications include the addition of detectable enzymatic, fluorescent, luminescent, or radioactive marker groups or molecules that act in detection such as streptavidin. Other examples include the chemical modification to alter the half-life of antibodies and antibody fragments, such as PEGylation. Still other examples add effector moieties to antibodies and antibody fragments, such as toxins, radioisotopes, enzymes, cytokines, and antigens (Nelson, 2010).

Antibodies or antibody fragments may be further modified into an antibody-derived scaffold or antibody-like scaffolds that largely retains antigen-binding capacity of the antibody or antibody fragments from which it is derived. Examples of antibody-derived scaffolds or antibody-like scaffolds are for domain antibody (dAb) that selectively or preferentially bind the same epitope as a natural antibody for instance dAb with fully human frameworks, for instance dAb fused to a human Fc domain or for instance nanobodies engineered in a molecule that has an IgG-like circulating half-life in humans or antibody fragments with retained antigen-binding capacity or domain antibody with active scaffolds for controlled and cell delivery.

In one embodiment, the antibodies and antibody fragments of the invention are humanized. Antibody fragments derived from an antibody of the invention can be fused to the Fc region of a human antibody, in order to obtain humanized antibodies and antibody fragments. Humanized antibodies or antibody fragments can also be obtained by grafting of one or more CDRs or only their specificity-determining residues (SDRs), optionally together with one or more framework residues important for optimal CDR functionality, of a non-human antibody having the desired antigen-binding specificity, into framework polypeptide sequences of a human antibody or antibody fragment, or even into a universal humanized nanobody scaffold. Methods to humanize antibodies are well known to those skilled in the art (see e.g. (De Pascalis et al., 2002; Kashmiri et al., 2005; Almagro and Fransson, 2008; Vincke et al., 2009; Borras et al., 2010; Harding et al., 2010)).

The antibody fragments of the present invention can also be generated using various phage display methods known in the art. In phage display methods, functional antibody domains are displayed on the surface of phage particles which carry the polynucleotide sequences encoding them. In particular, such phage can be utilized to display epitope-binding domains expressed from a repertoire or combinatorial antibody library (e.g., human or murine). Phage expressing an epitope-binding domain that binds the antigen of interest can be selected or identified with antigen, e.g., using labeled antigen bound or captured to a solid surface or bead. Phages used in these methods are typically filamentous phage including fd and M13 binding domains expressed from phage with antigen-binding antibody domains recombinantly fused to either the phage gene III or gene VIII protein. Examples of phage display methods that can be used to make the antibodies or antibody fragments of the present invention include those disclosed in (Kettleborough et al., 1994; Burton and Barbas, III, 1994; Brinkmann et al., 1995; Ames et al., 1995; Persic et al., 1997); WO/1992/001047; WO 5 90102809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108.

After phage selection, the regions of the phage encoding the fragments can be isolated and used to generate the epitope-binding fragments through expression in a chosen host, including mammalian cells, insect cells, plant cells, yeast, and bacteria, using recombinant DNA technology. For example, techniques to recombinantly produce antigen-binding fragments can also be employed using methods known in the art such as those disclosed in WO 92/22324; (Better et al., 1988; Mullinax et al., 1992; Sawai et al., 1995). Examples of techniques which can be used to produce single-chain Fvs and antibodies include those described in U.S. Pat. Nos. 4,946,778 and 5,258,498; (Skerra and Pluckthun, 1988; Huston et al., 1991; Shu et al., 1993).

Changes may be made to the residues that comprise the CDRs without interfering with the ability of the antibody to recognize and bind its cognate epitope. For example, changes that do not affect epitope recognition, yet increase the binding affinity of the antibody for the epitope may be made. Several studies have surveyed the effects of introducing one or more ammo acid changes at various positions in the sequence of an antibody, based on the knowledge of the primary antibody sequence, on its properties such as binding and level of expression (Yang et al., 1995; Vaughan et al., 1998; Rader et al., 1998). In these studies (so called affinity maturation techniques), altered versions of the antibody have been generated by changing the sequences of the encoding genes in the CDR1, CDR2, CDR3, or framework regions, using methods such as oligonucleotide-mediated site-directed mutagenesis, cassette mutagenesis, error-prone PCR, DNA shuffling, or mutator-strains of E. coli (Vaughan et al., 1998). These methods of changing the sequence of the antibody have resulted in improved affinities of the resulting antibodies (Gram et al., 1992; Davies and Riechmann, 1996; Thompson et al., 1996; Boder et al., 2000; Furukawa et al., 2001; Short et al., 2002).

By "tau antibody" and "tau antibody fragment" are meant an antibody and antibody fragment, respectively, that binds to tau. The tau antibodies and tau antibody fragments of the invention are thus antibodies and antibody fragments that bind tau and preferentially bind to phosphorylated tau aggregates. As the skilled person will appreciate, this does not necessarily imply that the antibodies or antibody fragments of the invention bind phosphorylated tau aggregates through a phosphorylated epitope of tau in these aggregates.

The phrase "preferably bind(s)" or "specifically bind(s)" or "bind(s) specifically" when referring to a peptide refers to a peptide molecule which has intermediate or high binding affinity, exclusively or predominately, to a target molecule. The phrases "preferably bind(s) to" or "specifically binds to" refers to a binding reaction which is determinative of the presence of a target protein in the presence of a heterogeneous population of proteins and other biologics. Thus, under designated assay conditions, the specified binding moieties bind preferentially to a particular target protein and do not bind in a significant amount to other components present in a test sample. Specific binding to a target protein under such conditions may require a binding moiety that is selected for its specificity for a particular target antigen. A variety of assay formats may be used to select ligands that are specifically reactive with a particular protein. For example, solid-phase ELISA immunoassays, immunoprecipitation, Typically a specific or selective reaction will be at least twice background signal or noise and more typically more than 10 times background. For instance an antibodies and antibody fragments of the invention preferentially bind to phosphorylated tau aggregates, whereby by "preferentially binding", "preferentially recognizing" or "preferentially reacting with" is meant that the antibodies or antibody fragments show greater binding capacity for phosphorylated tau aggregates as compared to any other antigen, including phosphorylated and non-phosphorylated tau monomers. The binding capacity of an antibody or antibody fragment to an antigen is reflective of its affinity and/or avidity for that antigen.

In a preferred embodiment of the invention, the antibody of the invention is monoclonal. The term "monoclonal antibody" is well recognized in the art and refers to an antibody or a homogenous population of antibodies that is derived from a single clone. Individual antibodies from a monoclonal antibody population are essentially identical, in that minor naturally occurring mutations may be present. Antibodies from a monoclonal antibody population show a homogenous binding specificity and affinity for a particular epitope.

The term "naturally-occurring" as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

The term "rearranged" refers to a configuration of a heavy chain or light chain immunoglobulin locus wherein a V segment is positioned immediately adjacent to a D-J or J segment in a conformation encoding essentially a complete VH or VL domain, respectively. A rearranged immunoglobulin gene locus can be identified by comparison to germline DNA; a rearranged locus has at least one recombined heptamer/nonamer homology element.

The term "unrearranged" or "germline configuration" in reference to a V segment refers to the configuration wherein the V segment is not recombined so as to be immediately adjacent to a D or J segment.

Manuals are available for the many skilled in the art for achieving such antibodies or rearranged antibodies. An overview is provided in the recent work, Handbook of Therapeutic Antibodies Edited by Stefan Dübel, Wiley-VCH Verlag GmBH & Co, KGaA.

The term "nucleic acid" is intended to include DNA molecules and RNA molecules. A nucleic acid can be single-stranded or double-stranded.

The term "substantially identical," in the context of two nucleic acids or polypeptides refers to two or more sequences or subsequences that have at least about 80%, about 90, about 95% or higher nucleotide or amino acid residue identity, when compared and aligned for maximum correspondence, as measured using the following sequence comparison method and/or by visual inspection. Such "substantially identical" sequences are typically considered to be homologous. The "substantial identity" can exist over a region of sequence that is at least about 50 residues in length, over a region of at least about 100 residues, or over a region at least about 150 residues, or over the full length of the two sequences to be compared. In case of antibodies, any two antibody sequences can only be aligned in one way, by using the numbering scheme in Kabat (see hereunder). Therefore, for antibodies, percent identity has a unique and well-defined meaning.

Amino acids from the variable regions of the mature heavy and light chains of immunoglobulins are designated Hx and Lx respectively, where x is a number designating the position of an amino acid according to the scheme of Kabat, Sequences of Proteins of Immunological Interest (National Institutes of Health, Bethesda, Md., 1987 and 1991). Kabat lists many amino acid sequences for antibodies for each subgroup, and lists the most commonly occurring amino acid for each residue position in that subgroup to generate a consensus sequence. Kabat uses a method for assigning a residue number to each amino acid in a listed sequence, and this method for assigning residue numbers has become standard in the field. Kabat's scheme is extendible to other antibodies not included in his compendium by aligning the antibody in question with one of the consensus sequences in Kabat by reference to conserved amino acids. The use of the Kabat numbering system readily identifies amino acids at equivalent positions in different antibodies. For example, an amino acid at the L50 position of a human antibody occupies the equivalent position to an amino acid position L50 of a mouse antibody. Likewise, nucleic acids encoding antibody chains are aligned when the amino acid sequences encoded by the respective nucleic acids are aligned according to the Kabat numbering convention.

The phrase "selectively (or specifically) hybridizes to" refers to the binding, duplexing, or hybridizing of a molecule to a particular nucleotide sequence under stringent hybridization conditions when that sequence is present in a complex mixture (e.g., total cellular or library DNA or RNA), wherein the particular nucleotide sequence is detected at least at about 10 times background. In one embodiment, a nucleic acid can be determined to be within the scope of the invention by its ability to hybridize under stringent conditions to a nucleic acid otherwise determined to be within the scope of the invention (such as the exemplary sequences described herein).

The phrase "stringent hybridization conditions" refers to conditions under which a probe will hybridize to its target subsequence, typically in a complex mixture of nucleic acid, but not to other sequences in significant amounts (a positive signal (e.g., identification of a nucleic acid of the invention) is about 10 times background hybridization). Stringent conditions are sequence-dependent and will be different in different circumstances. Longer sequences hybridize specifically at higher temperatures. An extensive guide to the hybridization of nucleic acids is found An extensive guide to the hybridization of nucleic acids is found in e.g., Sambrook, ed., MOLECULAR CLONING: A LABORATORY MANUAL (2ND ED.), Vols. 1-3, Cold Spring Harbor Laboratory, (1989); CURRENT PROTOCOLS IN MOLECULAR BIOLOGY, Ausubel, ed. John Wiley & Sons, Inc., New York (1997); LABORATORY TECHNIQUES IN BIOCHEMISTRY AND MOLECULAR BIOLOGY: HYBRIDIZATION WITH NUCLEIC ACID P ROBES, Part I. Theory and Nucleic Acid Preparation, Tijssen, ed. Elsevier, N.Y. (1993).

Generally, stringent conditions are selected to be about 5-10° C. lower than the thermal melting point (Tm) for the specific sequence at a defined ionic strength pH. The Tm is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide as described in Sambrook (cited below). For high stringency hybridization, a positive signal is at least two times background, preferably 10 times background hybridization. Exemplary high stringency or stringent hybridization conditions include: 50% formamide, 5×SSC and 1% SDS incubated at 42° C. or 5×SSC and 1% SDS incubated at 65° C., with a wash in 0.2×SSC and 0.1% SDS at 65° C. For selective or specific hybridization, a positive signal (e.g., identification of a nucleic acid of the invention) is about 10 times background hybridization. Stringent hybridization conditions that are used to identify nucleic acids within the scope of the invention include, e.g., hybridization in a buffer comprising 50% formamide, 5×SSC, and 1% SDS at 42° C., or hybridization in a buffer comprising 5×SSC and 1% SDS at 65° C., both with a wash of 0.2×SSC and 0.1% SDS at 65° C. In the present invention, genomic DNA or cDNA comprising nucleic acids of the invention can be identified in standard Southern blots under stringent conditions using the nucleic acid sequences disclosed here. Additional stringent conditions for such hybridizations (to identify nucleic acids within the scope of the invention) are those which include hybridization in a buffer of 40% formamide, 1 M NaCl, 1% SDS at 37° C.

However, the selection of a hybridization format is not critical—it is the stringency of the wash conditions that set forth the conditions which determine whether a nucleic acid is within the scope of the invention. Wash conditions used to identify nucleic acids within the scope of the invention include, e.g.: a salt concentration of about 0.02 molar at pH 7 and a temperature of at least about 50° C. or about 55° C. to about 60° C.; or, a salt concentration of about 0.15 M NaCl at 72° C. for about 15 minutes; or, a salt concentration of about 0.2×SSC at a temperature of at least about 50° C. or about 55° C. to about 60° C. for about 15 to about 20 minutes; or, the hybridization complex is washed twice with a solution with a salt concentration of about 2×SSC containing 0.1% SDS at room temperature for 15 minutes and then washed twice by 0. 1×SSC containing 0.1% SDS at 68° C. for 15 minutes; or, equivalent conditions. See Sambrook, Tijssen and Ausubel for a description of SSC buffer and equivalent conditions.

The nucleic acids of the invention are present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. see, e.g., Sambrook, Tijssen and Ausubel. The nucleic acid sequences of the invention and other nucleic acids used to practice this invention, whether RNA, cDNA, genomic DNA, or hybrids thereof, may be isolated from a variety of sources, genetically engineered, amplified, and/or expressed recombinantly. Any recombinant expression system can be used, including, in addition to bacterial, e.g., yeast, insect or mammalian systems. Alternatively, these nucleic acids can be chemically synthesized in vitro. Techniques for the manipulation of nucleic acids, such as, e.g., subcloning into expression vectors, labeling probes, sequencing, and hybridization are well described in the scientific and patent literature, see, e.g., Sambrook, Tijssen and Ausubel. Nucleic acids can be analyzed and quantified by any of a number of general means well known to those of skill in the art. These include, e.g., analytical biochemical methods such as NMR, spectrophotometry, radiography, electrophoresis, capillary electrophoresis, high performance liquid chromatography (HPLC), thin layer chromatography (TLC), and hyperdiffusion chromatography, various immunological methods, such as fluid or gel precipitin reactions, immunodiffusion (single or double), immunoelectrophoresis, radioimmunoassays (RIAs), enzyme-linked immunosorbent assays (ELISAs), immunofluorescent assays, Southern analysis, Northern analysis, dot-blot analysis, gel electrophoresis (e.g., SDS-PAGE), RT-PCR, quantitative PCR, other nucleic acid or target or signal amplification methods, radio labeling, scintillation counting, and affinity chromatography.

The nucleic acid compositions of the present invention, while often in a native sequence (except for modified restriction sites and the like), from either cDNA, genomic or mixtures may be mutated, thereof in accordance with standard techniques to provide gene sequences. For coding sequences, these mutations, may affect amino acid sequence as desired. In particular, DNA sequences substantially homologous to or derived from such sequences described herein are contemplated (where "derived" indicates that a sequence is identical or modified from another sequence).

A nucleic acid is "operably linked" when it is placed into a functional relationship with another nucleic acid sequence. For instance, a promoter or enhancer is operably linked to a coding sequence if it affects the transcription of the sequence. With respect to transcription regulatory sequences, operably linked means that the DNA sequences being linked are contiguous and, where necessary to join two protein coding regions, contiguous and in reading frame. For switch sequences, operably linked indicates that the sequences are capable of effecting switch recombination.

The term "vector" is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "recombinant host cell" (or simply "host cell") refers to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

The term "minilocus transgene" refers to a transgene that comprises a portion of the genomic immunoglobulin locus or on the locus of the selected disease antigen having at least one internal (i.e., not at a terminus of the portion) deletion of a non-essential DNA portion (e.g., intervening sequence; intron or portion thereof) as compared to the naturally-occurring germline Ig locus.

A "label" is a composition detectable by spectroscopic, photochemical, biochemical, immunochemical, or chemical means. For example, useful labels include 32P, fluorescent dyes, electron-dense reagents, enzymes (e.g., as commonly used in an ELISA), biotin, digoxigenin, or haptens and proteins for which antisera or monoclonal antibodies are available (e.g., the polypeptides of the invention can be made detectable, e.g., by incorporating a radiolabel into the peptide, and used to detect antibodies specifically reactive with the peptide).

The term "sorting" in the context of cells as used herein to refers to both physical sorting of the cells, as can be accomplished using, e.g., a fluorescence activated cell sorter, as well as to analysis of cells based on expression of cell surface markers, e.g., FACS analysis in the absence of sorting.

Except when noted, the terms "patient" or "subject" are used interchangeably and refer to a human patients.

The terms "treating" or "treatment" include the administration of the compounds or agents of the present invention to prevent or delay the onset of the symptoms, complications, or biochemical indicia of a disease, alleviating the symptoms or arresting or inhibiting further development of the disease, condition, or disorder (e.g., autoimmune disease). Treatment may be prophylactic (to prevent or delay the onset of the disease, or to prevent the manifestation of clinical or subclinical symptoms thereof) or therapeutic suppression or alleviation of symptoms after the manifestation of the disease.

"Gene delivery vehicle" refers to a recombinant vehicle, such as a recombinant viral vector, a nucleic acid vector (such as plasmid), a naked nucleic acid molecule such as genes, a nucleic acid molecule complexed to a polycationic molecule capable of neutralizing the negative charge on the nucleic acid molecule and condensing the nucleic acid molecule into a compact molecule, a nucleic acid associated with a liposome (Wang et al., PNAS 84: 7851, 1987), a bacterium, and certain eukaryotic cells such as a producer cell, that are capable of delivering a nucleic acid molecule having one or more desirable properties to host cells in an organism.

The term "humanized antibody" as used herein means a human immunoglobulin (a recipient antibody) in which at least part of the residues of complementary-determining region (CDR) is replaced with residues derived from the CDR of a non-human animal antibody (a donor antibody) that has a desired specificity, affinity and capability, such as those of mouse, rat, and rabbit. In some cases, the residue(s) of a Fv framework (FR) in the human immunoglobulin is replaced with residue(s) of the corresponding non-human antibody. The humanized antibody may further comprise a residue that is not found in the recipient antibody or the introduced CDR or framework. These changes are made in order to optimize or improve the properties of the resulting antibody. More detailed information on these changes are referred to Jones et al., 1986; Reichmann et al., 1988; EP-B-239400; Presta, 1992; and EP-B-451216.

A single-chain antibody (also referred to as "scFv") can be prepared by linking a heavy chain V region and a light chain V region of an antibody (for a review of scFv see Pluckthun "The Pharmacology of Monoclonal Antibodies" Vol. 113, eds. Rosenburg and Moore, Springer Verlag, New York, pp. 269-315 (1994)). Methods for preparing single-chain antibodies are known in the art (see, for example, U.S. Pat. Nos. 4,946,778, 5,260,203, 5,091,513, and 5,455,030). In such scFvs, the heavy chain V region and the light chain V region are linked together via a linker, preferably, a polypeptide linker (Huston, 1988). The heavy chain V region and the light chain V region in a scFv may be derived from the same antibody, or from different antibodies.

An "Fv" fragment is the smallest antibody fragment, and contains a complete antigen recognition site and a binding site. This region is a dimer (VH-VL dimer) wherein the variable regions of each of the heavy chain and light chain are strongly connected by a noncovalent bond. The three CDRs of each of the variable regions interact with each other to form an antigen-binding site on the surface of the VH-VL dimer. In other words, a total of six CDRs from the heavy and light chains function together as an antibody's antigen-binding site. However, a variable region (or a half Fv, which contains only three antigen-specific CDRs) alone is also known to be able to recognize and bind to an antigen, although its affinity is lower than the affinity of the entire binding site. Thus, a preferred antibody fragment of the present invention is an Fv fragment, but is not limited thereto.

Such an antibody fragment may be a polypeptide which comprises an antibody fragment of heavy or light chain CDRs which are conserved, and which can recognize and bind its antigen.

A Fab fragment (also referred to as F(ab)) also contains a light chain constant region and heavy chain constant region (CH1). For example, papain digestion of an antibody produces the two kinds of fragments: an antigen-binding fragment, called a Fab fragment, containing the variable regions of a heavy chain and light chain, which serve as a single antigen-binding domain; and the remaining portion, which is called an "Fc" because it is readily crystallized. A Fab' fragment is different from a Fab fragment in that a Fab' fragment also has several residues derived from the carboxyl terminus of a heavy chain CH1 region, which contains one or more cysteine residues from the hinge region of an antibody.

A Fab' fragment is, however, structurally equivalent to Fab in that both are antigen-binding fragments which comprise the variable regions of a heavy chain and light chain, which serve as a single antigen-binding domain. Herein, an antigen-binding fragment comprising the variable regions of a heavy chain and light chain which serve as a single antigen-binding domain, and which is equivalent to that obtained by papain digestion, is referred to as a "Fab-like antibody", even when it is not identical to an antibody fragment produced by protease digestion. Fab'-SH is Fab' with one or more cysteine residues having free thiol groups in its constant region. A F(ab') fragment is produced by cleaving the disulfide bond between the cysteine residues in the hinge region of F(ab')2. Other chemically crosslinked antibody fragments are also known to those skilled in the art.

Pepsin digestion of an antibody yields two fragments; one is a F(ab')2fragment which comprises two antigen-binding domains and can cross-react with antigens, and the other is the remaining fragment (referred to as pFc'). Herein, an antibody fragment equivalent to that obtained by pepsin digestion is referred to as a "F(ab')2-like antibody" when it comprises two antigen-binding domains and can crossreact with antigens. Such antibody fragments can also be produced, for example, by genetic engineering. Such antibody fragments can also be isolated, for example, from the antibody phage library described above. Alternatively, F(ab')2-SH fragments can be recovered directly from hosts, such as E. coli, and then allowed to form F(ab')2 fragments by chemical crosslinking (Carter et al., Bio/Technology 10:163-167 (1992)).

Single domain antibodies can be engineered into antibody like fragments. Single domain antibodies are antibodies whose complementary determining regions are part of a single domain polypeptide. Examples include, but are not limited to, heavy chain antibodies, antibodies naturally devoid of light chains, single domain antibodies derived from conventional 4-chain antibodies, engineered antibodies and single domain scaffolds other than those derived from antibodies. Single domain antibodies may be any of the art, or any future single domain antibodies. Single domain antibodies may be derived from any species including, but not limited to mouse, human, camel, llama, goat, rabbit, bovine. According to one aspect of the invention, a single domain antibody as used herein is a naturally occurring single domain antibody known as heavy chain antibody devoid of light chains. Such single domain antibodies are disclosed in WO 9404678 for example. For clarity reasons, this variable domain derived from a heavy chain antibody naturally devoid of light chain is known herein as a VHH or nanobody to distinguish it from the conventional VH of four chain immunoglobulins. Such a VHH molecule can be derived from antibodies raised in Camelidae species, for example in camel, llama, dromedary, alpaca and guanaco or Elasmobranchii species for instance skates, rays (batoidea), and sharks (selachii). Other species besides Camelidae may produce heavy chain antibodies naturally devoid of light chain; such VHHs are within the scope of the invention. The single-chain polypeptide may be produced by various methods well known in the art such as genetic engineering technique and chemical synthesis. The genetic engineering technique includes constructing a replicable cloning vector or expression vector, transforming the host cell with the vector, culturing the transformed host cell to express the nucleic acid in it, collecting and purifying the single-chain polypeptide. The vector usually comprises the nucleic acid encoding one of the two single-chain polypeptides constituting the diabody-type bispecific antibody according to the present invention. In such case, the resulting two kinds of the vectors are preferably introduced into the same host cell. Alternatively, the two kinds of nucleic acid encoding the different single-chin polypeptide from each other may be comprised in the same vector.

The term "replicable expression vector" or "expression vector" as used herein refers to a piece of DNA (usually double-stranded) that may comprise a fragment of a foreign DNA fragment inserted therein. The foreign DNA is also defined as a "heterologous DNA", which can not be found naturally in a host cell in interest. The vector is used to carry or convey the foreign or heterologous DNA into an appropriate host cell. Once the vector is introduced into the host cell, it may be replicated independently from a chromosomal DNA of the host cell to produce copies of the vector and foreign DNA inserted therein. The vector also comprises elements essential for translating the foreign DNA into a polypeptide so that the polypeptide molecules encoded by the foreign DNA will be synthesized very quickly.

The above vector means a DNA construct comprising an appropriate control sequence and DNA sequence that are operably linked together (i.e., linked together so that the foreign DNA can be expressed). The control sequence includes a promoter for transcription, an optional operator sequence to regulate the transcription, a sequence encoding an appropriate mRNA ribosome-biding site, an enhancer, a polyadenylation sequence, and a sequence controlling the termination of transcription and translation. The vector may further comprise various sequences known in the art, such as a restriction enzyme cleaving site, a marker gene (selection gene) such as a drug-resistant gene, a signal sequence, and a leader sequence. These sequences and elements may be optionally selected by those skilled in the art depending on the kinds of the foreign DNA and host cell, and conditions of culture medium.

The vector may be in any form such as a plasmid, phage particle, or just simply genomic insert. Once the appropriate host cell is transformed with the vector, the vector will be replicated or function independently from the genome of the host cell, or the vector will alternatively be integrated into the genome of the cell.

Any cell known in the art may be used as the host cell, for example, there may be mentioned procaryotic cells such as including *E. coli*, eucaryotic cells such as mammalian cells such Chinese hamster ovary (CHO) cell and human cells, yeast, and insect cells.

Although the single-chain polypeptide obtained by the expression in the host cell is usually secreted and collected from the culture medium, it may be also collected from cell lysate when it is directly expressed without a secretion signal. In case the single-chain polypeptide has a membrane-binding property, it may be released from the membrane with an appropriate surfactant such as Triton-X100.

Purification of the polypeptide may be carried out by any method known to those skilled in the art such as centrifugation, hydroxyapatite chromatography, gel electrophoresis, dialysis, separation on ion-exchange chromatography, ethanol precipitation, reverse phase HPLC, silica chromatography, heparin-sepharose chromatography, anion- or cation-resin chromatography such as polyaspartic acid column, chromato-focusing, SDS-PAGE, precipitation with ammonium sulfate, and affinity chromatography. The affinity chromatography, which utilizes affinity with a peptide tag of the single-chain polypeptide, is one of the preferred purification techniques with a high efficiency.

Since the collected single-chain polypeptide may be often included in an insoluble fraction, the polypeptide is preferably purified after being solubilized and denatured. The solubilization treatment may be carried out with the use of any agent known in the art, including alcohol such ethanol, a dissolving agent such as guanidine hydrochloride and urea.

The antibody like fragments according to the present invention is produced by assembling the single-chain polypeptides, eventually on a scaffold, and separating and collecting the thus formed antibody like fragments.

Assembling treatment brings the single-chain polypeptide back in an appropriate spatial arrangement in which a desired biological activity is shown. Thus, since this treatment brings the polypeptides or domains back into an assembling state, it may be considered "re-assembling." It may be also called "re-constitution" or "refolding" in view of gaining the desired biological activity.

The assembling treatment may be carried out by any method known in the art preferably by gradually lowering the concentration of a denaturing agent such as guanidine hydrochloride in a solution comprising the single-chain polypeptide by means of dialysis. During these processes, an anti-coagulant or oxidizing agent may be optionally added in a reaction system in order to promote the oxidation. The separation and collection of the formed antibody like fragment may be done by any method known in the art as well.

VHHs, according to the present invention, and as known to the skilled addressee are heavy chain variable domains derived from immunoglobulins naturally devoid of light chains such as those derived from Camelidae as described in WO9404678 (and referred to hereinafter as VHH domains or nanobodies). VHH molecules are about 10× smaller than IgG molecules. They are single polypeptides and very stable, resisting extreme pH and temperature conditions. Moreover, they are resistant to the action of proteases which is not the case for conventional antibodies. Furthermore, in vitro expression of VHHs produces high yield, properly folded functional VHHs. In addition, antibodies generated in Camelids will recognize epitopes other than those recognised by antibodies generated in vitro through the use of antibody libraries or via immunisation of mammals other than Camelids or Elasmobranchii species (WO 9749805). As such, anti-albumin VHH's may interact in a more efficient way with serum albumin which is known to be a carrier protein. As a carrier protein some of the epitopes of serum albumin may be inaccessible by bound proteins, peptides and small chemical compounds. Since VHH's are known to bind into 'unusual' or non-conventional epitopes such as cavities (WO9749805), the affinity of such VHH's to circulating albumin may be increased.

In one embodiment, the antibody or antibody fragment of present invention comprises at least one CDR having an amino acid sequence selected from the group consisting of SEQ ID NO. 9 to SEQ ID NO. 14, or an amino acid sequence which has at least 80% identity to an amino acid sequence selected from the group consisting of SEQ ID NO. 9 to SEQ ID NO. 14.

In an alternative embodiment, the antibody or antibody fragment comprises at least one CDR having an amino acid sequence selected from the group consisting of SEQ ID NO. 9 to SEQ ID NO. 14, or an amino acid sequence which has at least 80, 81, 82, 83, 84, 85, 86, 87, 88, 89, 90, 91, 92, 93, 94, 95, 96, 97, 98, 99, or 100% identity to an amino acid sequence selected from the group consisting of SEQ ID NO. 9 to SEQ ID NO. 14.

In a particular embodiment, the antibody or antibody fragment comprises at least one CDR triplet selected from the group consisting of a CDR triplet H1/H2/H3; and
a CDR triplet L1/L2/L3;

wherein H1 has an amino acid sequence chosen from SEQ ID NO. 12 or an amino acid sequence which has at least 80% identity to SEQ ID NO. 12, H2 has an amino acid sequence chosen from SEQ ID NO. 13 or an amino acid sequence which has at least 80% identity to SEQ ID NO. 13, H3 has an amino acid sequence chosen from SEQ ID NO. 14 or an amino acid sequence which has at least 80% identity to SEQ ID NO. 14, L1 has an amino acid sequence chosen from SEQ ID NO. 9 or an amino acid sequence which has at least 80% identity to SEQ ID NO. 9, L2 has an amino acid sequence chosen from SEQ ID NO. 10 or an amino acid sequence which has at least 80% identity to SEQ ID NO. 10, and L3 has an amino acid sequence chosen from SEQ ID NO. 11 or an amino acid sequence which has at least 80% identity to SEQ ID NO. 11.

In a particular embodiment, the antibody or antibody fragment comprises at least one CDR triplet selected from the group consisting of
a CDR triplet H1/H2/H3; and
a CDR triplet L1/L2/L3;

wherein H1 has an amino acid sequence which has at least 85% identity to SEQ ID NO. 12, H2 has an amino acid sequence which has at least 85% identity to SEQ ID NO. 13, H3 has an amino acid sequence which has at least 85% identity to SEQ ID NO. 14, L1 has an amino acid sequence which has at least 85% identity to SEQ ID NO. 9, L2 has an amino acid sequence which has at least 85% identity to SEQ ID NO. 10, and L3 has an amino acid sequence which has at least 85% identity to SEQ ID NO. 11.

In a particular embodiment, the antibody or antibody fragment comprises at least one CDR triplet selected from the group consisting of
a CDR triplet H1/H2/H3; and
a CDR triplet L1/L2/L3;

wherein H1 has an amino acid sequence which has at least 90% identity to SEQ ID NO. 12, H2 has an amino acid sequence which has at least 90% identity to SEQ ID NO. 13, H3 has an amino acid sequence which has at least 90% identity to SEQ ID NO. 14, L1 has an amino acid sequence which has at least 90% identity to SEQ ID NO. 9, L2 has an amino acid sequence which has at least 90% identity to SEQ ID NO. 10, and L3 has an amino acid sequence which has at least 90% identity to SEQ ID NO. 11.

In a particular embodiment, the antibody or antibody fragment comprises at least one CDR triplet selected from the group consisting of
a CDR triplet H1/H2/H3; and
a CDR triplet L1/L2/L3;

wherein H1 has an amino acid sequence which has at least 95% identity to SEQ ID NO. 12, H2 has an amino acid sequence which has at least 95% identity to SEQ ID NO. 13, H3 has an amino acid sequence which has at least 95% identity to SEQ ID NO. 14, L1 has an amino acid sequence which has at least 95% identity to SEQ ID NO. 9, L2 has an amino acid sequence which has at least 95% identity to SEQ ID NO. 10, and L3 has an amino acid sequence which has at least 95% identity to SEQ ID NO. 11.

In a particular embodiment, the antibody or antibody fragment comprises at least one CDR triplet selected from the group consisting of
a CDR triplet H1/H2/H3; and
a CDR triplet L1/L2/L3;

wherein H1 has an amino acid sequence which has at least 98% identity to SEQ ID NO. 12, H2 has an amino acid sequence which has at least 98% identity to SEQ ID NO. 13, H3 has an amino acid sequence which has at least 98% identity to SEQ ID NO. 14, L1 has an amino acid sequence which has at least 98% identity to SEQ ID NO. 9, L2 has an amino acid sequence which has at least 98% identity to SEQ ID NO. 10, and L3 has an amino acid sequence which has at least 98% identity to SEQ ID NO. 11.

In a particular embodiment, the antibody or antibody fragment comprises at least one variable domain having an amino acid sequence selected from the group consisting of SEQ ID NO. 15, 16, 17 and 18 or an amino acid sequence which has at least 80% identity to an amino acid sequence selected from the group consisting of SEQ ID NO. 15, 16, 17 and 18.

In a particular embodiment, the antibody or antibody fragment comprises a heavy chain variable region having an amino acid sequence of SEQ ID NO. 15, or an amino acid sequence which has at least 80% identity to an amino acid sequence of SEQ ID NO. 15.

In a particular embodiment, the antibody or antibody fragment comprises a light chain variable region having an amino acid sequence of SEQ ID NO. 16, or an amino acid sequence which has at least 80% identity to an amino acid sequence of SEQ ID NO. 16.

In a particular embodiment, the antibody or antibody fragment comprises a heavy chain variable region having an amino acid sequence of SEQ ID NO. 15, or an amino acid sequence which has at least 90% identity to an amino acid sequence of SEQ ID NO. 15.

In a particular embodiment, the antibody or antibody fragment comprises a light chain variable region having an amino acid sequence of SEQ ID NO. 16, or an amino acid sequence which has at least 90% identity to an amino acid sequence of SEQ ID NO. 16.

In a particular embodiment, the antibody or antibody fragment comprises a heavy chain variable region having an amino acid sequence of SEQ ID NO. 15, or an amino acid sequence which has at least 95% identity to an amino acid sequence of SEQ ID NO. 15.

In a particular embodiment, the antibody or antibody fragment comprises a light chain variable region having an amino acid sequence of SEQ ID NO. 16, or an amino acid sequence which has at least 95% identity to an amino acid sequence of SEQ ID NO. 16.

In a particular embodiment, the antibody or antibody fragment comprises a heavy chain variable region having an amino acid sequence of SEQ ID NO. 15, or an amino acid sequence which has at least 98% identity to an amino acid sequence of SEQ ID NO. 15.

In a particular embodiment, the antibody or antibody fragment comprises a light chain variable region having an amino acid sequence of SEQ ID NO. 16, or an amino acid sequence which has at least 98% identity to an amino acid sequence of SEQ ID NO. 16.

In an alternative embodiment, the antibody or antibody fragment comprises at least one variable domain having an amino acid sequence selected from the group consisting of SEQ ID NO. 15 and 16, or an amino acid sequence which has at least 80, 81, 82, 83, 84, 85, 86, 87, 88, 89, 90, 91, 92, 93, 94, 95, 96, 97, 98, 99, or 100% identity to an amino acid sequence selected from the group consisting of SEQ ID NO. 15 and 16.

In one embodiment, the antibody or antibody fragment comprises at least one CDR having an amino acid sequence selected from the group consisting of SEQ ID NO. 9 to SEQ ID NO. 14, or an amino acid sequence which has at least 80% identity to an amino acid sequence selected from the group consisting of SEQ ID NO. 9 to SEQ ID NO. 14, characterized in that it preferentially binds to phosphorylated tau aggregates.

In an alternative embodiment, the antibody or antibody fragment comprises at least one CDR having an amino acid sequence selected from the group consisting of SEQ ID NO. 9 to SEQ ID NO. 14, or an amino acid sequence which has at least 80, 81, 82, 83, 84, 85, 86, 87, 88, 89, 90, 91, 92, 93, 94, 95, 96, 97, 98, 99, or 100% identity to an amino acid sequence selected from the group consisting of SEQ ID NO. 9 to SEQ ID NO. 14, characterized in that it preferentially binds to phosphorylated tau aggregates.

In a particular embodiment, the antibody or antibody fragment comprises at least one CDR triplet selected from the group consisting of
  a CDR triplet H1/H2/H3; and
  a CDR triplet L1/L2/L3;
  wherein H1 has an amino acid sequence chosen from SEQ ID NO. 12 or an amino acid sequence which has at least 80% identity to SEQ ID NO. 12, H2 has an amino acid sequence chosen from SEQ ID NO. 13 or an amino acid sequence which has at least 80% identity to SEQ ID NO. 13, H3 has an amino acid sequence chosen from SEQ ID NO. 14 or an amino acid sequence which has at least 80% identity to SEQ ID NO. 14, L1 has an amino acid sequence chosen from SEQ ID NO. 9 or an amino acid sequence which has at least 80% identity to SEQ ID NO. 9, L2 has an amino acid sequence chosen from SEQ ID NO. 10 or an amino acid sequence which has at least 80% identity to SEQ ID NO. 10, and L3 has an amino acid sequence chosen from SEQ ID NO. 11 or an amino acid sequence which has at least 80% identity to SEQ ID NO. 11, characterized in that it preferentially binds to phosphorylated tau aggregates.

In a particular embodiment, the antibody or antibody fragment comprises at least one CDR triplet selected from the group consisting of
  a CDR triplet H1/H2/H3; and
  a CDR triplet L1/L2/L3;
  wherein H1 has an amino acid sequence which has at least 85% identity to SEQ ID NO. 12, H2 has an amino acid sequence which has at least 85% identity to SEQ ID NO. 13, H3 has an amino acid sequence which has at least 85% identity to SEQ ID NO. 14, L1 has an amino acid sequence which has at least 85% identity to SEQ ID NO. 9, L2 has an amino acid sequence which has at least 85% identity to SEQ ID NO. 10, and L3 has an amino acid sequence which has at least 85% identity to SEQ ID NO. 11, characterized in that it preferentially binds to phosphorylated tau aggregates.

In a particular embodiment, the antibody or antibody fragment comprises at least one CDR triplet selected from the group consisting of
  a CDR triplet H1/H2/H3; and
  a CDR triplet L1/L2/L3;
  wherein H1 has an amino acid sequence which has at least 90% identity to SEQ ID NO. 12, H2 has an amino acid sequence which has at least 90% identity to SEQ ID NO. 13, H3 has an amino acid sequence which has at least 90% identity to SEQ ID NO. 14, L1 has an amino acid sequence which has at least 90% identity to SEQ ID NO. 9, L2 has an amino acid sequence which has at least 90% identity to SEQ ID NO. 10, and L3 has an amino acid sequence which has at least 90% identity to SEQ ID NO. 11, characterized in that it preferentially binds to phosphorylated tau aggregates.

In a particular embodiment, the antibody or antibody fragment comprises at least one CDR triplet selected from the group consisting of
  a CDR triplet H1/H2/H3; and
  a CDR triplet L1/L2/L3;
  wherein H1 has an amino acid sequence which has at least 95% identity to SEQ ID NO. 12, H2 has an amino acid sequence which has at least 95% identity to SEQ ID NO. 13, H3 has an amino acid sequence which has at least 95% identity to SEQ ID NO. 14, L1 has an amino acid sequence which has at least 95% identity to SEQ ID NO. 9, L2 has an amino acid sequence which has at least 95% identity to SEQ ID NO. 10, and L3 has an amino acid sequence which has at least 95% identity to SEQ ID NO. 11, characterized in that it preferentially binds to phosphorylated tau aggregates.

In a particular embodiment, the antibody or antibody fragment comprises at least one CDR triplet selected from the group consisting of
  a CDR triplet H1/H2/H3; and
  a CDR triplet L1/L2/L3;
  wherein H1 has an amino acid sequence which has at least 98% identity to SEQ ID NO. 12, H2 has an amino acid sequence which has at least 98% identity to SEQ ID NO. 13, H3 has an amino acid sequence which has at least 98% identity to SEQ ID NO. 14, L1 has an amino acid sequence which has at least 98% identity to SEQ ID NO. 9, L2 has an amino acid sequence which has at least 98% identity to SEQ ID NO. 10, and L3 has an amino acid sequence which has at least 98% identity to SEQ ID NO. 11, characterized in that it preferentially binds to phosphorylated tau aggregates.

In a particular embodiment, the antibody or antibody fragment comprises at least one variable domain having an amino acid sequence selected from the group consisting of SEQ ID NO. 15, 16, 17 and 18 or an amino acid sequence which has at least 80% identity to an amino acid sequence selected from the group consisting of SEQ ID NO. 15, 16, 17 and 18, characterized in that it preferentially binds to phosphorylated tau aggregates.

In a particular embodiment, the antibody or antibody fragment comprises a heavy chain variable region having an amino acid sequence of SEQ ID NO. 15, or an amino acid sequence which has at least 80% identity to an amino acid sequence of SEQ ID NO. 15, characterized in that it preferentially binds to phosphorylated tau aggregates.

In a particular embodiment, the antibody or antibody fragment comprises a light chain variable region having an amino acid sequence of SEQ ID NO. 16, or an amino acid sequence which has at least 80% identity to an amino acid sequence of SEQ ID NO. 16, characterized in that it preferentially binds to phosphorylated tau aggregates.

In a particular embodiment, the antibody or antibody fragment comprises a heavy chain variable region having an amino acid sequence of SEQ ID NO. 15, or an amino acid sequence which has at least 90% identity to an amino acid sequence of SEQ ID NO. 15, characterized in that it preferentially binds to phosphorylated tau aggregates.

In a particular embodiment, the antibody or antibody fragment comprises a light chain variable region having an amino acid sequence of SEQ ID NO. 16, or an amino acid sequence which has at least 90% identity to an amino acid sequence of SEQ ID NO. 16, characterized in that it preferentially binds to phosphorylated tau aggregates.

In a particular embodiment, the antibody or antibody fragment comprises a heavy chain variable region having an amino acid sequence of SEQ ID NO. 15, or an amino acid sequence which has at least 95% identity to an amino acid sequence of SEQ ID NO. 15, characterized in that it preferentially binds to phosphorylated tau aggregates.

In a particular embodiment, the antibody or antibody fragment comprises a light chain variable region having an amino acid sequence of SEQ ID NO. 16, or an amino acid sequence which has at least 95% identity to an amino acid sequence of SEQ ID NO. 16, characterized in that it preferentially binds to phosphorylated tau aggregates.

In a particular embodiment, the antibody or antibody fragment comprises a heavy chain variable region having an amino acid sequence of SEQ ID NO. 15, or an amino acid sequence which has at least 98% identity to an amino acid sequence of SEQ ID NO. 15, characterized in that it preferentially binds to phosphorylated tau aggregates.

In a particular embodiment, the antibody or antibody fragment comprises a light chain variable region having an amino acid sequence of SEQ ID NO. 16, or an amino acid sequence which has at least 98% identity to an amino acid sequence of SEQ ID NO. 16, characterized in that it preferentially binds to phosphorylated tau aggregates.

In an alternative embodiment, the antibody or antibody fragment comprises at least one variable domain having an amino acid sequence selected from the group consisting of SEQ ID NO. 15 and 16, or an amino acid sequence which has at least 80, 81, 82, 83, 84, 85, 86, 87, 88, 89, 90, 91, 92, 93, 94, 95, 96, 97, 98, 99, or 100% identity to an amino acid sequence selected from the group consisting of SEQ ID NO. 15 and 16, characterized in that it preferentially binds to phosphorylated tau aggregates.

In one embodiment, the antibody or antibody fragment comprises at least one CDR having an amino acid sequence selected from the group consisting of SEQ ID NO. 19 to SEQ ID NO. 24, or an amino acid sequence which has at least 80% identity to an amino acid sequence selected from the group consisting of SEQ ID NO. 19 to SEQ ID NO. 24.

In an alternative embodiment, the antibody or antibody fragment comprises at least one CDR having an amino acid sequence selected from the group consisting of SEQ ID NO. 19 to SEQ ID NO. 24, or an amino acid sequence which has at least 80, 81, 82, 83, 84, 85, 86, 87, 88, 89, 90, 91, 92, 93, 94, 95, 96, 97, 98, 99, or 100% identity to an amino acid sequence selected from the group consisting of SEQ ID NO. 19 to SEQ ID NO. 24.

In a particular embodiment, the antibody or antibody fragment comprises at least one CDR triplet selected from the group consisting of
  a CDR triplet H1/H2/H3; and
  a CDR triplet L1/L2/L3;
  wherein H1 has an amino acid sequence chosen from SEQ ID NO. 19 or an amino acid sequence which has at least 80% identity to SEQ ID NO. 19, H2 has an amino acid sequence chosen from SEQ ID NO. 20 or an amino acid sequence which has at least 80% identity to SEQ ID NO. 20, H3 has an amino acid sequence chosen from SEQ ID NO. 21 or an amino acid sequence which has at least 80% identity to SEQ ID NO. 21, L1 has an amino acid sequence chosen from SEQ ID NO. 22 or an amino acid sequence which has at least 80% identity to SEQ ID NO. 22, L2 has an amino acid sequence chosen from SEQ ID NO. 23 or an amino acid sequence which has at least 80% identity to SEQ ID NO. 23, and L3 has an amino acid sequence chosen from SEQ ID NO. 24 or an amino acid sequence which has at least 80% identity to SEQ ID NO. 24.

In a particular embodiment, the antibody or antibody fragment comprises at least one CDR triplet selected from the group consisting of
  a CDR triplet H1/H2/H3; and
  a CDR triplet L1/L2/L3;
  wherein H1 has an amino acid sequence which has at least 85% identity to SEQ ID NO. 19, H2 has an amino acid sequence which has at least 85% identity to SEQ ID NO. 20, H3 has an amino acid sequence which has at least 85% identity to SEQ ID NO. 21, L1 has an amino acid sequence which has at least 85% identity to SEQ ID NO. 22, L2 has an amino acid sequence which has at least 85% identity to SEQ ID NO. 23, and L3 has an amino acid sequence which has at least 85% identity to SEQ ID NO. 24.

In a particular embodiment, the antibody or antibody fragment comprises at least one CDR triplet selected from the group consisting of
  a CDR triplet H1/H2/H3; and
  a CDR triplet L1/L2/L3;
  wherein H1 has an amino acid sequence which has at least 90% identity to SEQ ID NO. 19, H2 has an amino acid sequence which has at least 90% identity to SEQ ID NO. 20, H3 has an amino acid sequence which has at least 90% identity to SEQ ID NO. 21, L1 has an amino acid sequence which has at least 90% identity to SEQ ID NO. 22, L2 has an amino acid sequence which has at least 90% identity to SEQ ID NO. 23, and L3 has an amino acid sequence which has at least 90% identity to SEQ ID NO. 24.

In a particular embodiment, the antibody or antibody fragment comprises at least one CDR triplet selected from the group consisting of
  a CDR triplet H1/H2/H3; and
  a CDR triplet L1/L2/L3;
  wherein H1 has an amino acid sequence which has at least 95% identity to SEQ ID NO. 19, H2 has an amino acid sequence which has at least 95% identity to SEQ ID NO. 20, H3 has an amino acid sequence which has at least 95% identity to SEQ ID NO. 21, L1 has an amino acid sequence which has at least 95% identity to SEQ ID NO. 22, L2 has an amino acid sequence which has at least 95% identity to SEQ ID NO. 23, and L3 has an amino acid sequence which has at least 95% identity to SEQ ID NO. 24.

In a particular embodiment, the antibody or antibody fragment comprises at least one CDR triplet selected from the group consisting of
  a CDR triplet H1/H2/H3; and
  a CDR triplet L1/L2/L3;
  wherein H1 has an amino acid sequence which has at least 98% identity to SEQ ID NO. 19, H2 has an amino acid sequence which has at least 98% identity to SEQ ID NO. 20, H3 has an amino acid sequence which has at least 98% identity to SEQ ID NO. 21, L1 has an amino acid sequence which has at least 98% identity to SEQ ID NO. 22, L2 has an amino acid sequence which has at least 98% identity to SEQ ID NO. 23, and L3 has an amino acid sequence which has at least 98% identity to SEQ ID NO. 24.

In a particular embodiment, the antibody or antibody fragment comprises at least one variable domain having an amino acid sequence selected from the group consisting of SEQ ID NO. 25 and 26 or an amino acid sequence which has at least 80% identity to an amino acid sequence selected from the group consisting of SEQ ID NO. 25 and 26.

In a particular embodiment, the antibody or antibody fragment comprises a heavy chain variable region having an amino acid sequence of SEQ ID NO. 25, or an amino acid sequence which has at least 80% identity to an amino acid sequence of SEQ ID NO. 25.

In a particular embodiment, the antibody or antibody fragment comprises a light chain variable region having an amino acid sequence of SEQ ID NO. 26, or an amino acid sequence which has at least 80% identity to an amino acid sequence of SEQ ID NO. 26.

In a particular embodiment, the antibody or antibody fragment comprises a heavy chain variable region having an amino acid sequence of SEQ ID NO. 25, or an amino acid sequence which has at least 90% identity to an amino acid sequence of SEQ ID NO. 25.

In a particular embodiment, the antibody or antibody fragment comprises a light chain variable region having an amino acid sequence of SEQ ID NO. 26, or an amino acid sequence which has at least 90% identity to an amino acid sequence of SEQ ID NO. 26.

In a particular embodiment, the antibody or antibody fragment comprises a heavy chain variable region having an amino acid sequence of SEQ ID NO. 25, or an amino acid sequence which has at least 95% identity to an amino acid sequence of SEQ ID NO. 25.

In a particular embodiment, the antibody or antibody fragment comprises a light chain variable region having an amino acid sequence of SEQ ID NO. 26, or an amino acid sequence which has at least 95% identity to an amino acid sequence of SEQ ID NO. 26.

In a particular embodiment, the antibody or antibody fragment comprises a heavy chain variable region having an amino acid sequence of SEQ ID NO. 25, or an amino acid sequence which has at least 98% identity to an amino acid sequence of SEQ ID NO. 25.

In a particular embodiment, the antibody or antibody fragment comprises a light chain variable region having an amino acid sequence of SEQ ID NO. 26, or an amino acid sequence which has at least 98% identity to an amino acid sequence of SEQ ID NO. 26.

In an alternative embodiment, the antibody or antibody fragment comprises at least one variable domain having an amino acid sequence selected from the group consisting of SEQ ID NO. 25 and 26, or an amino acid sequence which has at least 80, 81, 82, 83, 84, 85, 86, 87, 88, 89, 90, 91, 92, 93, 94, 95, 96, 97, 98, 99, or 100% identity to an amino acid sequence selected from the group consisting of SEQ ID NO. 25 and 26.

In one embodiment, the antibody or antibody fragment comprises at least one CDR having an amino acid sequence selected from the group consisting of SEQ ID NO. 19 to SEQ ID NO. 24, or an amino acid sequence which has at least 80% identity to an amino acid sequence selected from the group consisting of SEQ ID NO. 19 to SEQ ID NO. 24 and it is characterized in that it recognizes high molecular weight tau complexes and epitope 16-GTYGLGDRK-24 (SEQ ID NO. 27) for instance of human Tau isotope hTAU40 (Such antibody can hereafter be referred to as or ADx215). This has further been characterized that it has a much higher affinity (reduced exposure time). This can be characterized that said the antibody or fragment has a binding affinity for the SEQ ID NO. 27 epitope or the SEQ ID NO. 27 epitope on a (high molecular weight tau complex) characterized by a Kd of 30 nM or less, preferably at a Kd of 10 nM or less, and yet more preferably at a Kd of less than 3 nM. This can be characterized that said antibody or fragment has a binding affinity for the SEQ ID NO 27 epitope or the SEQ ID NO. 27 epitope on a (high molecular weight tau complex) characterized by a Kd of a value between 10 nM to 1 nM.

In an alternative embodiment, the antibody or antibody fragment comprises at least one CDR having an amino acid sequence selected from the group consisting of SEQ ID NO. 19 to SEQ ID NO. 24, or an amino acid sequence which has at least 80, 81, 82, 83, 84, 85, 86, 87, 88, 89, 90, 91, 92, 93, 94, 95, 96, 97, 98, 99, or 100% identity to an amino acid sequence selected from the group consisting of SEQ ID NO. 19 to SEQ ID NO. 24 and it is characterized in that it recognizes high molecular weight tau complexes and epitope 16-GTYGLGDRK-24 (SEQ ID NO. 27) for instance of human Tau isotope hTAU40 (Such antibody can hereafter be referred to as or ADx215). This has further been characterized that it has a much higher affinity (reduced exposure time). This can be characterized that said the antibody or fragment has a binding affinity for the SEQ ID NO. 27 epitope or the SEQ ID NO. 27 epitope on a high molecular weight tau complex characterized by a Kd of 30 nM or less, preferably at a Kd of 10 nM or less, and yet more preferably at a Kd of less than 3 nM. This can be characterized that said the antibody or fragment has a binding affinity for the SEQ ID NO. 27 epitope or the SEQ ID NO. 27 epitope on a high molecular weight tau complex characterized by a Kd of a value between 10 nM to 1 nM.

In a particular embodiment, the antibody or antibody fragment comprises at least one CDR triplet selected from the group consisting of
a CDR triplet H1/H2/H3; and
a CDR triplet L1/L2/L3;
wherein H1 has an amino acid sequence chosen from SEQ ID NO. 19 or an amino acid sequence which has at least 80% identity to SEQ ID NO. 19, H2 has an amino acid sequence chosen from SEQ ID NO. 20 or an amino acid sequence which has at least 80% identity to SEQ ID NO. 20, H3 has an amino acid sequence chosen from SEQ ID NO. 21 or an amino acid sequence which has at least 80% identity to SEQ ID NO. 21, L1 has an amino acid sequence chosen from SEQ ID NO. 22 or an amino acid sequence which has at least 80% identity to SEQ ID NO. 22, L2 has an amino acid sequence chosen from SEQ ID NO. 23 or an amino acid sequence which has at least 80% identity to SEQ ID NO. 23, and L3 has an amino acid sequence chosen from SEQ ID NO. 24 or an amino acid sequence which has at least 80% identity to SEQ ID NO. 24 and it is characterized in that it recognizes high molecular weight tau complexes and epitope 16-GTYGLGDRK-24 (SEQ ID NO. 27) for instance of human Tau isotope hTAU40 (Such antibody can hereafter be referred to as or ADx215). This has further been characterized that it has a much higher affinity (reduced exposure time). This can be characterized that said the antibody or fragment has a binding affinity for the SEQ ID NO. 27 epitope or the SEQ ID NO. 27 epitope on a high molecular weight tau complex characterized by a Kd of 30 nM or less, preferably at a Kd of 10 nM or less, and yet more preferably at a Kd of less than 3 nM. This can be characterized that said the antibody or fragment has a binding affinity for the SEQ ID NO. 27 epitope or the SEQ ID NO. 27 epitope on a (high molecular weight tau complex) characterized by a Kd of a value between 10 nM to 1 nM.

In a particular embodiment, the antibody or antibody fragment comprises at least one CDR triplet selected from the group consisting of
a CDR triplet H1/H2/H3; and
a CDR triplet L1/L2/L3;
wherein H1 has an amino acid sequence which has at least 85% identity to SEQ ID NO. 19, H2 has an amino acid sequence which has at least 85% identity to SEQ ID NO. 20, H3 has an amino acid sequence which has at least 85% identity to SEQ ID NO. 21, L1 has an amino acid sequence which has at least 85% identity to SEQ ID NO. 22, L2 has an amino acid sequence which has at least 85% identity to SEQ ID NO. 23, and L3 has an amino acid sequence which has at least 85% identity to SEQ ID NO. 24 and it is characterized in that it recognizes high molecular weight tau complexes and epitope 16-GTYGLGDRK-24 (SEQ ID NO. 27) for instance of human Tau isotope hTAU40 (Such antibody can hereafter be referred to as or ADx215). This has further been characterized that it has a much higher affinity (reduced exposure time). This can be characterized that said the antibody or fragment has a binding affinity for the SEQ ID NO. 27 epitope or the SEQ ID NO. 27 epitope on a high molecular weight tau complex characterized by a Kd of 30 nM or less, preferably at a Kd of 10 nM or less, and yet more preferably at a Kd of less than 3 nM. This can be characterized that said the antibody or fragment has a binding affinity for the SEQ ID NO. 27 epitope or the SEQ ID NO. 27 epitope on a high molecular weight tau complex characterized by a Kd of a value between 10 nM to 1 nM.

In a particular embodiment, the antibody or antibody fragment comprises at least one CDR triplet selected from the group consisting of
a CDR triplet H1/H2/H3; and
a CDR triplet L1/L2/L3;
wherein H1 has an amino acid sequence which has at least 90% identity to SEQ ID NO. 19, H2 has an amino acid sequence which has at least 90% identity to SEQ ID NO. 20, H3 has an amino acid sequence which has at least 90% identity to SEQ ID NO. 21, L1 has an amino acid sequence which has at least 90% identity to SEQ ID NO. 22, L2 has an amino acid sequence which has at least 90% identity to SEQ ID NO. 23, and L3 has an amino acid sequence which has at least 90% identity to SEQ ID NO. 24 and it is characterized in that it recognizes high molecular weight tau complexes and -epitope 16-GTYGLGDRK-24 (SEQ ID NO. 27) for instance of human Tau isotope hTAU40 (Such antibody can hereafter be referred to as or ADx215); This has further been characterized that it has a much higher affinity (reduced exposure time). This can be characterized that said the antibody or fragment has a binding affinity for the SEQ ID NO. 27 epitope or the SEQ ID NO. 27 epitope on a high molecular weight tau complex characterized by a Kd of 30 nM or less, preferably at a Kd of 10 nM or less, and yet more preferably at a Kd of less than 3 nM. This can be characterized that said the antibody or fragment has a binding affinity for the SEQ ID NO. 27 epitope or the SEQ ID NO. 27 epitope on a high molecular weight tau complex characterized by a Kd of a value between 10 nM to 1 nM.

In a particular embodiment, the antibody or antibody fragment comprises at least one CDR triplet selected from the group consisting of
a CDR triplet H1/H2/H3; and
a CDR triplet L1/L2/L3;
wherein H1 has an amino acid sequence which has at least 95% identity to SEQ ID NO. 12, H2 has an amino acid sequence which has at least 95% identity to SEQ ID NO. 19, H3 has an amino acid sequence which has at least 95% identity to SEQ ID NO. 20, L1 has an amino acid sequence which has at least 95% identity to SEQ ID NO. 21, L2 has an amino acid sequence which has at least 95% identity to SEQ ID NO. 22, and L3 has an amino acid sequence which has at least 95% identity to SEQ ID NO. 23 and it is characterized in that it recognizes high molecular weight tau complexes and epitope 16-GTYGLGDRK-24 (SEQ ID NO. 27) for instance of human Tau isotope hTAU40 (Such antibody can hereafter be referred to as or ADx215). This has further been characterized that it has a much higher affinity (reduced exposure time). This can be characterized that said the antibody or fragment has a binding affinity for the SEQ ID NO. 27 epitope or the SEQ ID NO. 27 epitope on a high molecular weight tau complex characterized by a Kd of 30 nM or less, preferably at a Kd of 10 nM or less, and yet more preferably at a Kd of less than 3 nM. This can be characterized that said the antibody or fragment as a binding affinity for the SEQ ID NO. 27 epitope or the SEQ ID NO. 27 epitope on a high molecular weight tau complex characterized by a Kd of a value between 10 nM to 1 nM.

In a particular embodiment, the antibody or antibody fragment comprises at least one CDR triplet selected from the group consisting of
a CDR triplet H1/H2/H3; and
a CDR triplet L1/L2/L3;
wherein H1 has an amino acid sequence which has at least 98% identity to SEQ ID NO. 19, H2 has an amino acid sequence which has at least 98% identity to SEQ ID NO. 20, H3 has an amino acid sequence which has at least 98% identity to SEQ ID NO. 21, L1 has an amino acid sequence which has at least 98% identity to SEQ ID NO. 22, L2 has an amino acid sequence which has at least 98% identity to SEQ ID NO. 23, and L3 has an amino acid sequence which has at least 98% identity to SEQ ID NO. 24 and it is characterized in that it recognizes high molecular weight tau complexes and epitope 16-GTYGLGDRK-24 (SEQ ID NO. 27) for instance of human Tau isotope hTAU40 (Such antibody can hereafter be referred to as or ADx215. This has further been characterized that it has a much higher affinity (reduced exposure time). This can be characterized that said the antibody or fragment has a binding affinity for the SEQ ID NO. 27 epitope or the SEQ ID NO. 27 epitope on a high molecular weight tau complex characterized by a Kd of 30 nM or less, preferably at a Kd of 10 nM or less, and yet more preferably at a Kd of less than 3 nM. This can be characterized that said the antibody or fragment has a binding affinity for the SEQ ID NO. 27 epitope or the SEQ ID NO. 27 epitope on a high molecular weight tau complex characterized by a Kd of a value between 10 nM to 1 nM.

In a particular embodiment, the antibody or antibody fragment comprises at least one variable domain having an amino acid sequence selected from the group consisting of SEQ ID NO. 25 and 26 or an amino acid sequence which has at least 80% identity to an amino acid sequence selected from the group consisting of SEQ ID NO. 25 and 26 and it is characterized in that it recognizes high molecular weight tau complexes and epitope 16-GTYGLGDRK-24 (SEQ ID NO. 27) for instance of human Tau isotope hTAU40 (Such antibody can hereafter be referred to as or ADx215). This has further been characterized that it has a much higher affinity (reduced exposure time). This can be characterized that said the antibody or fragment has a binding affinity for the SEQ ID NO. 27 epitope or the SEQ ID NO. 27 epitope on a high molecular weight tau complex characterized by a Kd of 30 nM or less, preferably at a Kd of 10 nM or less, and yet more preferably at a Kd of less than 3 nM. This can be characterized that said the antibody or fragment has a binding affinity for the SEQ ID NO. 27 epitope or the SEQ ID NO. 27 epitope on a (high molecular weight tau complex) characterized by a Kd of a value between 10 nM to 1 nM.

In a particular embodiment, the antibody or antibody fragment comprises a heavy chain variable region having an amino acid sequence of SEQ ID NO. 25, or an amino acid sequence which has at least 80% identity to an amino acid sequence of SEQ ID NO. 25 and it is characterized in that it recognizes high molecular weight tau complexes and epitope 16-GTYGLGDRK-24 (SEQ ID NO. 27) for instance of human Tau isotope hTAU40 (Such antibody can hereafter be referred to as or ADx215). This has further been characterized that it has a much higher affinity (reduced exposure time). This can be characterized that said the antibody or fragment has a binding affinity for the SEQ ID NO. 27 epitope or the SEQ ID NO. 27 epitope on a high molecular weight tau complex characterized by a Kd of 30 nM or less, preferably at a Kd of 10 nM or less, and yet more preferably at a Kd of less than 3 nM. This can be characterized that said the antibody or fragment has a binding affinity for the SEQ ID NO. 27 epitope or the SEQ ID NO. 27 epitope on a high molecular weight tau complex characterized by a Kd of a value between 10 nM to 1 nM.

In a particular embodiment, the antibody or antibody fragment comprises a light chain variable region having an amino acid sequence of SEQ ID NO. 26, or an amino acid sequence which has at least 80% identity to an amino acid sequence of SEQ ID NO. 26 and it is characterized in that it recognizes high molecular weight tau complexes and epitope 16-GTYGLGDRK-24 (SEQ ID NO. 27) for instance of human Tau isotope hTAU40 (Such antibody can hereafter be referred to as or ADx215). This has further been characterized that it has a much higher affinity (reduced exposure time). This can be characterized that said the antibody or fragment has a binding affinity for the SEQ ID NO. 27 epitope or the SEQ ID NO. 27 epitope on a high molecular weight tau complex characterized by a Kd of 30 nM or less, preferably at a Kd of 10 nM or less, and yet more preferably at a Kd of less than 3 nM. This can be characterized that said the antibody or fragment has a binding affinity for the SEQ ID NO. 27 epitope or the SEQ ID NO. 27 epitope on a high molecular weight tau complex characterized by a Kd of a value between 10 nM to 1 nM.

In a particular embodiment, the antibody or antibody fragment comprises a heavy chain variable region having an amino acid sequence of SEQ ID NO. 25, or an amino acid sequence which has at least 90% identity to an amino acid sequence of SEQ ID NO. 25 and it is characterized in that it recognizes high molecular weight tau complexes and epitope 16-GTYGLGDRK-24 (SEQ ID NO. 27) for instance of human Tau isotope hTAU40 (Such antibody can hereafter be referred to as or ADx215). This has further been characterized that it has a much higher affinity (reduced exposure time). This can be characterized that said the antibody or fragment has a binding affinity for the SEQ ID NO. 27 epitope or the SEQ ID NO. 27 epitope on a high molecular weight tau complex characterized by a Kd of 30 nM or less, preferably at a Kd of 10 nM or less, and yet more preferably at a Kd of less than 3 nM. This can be characterized that said the antibody or fragment has a binding affinity for the SEQ ID NO. 27 epitope or the SEQ ID NO. 27 epitope on a high molecular weight tau complex characterized by a Kd of a value between 10 nM to 1 nM.

In a particular embodiment, the antibody or antibody fragment comprises a light chain variable region having an amino acid sequence of SEQ ID NO. 26, or an amino acid sequence which has at least 90% identity to an amino acid sequence of SEQ ID NO. 26 and it is characterized in that it recognizes high molecular weight tau complexes and epitope 16-GTYGLGDRK-24 (SEQ ID NO. 27) for instance of human Tau isotope hTAU40 (Such antibody can hereafter be referred to as or ADx215). This has further been characterized that it has a much higher affinity (reduced exposure time). This can be characterized that said the antibody or fragment has a binding affinity for the SEQ ID NO. 27 epitope or the SEQ ID NO. 27 epitope on a high molecular weight tau complex characterized by a Kd of 30 nM or less, preferably at a Kd of 10 nM or less, and yet more preferably at a Kd of less than 3 nM. This can be characterized that said the antibody or fragment has a binding affinity for the SEQ ID NO. 27 epitope or the SEQ ID NO. 27 epitope on a high molecular weight tau complex characterized by a Kd of a value between 10 nM to 1 nM.

In a particular embodiment, the antibody or antibody fragment comprises a heavy chain variable region having an amino acid sequence of SEQ ID NO. 25, or an amino acid sequence which has at least 95% identity to an amino acid sequence of SEQ ID NO. 25 and it is characterized in that it recognizes high molecular weight tau complexes and epitope 16-GTYGLGDRK-24 (SEQ ID NO. 27) for instance of human Tau isotope hTAU40 (Such antibody can hereafter be referred to as or ADx215). This has further been characterized that it has a much higher affinity (reduced exposure time). This can be characterized that said the antibody or fragment has a binding affinity for the SEQ ID NO. 27 epitope or the SEQ ID NO. 27 epitope on a high molecular weight tau complex characterized by a Kd of 30 nM or less, preferably at a Kd of 10 nM or less, and yet more preferably at a Kd of less than 3 nM. This can be characterized that said the antibody or fragment has a binding affinity for the SEQ ID NO. 27 epitope or the SEQ ID NO. 27 epitope on a high molecular weight tau complex characterized by a Kd of a value between 10 nM to 1 nM.

In a particular embodiment, the antibody or antibody fragment comprises a light chain variable region having an amino acid sequence of SEQ ID NO. 26, or an amino acid sequence which has at least 95% identity to an amino acid sequence of SEQ ID NO. 26 and it is characterized in that it recognizes high molecular weight tau complexes and epitope 16-GTYGLGDRK-24 (SEQ ID NO. 27) for instance of human Tau isotope hTAU40 (Such antibody can hereafter be referred to as or ADx215). This has further been characterized that it has a much higher affinity (reduced exposure time). This can be characterized that said the antibody or fragment has a binding affinity for the SEQ ID NO. 27 epitope or the SEQ ID NO. 27 epitope on a high molecular weight tau complex characterized by a Kd of 30 nM or less, preferably at a Kd of 10 nM or less, and yet more preferably at a Kd of less than 3 nM. This can be characterized that said the antibody or fragment has a binding affinity for the SEQ ID NO. 27 epitope or the SEQ ID NO. 27 epitope on a high molecular weight tau complex characterized by a Kd of a value between 10 nM to 1 nM.

In a particular embodiment, the antibody or antibody fragment comprises a heavy chain variable region having an amino acid sequence of SEQ ID NO. 25, or an amino acid sequence which has at least 98% identity to an amino acid sequence of SEQ ID NO. 25 and it is characterized in that it recognizes high molecular weight tau complexes and epitope 16-GTYGLGDRK-24 (SEQ ID NO. 27) for instance of human Tau isotope hTAU40 (Such antibody can hereafter be referred to as or ADx215). This has further been characterized that it has a much higher affinity (reduced exposure time). This can be characterized that said the antibody or fragment has a binding affinity for the SEQ ID NO. 27 epitope or the SEQ ID NO. 27 epitope on a high molecular weight tau complex characterized by a Kd of 30 nM or less, preferably at a Kd of 10 nM or less, and yet more preferably at a Kd of less than 3 nM. This can be characterized that said the antibody or fragment has a binding affinity for the SEQ ID NO. 27 epitope or the SEQ ID NO. 27 epitope on a high molecular weight tau complex characterized by a Kd of a value between 10 nM to 1 nM.

In a particular embodiment, the antibody or antibody fragment comprises a light chain variable region having an amino acid sequence of SEQ ID NO. 26, or an amino acid sequence which has at least 98% identity to an amino acid sequence of SEQ ID NO. 26 and it is characterized in that it recognizes high molecular weight tau complexes and epitope 16-GTYGLGDRK-24 (SEQ ID NO. 27) for instance of human Tau isotope hTAU40 (Such antibody can hereafter be referred to as or ADx215). This has further been characterized that it has a much higher affinity (reduced exposure time). This can be characterized that said the antibody or fragment has a binding affinity for the SEQ ID NO. 27 epitope or the SEQ ID NO. 27 epitope on a high molecular weight tau complex characterized by a Kd of 30 nM or less, preferably at a Kd of 10 nM or less, and yet more preferably at a Kd of less than 3 nM. This can be characterized that said the antibody or fragment has a binding affinity for the SEQ ID NO. 27 epitope or the SEQ ID NO. 27 epitope on a high molecular weight tau complex characterized by a Kd of a value between 10 nM to 1 nM.

In an alternative embodiment, the antibody or antibody fragment comprises at least one variable domain having an amino acid sequence selected from the group consisting of SEQ ID NO. 25 and 26, or an amino acid sequence which has at least 80, 81, 82, 83, 84, 85, 86, 87, 88, 89, 90, 91, 92, 93, 94, 95, 96, 97, 98, 99, or 100% identity to an amino acid sequence selected from the group consisting of SEQ ID NO. 25 and 26.

The term "complementarity determining region" or "CDR" refers to variable regions of either H (heavy) or L (light) chains (abbreviated as $V_H$ and $V_L$, respectively) and contains the amino acid sequences capable of specifically binding to antigenic targets. These CDR regions account for the specificity of the antibody for a particular antigenic determinant structure. Such regions are also referred to as "hypervariable regions." The CDRs represent non-contiguous stretches of amino acids within the variable regions but, regardless of species, the positional locations of these critical amino acid sequences within the variable heavy and light chain regions have been found to have similar locations within the amino acid sequences of the variable chains. The accepted CDR regions and variable domains of an antibody are known to the skilled person and have been described by (Kabat et al., 1991) and (Padlan et al., 1995).

The skilled person is familiar with the concept that, upon alignment of corresponding CDRs of different antibodies with similar antigen specificity, the positions in the alignment which are conserved, i.e. identical in all sequences in the alignment, are critical for the antigen specificity of the antibodies. The residues of a particular CDR at these critical positions are known as "specificity-determining residues" or "SDRs". As a consequence, positions which are not conserved contribute less to the specificity of the antibodies and can be substituted without substantially affecting the antigen specificity of an antibody. Therefore, the skilled person is able to determine which residues could be substituted without substantially affecting antigen specificity of the antibody or antibody fragment. In the same way, the skilled person is able to determine the minimum sequence identity between a particular CDR of an antibody and the corresponding CDR of an antibody of the present invention which is required for the particular CDR to have a similar antigen specificity as the corresponding CDR of an antibody of the present invention. The same holds true for the variable regions.

As used herein, "percentage identity" or "% identity" between two or more amino acid sequences or two or more nucleotide sequences refers to the ratio, expressed in %, of:
- the number of amino acids or nucleotides in an optimal alignment of the amino acid sequences or nucleotide sequences that are identical in both sequences (i.e. match) to
- the length of the alignment, i.e. the number of aligned positions, including gaps if any.

In a preferred embodiment, the antibody of the invention is secreted by the hybridoma cell line deposited under the Budapest Treaty at the Belgian Coordinated Collections of Microorganisms BCCM™/LMBP Collection under No. LMBP 8347CB. This hybridoma cell line and the secreted monoclonal antibody will hereinafter be referred to as ADx210, IGH-593 and/or 7G1G3. Another preferred monoclonal antibody of the invention is secreted by the hybridoma cell line deposited under the Budapest Treaty at the Belgian Coordinated Collections of Microorganisms BCCM™/LMBP Collection under No. LMBP 8348CB. This hybridoma cell line and the secreted monoclonal antibody will hereinafter be referred to as ADx211, IGH-603 and/or 23H5G11. Another preferred antibody of the invention is secreted by the hybridoma cell line ADx215 deposited under the Budapest Treaty at the Belgian Coordinated Collections of Microorganisms BCCM™/LMBP Collection under No. LMBP 9679CB. This hybridoma cell line and the secreted monoclonal antibody will hereinafter be referred to as ADx210. The term "hybridoma" is well recognized in the art and refers to a cell line resulting from the fusion of a single antibody-producing cell clone and an immortal cell or tumor cell. As used throughout the text, the term ADx and ADX are used interchangeably.

Protein delivery can be used to deliver the tau antibody, tau antibody-like scaffold or tau antibody fragment of present invention intracellular. Protein delivery, i.e., protein transduction is the process by which a peptide or protein motif crosses the cell plasma membrane. The delivery protein may include an intracellular protein, cell-surface protein, biologically active peptide, protein-nucleic acid conjugate, peptide-nucleic acid conjugate, fusion protein, synthetic peptide, protein-nanoparticle conjugate, protein-polymer conjugate, conjugate between a protein-organic chemical entity or protein-inorganic chemical entity, multi-protein complexes, or any amino-acid containing moiety. Researchers have developed a number of protein-transduction domains (PTDs) that mediate protein delivery into cells. These PTDs or signal peptide sequences are naturally occurring polypeptides of 15 to 30 amino acids, which normally mediate protein secretion in the cells. They are composed of a positively charged amino terminus, a central hydrophobic core and a carboxyl-terminal cleavage site recognized by a signal peptidase. Recently, researchers have shown that a number of membrane-translocating peptides can successfully mediate delivery of polypeptides, protein domains, and full-length protein, including antibodies into cells using solution-based protein transfection protocols. Recently, researchers have also demonstrated the use of lipid liposomes or the like for protein delivery. These technologies are useful to the deliver the tau antibody, tau antibody-like scaffold or tau antibody fragment op present invention into cells.

The invention also discloses a method for transfecting living cells with tau antibody, tau antibody-like scaffold or tau antibody fragment of present invention using surface-mediated delivery. According to an embodiment of the method, a substrate surface having a tau antibody, tau antibody-like scaffold or tau antibody fragment of present to be introduced into cells, is used for culturing cells. The tau antibody, tau antibody-like scaffold or tau antibody fragment of present to be introduced into cells is pre-complexed with a carrier reagent before being applied to the surface. Cells are then overlaid onto the prepared surface. The carrier reagents promote the delivery of the protein of interest into the cell, thus transfecting the cells. Alternatively, tau antibody, tau antibody-like scaffold or tau antibody fragment of present are attached on a suitable substrate surface, then a carrier reagent is added to the proteins to form complexes on the surface. In another embodiment, a fusion protein is used directly. The fusion protein contains a tau antibody, tau antibody-like scaffold or tau antibody fragment of present, fused covalently with any kind of protein or peptide that exhibits properties for spontaneous intracellular penetration (e.g., a herpes simplex protein, VP22). Preferably, a mixture containing a tau antibody, tau antibody-like scaffold or tau antibody fragment of present and a carrier reagent includes a helper reagent to enhance the protein delivery efficiencies. The present method produces a greater than 90% efficiency under optimized conditions for cell uptake of proteins. The present surface-mediated protein delivery technique is also referred to as a "reverse protein delivery." Such delivery may be used in vivo or in vitro.

The particular embodiments of the invention are described in terms of a carrier reagent. Carrier reagents may comprise a variety of species. In one embodiment, the carrier reagent is a bioactive cell membrane-permeable reagent, or other peptides containing protein-transduction domains (PTDs) (i.e., single peptide sequences comprising about 15 to about 30 residues). Protein-transduction domains (PTDs) mediate protein secretion, and are composed of a positively charged amino terminus, a central hydrophobic core and a carboxyl-terminal cleavage site recognized by a single peptidase. Examples of such membrane-transducing peptides include Trojan peptides, human immuodeficiency virus (HIV)-1 transcriptional activator (TAT) protein or its functional domain peptides, and other peptides containing protein-transduction domains (PTDs) derived from translocation proteins such as Drosophilia homeotic transcription factor Antennapedia (Antp) and herpes simplex virus DNA-binding protein, VP22, and the like. Some commerically available peptides, for example, penetratin 1, Pep-1 (Chariot reagent, Active Motif Inc., CA) and HIV GP41 fragment (519-541), can be used. Other carrier reagents include signal sequences, which have been used efficiently to target proteins to specific locations in both prokaryotic and eukaryotic cells, and a number of membrane-translocating peptides. Membrane-translocating peptides have been applied successfully to mediate membrane-translocation and the importation of a polpeptide, protein domain, full-length protein, or antibody into a cell using standard solution-based transfection protocols. The carrier reagent is a bioactive peptide or ligand that can specifically bind to and activate cell surface receptors. After binding to the cell surface receptors, the receptor and bound carrier-tau antibody complex, carrier-tau antibody-like scaffold complex or carrier-tau antibody fragment complex will undergo internalization, delivering ligand-antibody, ligand-antibody fragment or ligand-antibody-like scaffold complexes into cells. The proteins may be complexed with the ligand beforehand or in situ. The ligand can be complexed with the tau antibody, tau antibody-like scaffold or tau antibody fragment to be introduced into cells by means of non-covalent interaction such as hydrophobic interaction or electrostatic interaction or both, or coupled covalently to the protein, or by means of a ligand-receptor binding interaction. For example, a carrier reagent can be modified with a ligand that can bind specifically to the protein of interest. To illustrate, a synthetic ligand termed "Streptaphage" has efficiently delivered streptavidin to mammalian cells by promoting non-covalent interactions with cholesterol and sphingolipid-rich lipid raft subdomains of cell plasma membranes (Hussey, S. L. & Peterson, B. R., J. Am. Chem. Soc., 124, 6265-6273 (2002)).

In another embodiment, the carrier reagent is a lipid liposome or the like that can complex with the tau antibody, tau antibody-like scaffold or tau antibody fragment of present invention and promote the delivery of the protein into the cell. For example, the protein encapsulated in the formulation binds to the negatively vehicle for delivery (O. Zelphati et al., J. Bio. Chem., 276, 35103-19 (2001)). Products available commercially can be used, such as BioPORTER (Gene Therapy Systems), or ProVectin (Imgenex, San Diego, Calif.).

Protein delivery reagents (e.g., Chariot™ by Active Motif, or BioPORTER® by Gene Therapy Systems) can help save time by bypassing the traditional DNA transfection, transcription and protein translation processes associated with gene expression. Depending on the nature of the particular reagent employed, fusion proteins or chemical coupling in some embodiments would not be needed. The reagent forms a complex with the protein, stabilizes the macromolecule and protects it from degradation during delivery. Once internalized in a cell, the complex can dissociate, leaving the macromolecule biologically active and free to proceed to its target organelle. This is an alternative system to deliver the tau antibody, tau antibody-like scaffold or tau antibody fragment of present invention into a target cell.

The particular embodiments of the invention are described in terms of a helper reagents: The particular embodiments of the invention are described in terms of a helper reagent. In one embodiment, the helper reagent is a polymer such as DEAE-dextran, dextran, polylysine, and polyethylamine. In another embodiment, a helper reagent can also be a cell adherent-enhancing protein, such as fibronectin and gelatin. The helper reagent can be a sugar-based gelatin (e.g., polyethylene glycol) or a synthetic or chemical-based gelatin, such as acrylamide. In a further embodiment, the helper reagent can be a RGD peptide, such as Arg-Gly-Asp-Ser (SEQ ID NO. 52), Arg-Gly-Asp-Ser-Pro-Ala-Ser-Ser-Lys-Pro (SEQ ID NO. 53), and the like. Alternatively, the helper reagent can be a mixture of a hydrogel and a RGD peptide, and combination of any the aforementioned molecules. The use of helper reagents enhances the efficiency of protein delivery into the cells.

Also provided are isolated cell lines producing the antibody or antibody fragments of the present invention. Under "cell line" is to be understood a homogenous population of eukaryotic cells which is genetically stable and can be cultured. Preferably, the cell line is of animal origin. More preferably, the cell line is immortalized. Alternatively, the cell line is of plant or fungal origin. In one embodiment, the cell line of the invention is obtained by genetic transformation with a nucleic acid comprising a polynucleotide encoding the antibody or antibody fragment of the invention under suitable transcriptional and translational control elements, which are known to those skilled in the art, to allow efficient production of the antibody or antibody fragment. In another embodiment, the cell line is a hybridoma cell line selected from the group consisting of hybridoma cell line ADX210 deposited under the Budapest Treaty at the Belgian Coordinated Collections of Microorganisms BCCM™/LMBP Collection under No. LMBP 8347CB, and hybridoma cell line ADX211 deposited under the Budapest Treaty at the Belgian Coordinated Collections of Microorganisms BCCM™/LMBP Collection under No. LMBP 8348CB, and hybridoma cell line ADx215 deposited under the Budapest Treaty at the Belgian Coordinated Collections of Microorganisms BCCM™/LMBP Collection under No. LMBP 9679CB Further provided are isolated nucleic acids comprising a polynucleotide encoding the antibody or antibody fragment of the invention. In a preferred embodiment, said polynucleotide comprises or consists essentially of or consists of a nucleotide sequence encoding an antibody fragment of SEQ ID NO. 15 to SEQ ID NO. 18 and SEQ ID NO. 19 to SEQ ID NO. 26. In a more preferred embodiment, said polynucleotide comprises or consists essentially of or consists of the nucleotide sequences encoding the antibody fragment of SEQ ID NO 15 to SEQ ID NO. 18 or SEQ ID NO 25 to SEQ ID NO 26 or SEQ ID NO. 9 to SEQ ID NO. 14 or from of SEQ ID NO. 19 to SEQ ID 24 or from SEQ ID NO 25 to SEQ ID NO. 26. In an even more preferred embodiment, said polynucleotide comprises or consists essentially of or consists of a nucleotide sequence encoding the antibody fragment selected from the group consisting of SEQ ID NO. 9, 10, 11, 12, 13, 14, 15, 16, 17, 18, 19, 20, 21, 22, 23, 24, 25 and 26.

For conventional antibodies composed of heavy and light chains, the polynucleotides encoding the individual chains may be isolated from mature B-cells or hybridomas producing the antibody of the invention, e.g. by polymerase chain reaction (PCR) or reverse transcription (RT)-PCR, using primers, known to the person skilled in the art, that are suitable for amplification of the heavy and light chain genes or cDNAs. For heavy chain antibodies, the polynucleotide encoding the single chain may be isolated from mature B-cells or hybridomas producing the antibody of the invention, e.g. by polymerase chain reaction (PCR) or reverse transcription (RT)-RPC using primers that are suitable for amplification of the heavy chain gene or cDNA.

It is clear to the person skilled in the art that the obtained polynucleotides can be further manipulated to obtain alternative polynucleotides encoding the antibody fragments of the present invention, or to generate recombinant gene constructs encoding the antibodies and antibody fragments of the invention, as described herein. The polynucleotides of the invention can be further altered by random or site-directed mutagenesis to improve specificity or affinity of the encoded antibody or antibody fragment. The skilled person is also sufficiently acquainted with recombinant DNA technology in order to obtain gene constructs suitable for prokaryotic and eukaryotic expression, i.e. by the addition of transcriptional control elements such as promoters and terminators to the gene construct, and translational control elements such as ribosome entry sites. Thus the nucleic acids of the invention can be introduced into prokaryotic or eukaryotic host cells such as cell lines or germ line cells in order to obtain heterologous production of the antibodies and antibody fragments of the invention.

Further provided are isolated nucleic acids comprising a polynucleotide encoding the tau antigen fragment binding to of one of the antibodies of the present invention. In a preferred embodiment, said polynucleotide comprises a nucleotide sequence encoding the tau antigen fragment binding to the antibody produced by cell line ADx215 deposited under the Budapest Treaty at the Belgian Coordinated Collections of Microorganisms BCCM™/LMBP Collection under No. LMBP 9679CB. Preferrably the polynucleotide comprises or consists essentially of or consists of a nucleotide sequence encoding the tau antigen fragment of SEQ ID NO. 27. Preferably the polynucleotide comprises or consists essentially of or consists of a nucleotide sequence encoding the tau antigen fragment of SEQ ID NO. 28.

Also provided by the present invention are methods to induce an immune response towards phosphorylated tau aggregates in an animal, comprising administering to said animal phosphorylated tau aggregates. In a preferred embodiment, the phosphorylated tau aggregates are obtainable by production of 2N/4R tau in a yeast strain in which the PHO85 gene has been deleted (pho85Δ strain), as described in (Vandebroek et al., 2005) and in the Examples. In a more preferred embodiment, the phosphorylated tau aggregates are soluble. In an even more preferred embodiment, the phosphorylated tau aggregates comprise dimers and/or trimers of phosphorylated tau.

The immunogenic phosphorylated tau aggregates can be administered alone or in combination with a suitable adjuvant. Suitable adjuvants can be administered before, after, or concurrent with administration of the immunogenic phosphorylated tau aggregates. Preferred adjuvants are aluminum salts (alum), such as aluminum hydroxide, aluminum phosphate, and aluminum sulfate. Adjuvants can be used with or without other specific immunostimulating agents, such as 3-de-O-acetylated monophosphoryl lipid A (3-DMP), polymeric or monomeric amino acids, such as polyglutamic acid or polylysine. Such adjuvants can be used with or without other specific immunostimulating agents, such as muramyl peptides (e.g., N-acetylmuramyl-L-threonyl-D-isoglutamine (thr-MDP), N-acetyl-normuramyl-L-alanyl-D-isoglutamine (nor-MDP), liposomal muramyl tripeptide phosphatidyl ethanolamine (MTP-PE), N-acetylglucsaminyl-N-acetylmuramyl-L-Ala-D-isoGlu-L-Ala-dipalmitoxy propylamide (DTP-DPP, Theramide™), or other bacterial cell wall components. Oil-in-water emulsions include MF59 (see WO 90/14837 to Van Nest et al., which is hereby incorporated by reference in its entirety), containing 5% Squalene, 0.5% Tween 80, and 0.5% Span 85 (optionally containing various amounts of MTP-PE) formulated into submicron particles using a micro fluidizer; SAF, containing 10% Squalene, 0.4% Tween 80, 5% pluronic-blocked polymer L121, and thr-MDP, either micro fluidized into a submicron emulsion or vortexed to generate a larger particle size emulsion; and the Ribi™ adjuvant system (RAS) (Ribi ImmunoChem, Hamilton, Mont.) containing 2% squalene, 0.2% Tween 80, and one or more bacterial cell wall components selected from the group consisting of monophosphoryllipid A (MPLA), trehalose dimycolate (TDM), and cell wall skeleton (CWS), preferably MPL+CWS (Detox™). Other adjuvants include Complete Freund's Adjuvant (CFA), Incomplete Freund's Adjuvant (IFA), and cytokines, such as interleukins (IL-I, IL-2, and IL-12), macrophage colony stimulating factor (M-CSF), and tumor necrosis factor (TNF). The choice of an adjuvant depends on the stability of the immunogenic formulation containing the adjuvant, the route of administration, the dosing schedule, the efficacy of the adjuvant for the species being vaccinated, and, in humans, a pharmaceutically acceptable adjuvant is one that has been approved or is approvable for human administration by pertinent regulatory bodies. For example, alum, MPL or Incomplete Freund's adjuvant (Chang et al, Advanced Drug Delivery Reviews 32:173-186 (1998), which is hereby incorporated by reference in its entirety) alone or optionally all combinations thereof are suitable for human administration.

In a preferred embodiment, the method to induce an immune response towards phosphorylated tau aggregates is for obtaining a tau-specific antibody or antibody fragment preferentially binding to phosphorylated tau aggregates. Methods for obtaining antibodies after immunization are known to the skilled person.

As an alternative, antibodies and antibody fragments of the invention can be obtained using various phage display methods known in the art. In phage display methods, functional antibody domains are displayed on the surface of phage particles which carry the polynucleotide sequences encoding them. In particular, such phage can be utilized to display epitope-binding domains expressed from a repertoire or combinatorial antibody library (e.g., human or murine). Phage expressing an epitope-binding domain that binds the antigen of interest can be selected or identified with antigen, e.g., using labeled antigen bound or captured to a solid surface or bead. Phages used in these methods are typically filamentous phage including fd and M13 binding domains expressed from phage with antigen-binding antibody domains recombinantly fused to either the phage gene III or gene VIII protein. Examples of phage display methods that can be used to make the antibodies or antibody fragments of the present invention include those disclosed in (Kettleborough et al., 1994; Burton and Barbas, III, 1994; Brinkmann et al., 1995; Ames et al., 1995; Persic et al., 1997); WO/1992/001047; WO 5 90102809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108.

After phage selection, the regions of the phage encoding the fragments can be isolated and used to generate the epitope-binding fragments through expression in a chosen host, including mammalian cells, insect cells, plant cells, yeast, and bacteria, using recombinant DNA technology. For example, techniques to recombinantly produce antigen-binding fragments can also be employed using methods known in the art such as those disclosed in WO 92/22324; (Better et al., 1988; Mullinax et al., 1992; Sawai et al., 1995). Examples of techniques which can be used to produce single-chain Fvs and antibodies include those described in U.S. Pat. Nos. 4,946,778 and 5,258,498; (Skerra and Pluckthun, 1988; Huston et al., 1991; Shu et al., 1993).

The antibody of the present invention can be used in a method for diagnosis or detection of a neurological disorder, such as Alzheimer's disease, by detecting phoshorylated Tau polypeptide or functional parts thereof and/or phoshorylated Tau polypeptide in an oligomeric form.

Diagnosis or detection of a tau-associated disease or condition or of a predisposition to a tau-associated disease or condition in an individual may be achieved by detecting the immunospecific binding of a monoclonal antibody or a functional fragment thereof to an epitope of the tau protein in a sample or in situ, which includes bringing the sample or a specific body part or body area suspected to contain the tau antigen into contact with an antibody which binds an epitope of the tau protein, allowing the antibody to bind to the tau antigen to form an immunological complex, detecting the formation of the immunological complex and correlating the presence or absence of the immunological complex with the presence or absence of the tau antigen in the sample or specific body part or body area, optionally comparing the amount of said immunological complex to a normal control value, wherein an increase in the amount of said complex compared to a normal control value indicates that said individual is suffering from or is at risk of developing a tau-associated disease or condition. In a preferred embodiment, diagnosis or detection of a tau-associated disease or condition or of a predisposition to a tau-associated disease or condition in an individual is achieved by detecting the immunospecific binding of a monoclonal antibody of the present invention to aggregated tau. Preferably, the antibody for use in the method of detection is ADX210 or a functional fragment thereof. Preferably, the antibody for use in the method of detection is ADX215 or a functional fragment thereof.

"Diagnosis" is defined herein to include monitoring the state and progression of the disease, checking for recurrence of disease following treatment and monitoring the success of a particular treatment. The test may also have prognostic value. The prognostic value of the tests may be used as a marker of potential susceptibility to tauopathy. Thus patients at risk may be identified before the disease has a chance to manifest itself in terms of symptoms identifiable in the patient.

Thus, the invention provides for methods for the detection of phosphorylated tau aggregates in which the antibodies and antibody fragments of the present invention are used. In one embodiment, the method comprises the following steps:
  contacting an antibody or antibody fragment of the invention with a sample under conditions suitable for producing an antigen-antibody complex; and
  detecting the formation of said antigen-antibody complex.

Immunological methods for detecting immunospecific binding include but are not limited to fluid or gel precipitation reactions, immuno diffusion (single or double), agglutination assays, immuno-electrophoresis, radio-immunoassays (RIA), enzyme-linked immunosorbent assays (ELISA), Western blots, dot blots, slot blots, liposome immunoassays, line immunoassays (LIA), complement-fixation assays, fluorescent immunoassays, Luminex™ xMAP™, immunofluorescent flow cytometry, protein A immunoassays, or immuno PCR. An overview of different immunoassays is given in (Wild D. (2001), The Immunoassay Handbook 2nd edition. Nature Pr., London, UK) and (Ghindilis A. L., Pavlov A. R., Atanassov P. B. (eds.) (2002) Immunoassay Methods and Protocols. Humana Press, Totowa, N.J., US). Immunological detection methods further comprise immunohistochemistry, immunofluoromicroscopy and immunoelectron microscopy.

In one embodiment, the antibody or antibody fragment of the invention is used as a capture antibody and may be bound (e.g., covalently or non-covalently, via hydrophobic or hydrophilic interactions, hydrogen bonding, or van der Waals forces) to a solid phase, such as a bead, a plate, a membrane or a chip. Methods of coupling biomolecules, such as antibodies or antigens, to a solid phase are well known in the art. They can employ, for example, bifunctional linking agents, or the solid phase can be treated with a reactive group, such as an epoxide or an imidizole, that will bind the molecule on contact. It is to be understood that more than one antibody or antibody fragment of the invention can be used concomitantly to capture the phosphorylated tau aggregates. The immobilized antibody or antibody fragment of the invention is then brought into contact with the sample to be tested for phosphorylated tau aggregates. Samples to be tested may include bodily samples such as CSF, blood, plasma, serum, urine, etc., but also in vitro generated samples. After removal of unbound sample, the antigen-antibody complex can be detected by detection of the bound phosphorylated tau aggregates. This detection can be performed by using an antibody able to bind to aggregated tau, phosphorylated tau, or tau. Alternatively, the whole antibody-antigen complex is detected.

In an alternative embodiment, the capturing is done with an antibody able to bind to aggregated tau, phosphorylated tau, or tau, and the detection is performed by using an antibody or antibody fragment of the invention. In any case, specificity of the assay for phosphorylated tau aggregates is obtained by using an antibody or antibody fragment of the invention for either capturing or detection.

Detection of the antigen-antibody complex can be performed by various methods known to the skilled person.

The particular label or detectable group used in the assay is generally not a critical aspect of the invention, as long as it does not significantly interfere with the specific binding of the antibody or antibody fragment to the antigen. The detectable group can be any material having a detectable physical or chemical property. Such detectable labels have been well developed in the field of immunoassays and, in general, almost any label useful in such methods can be applied to the method of the present invention. Thus, a label is any composition detectable by spectroscopic, photochemical, biochemical, immunochemical, electrical, optical, radiological or chemical means. Useful labels in the present invention include but are not limited to magnetic beads (e.g. Dynabeads™), fluorescent dyes (e.g. fluorescein isothiocyanate, texas red, rhodamine), radiolables (e.g. 3R, 125I, 35S, 14C, or 32p), enzymes (e.g. horseradish peroxidase, alkaline phosphatase, luciferase, and others commonly used in an ELISA), and colorimetric labels such as colloidal gold, colored glass or plastic (e.g. polystyrene, polypropylene, latex, etc.) beads. As indicated above, a wide variety of labels may be used, with the choice of label depending on the sensitivity required, the ease of conjugation with the compound, stability requirements, the available instrumentation and disposal provisions. Non-radioactive labels are often attached by indirect means. Generally, a ligand molecule (e.g. biotin) is covalently bound to the antibody. The ligand then binds to an anti-ligand (e.g. streptavidin) molecule, which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with the labeled, naturally occurring anti-ligands. Alternatively, a haptenic or antigenic compound can be used in combination with an antibody. The antibodies can also be conjugated directly to signal-generating compounds, for example, by conjugation with an enzyme or fluorophore. Enzymes of interest will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescent compounds include luciferin, and 2,3-dihydrophtalazinediones, for example, luminol. A review of other labeling or signal producing systems is available in U.S. Pat. No. 4,391,904. Means for detecting labels are well known in the art. Thus, for example, where the label is a radioactive label, means for detection include a scintillation counter or photographic film as in autoradiography. Where the label is a fluorescent label, it may be detected by exciting the fluorophore with the appropriate wavelength of light and detecting the resulting fluorescence. The fluorescence may be detected visually, by means of a photographic film, by the use of electronic detectors such as charge coupled devices (CCDs) or photomultipliers and the like. Similarly, enzyme labels may be detected by providing the appropriate substrates for the enzyme and detecting the resulting reaction product. Finally simple colorimetric labels may be detected simply by observing the color associated with the label.

As used herein a "tauopathy" or "tau-associated disease" encompasses any neurodegenerative disease that involves the pathological aggregation of the microtubule protein tau within the brain. Accordingly, in addition to both familial and sporadic Alzheimer's disease, other tauopathies that can be treated using the methods of the present invention include, without limitation, frontotemporal dementia, parkinsonism linked to chromosome 17 (FTDP-17), progressive supranuclear palsy, corticobasal degeneration, Pick's disease, progressive subcortical gliosis, tangle only dementia, diffuse neurofibrillary tangles with calcification, argyrophilic grain dementia, amyotrophic lateral sclerosis parkinsonism-dementia complex, dementia pugilistica, Down syndrome, Gerstmann-Straussler-Scheinker disease, Hallerworden-Spatzdisease, inclusion body myositis, Creutzfeld-Jakob disease, multiple system atropy, Niemann-Pick disease type C, prion protein cerebral amyloid angiopathy, subacute sclerosing panencephalitis, myotonic dystrophy, non-guanamian motor neuron disease with neurofibrillary tangles, postencephalitic parkinsonism, and chronic traumatic encephalopathy.

The antibody of the present invention can be used in a method for monitoring residual disease, such as Alzheimer's disease, following treatment with a vaccine composition. Monitoring minimal residual disease in an individual following treatment with a vaccine composition may be achieved by detecting the immunospecific binding of a monoclonal antibody or a functional fragment thereof to an epitope of the tau protein in a sample or in situ, which includes bringing the sample or a specific body part or body area suspected to contain the tau antigen into contact with an antibody which binds an epitope of the tau protein, allowing the antibody to bind to the tau antigen to form an immunological complex, detecting the formation of the immunological complex and correlating the presence or absence of the immunological complex with the presence or absence of the tau antigen in the sample or specific body part or body area, optionally comparing the amount of said immunological complex to a normal control value, wherein an increase in the amount of said aggregate compared to a normal control value indicates that said individual is still suffering from a minimal residual disease. In a preferred embodiment, Monitoring minimal residual disease in an individual following treatment with a vaccine composition is achieved by detecting the immunospecific binding of a monoclonal antibody of the present invention to aggregated tau. Preferably, the antibody for use in the method of detection is ADX210 or a functional fragment thereof. Preferably, the antibody for use in the method of detection is ADX215 or a functional fragment thereof.

The antibody of the present invention can also be used in a method for predicting responsiveness of a patient to a treatment with a vaccine composition. Predicting responsiveness of a patient to a treatment with a vaccine composition may be achieved by detecting the immunospecific binding of a monoclonal antibody or a functional fragment thereof to an epitope of the tau protein in a sample or in situ, which includes bringing the sample or a specific body part or body area suspected to contain the tau antigen into contact with an antibody which binds an epitope of the tau protein, allowing the antibody to bind to the tau antigen to form an immunological complex, detecting the formation of the immunological complex and correlating the presence or absence of the immunological complex with the presence or absence of the tau antigen in the sample or specific body part or body area, optionally comparing the amount of said immunological complex before and after onset of the treatment, wherein a decrease in the amount of said complex indicates that said individual has a high potential of being responsive to the treatment. In the alternative, the method for predicting responsiveness of a patient to a treatment with a vaccine composition may detect that there is no decrease in the amount of the immunological complex before and after onset of the treatment and thus indicate that the individual has low potential of being responsive to the treatment. In a preferred embodiment, predicting responsiveness to a treatment with a vaccine composition in an idividual is be achieved by detecting the immunospecific binding of a monoclonal antibody of the present invention to aggregated tau. Preferably, the antibody for use in the method of detection is ADx210 or a functional fragment thereof. Preferably, the antibody for use in the method of detection is ADx215 or a functional fragment thereof.

The invention also provides peptides representing an epitope of the tau protein, which epitope is recognized by an antibody according the present invention. In a preferred embodiment, the peptide comprises, consists essentially of, or consists of the amino acid sequence represented by SEQ ID NO. 27. Suitable additional amino acid sequences may need to be added in order to improve immunoreactivity. Indeed, as shown in the Experimental part, for optimal recognition of minimal epitope represented by SEQ ID NO; 27, a N-terminal part of tau predicted to form an α-helix (DeLeys, R. et al., 1995) as represented by SEQ ID NO. 28 is required. Thus, the sequence needed in a synthetic peptide to serve as epitope for YT1.15 as a calibrator is $E_7FEVMEDHAG_{16}TYGLGDRK_{24}$ (SEQ ID NO. 29.) Accordingly, in one embodiment, the peptide comprises the amino acid sequence represented by SEQ ID NO. 27 and is 9 to 19 amino acids in length. Preferably, the peptide is 9, 10, 11, 12, 13, 14, 15, 16, 17, 18, 19, 20, 21, 22 or 23 amino acids in length and comprises or consists essentially or consists of the amino acid sequence represented by SEQ ID NO. 27. In a preferred embodiment, the peptide consists essentially of, or consists of the sequence represented by SEQ ID NO. 29.

The peptides of the present invention find their application in various methods and tests, such as but not limited to methods for diagnosis or the detection of a tau-associated disease or condition or of a predisposition to a tau-associated disease or condition in an individual, methods for monitoring residual disease, such as Alzheimer's disease, following treatment with a vaccine composition, or methods for predicting responsiveness of a patient to a treatment with a vaccine composition. The peptides may be used as suitable controls to ensure that the methods and tests are working properly. The peptides may for instance be used as positive controls, as internal standards, as calibrators, or for quantification purpose.

The invention also provides kits which may be used in order to carry out the methods of the invention. The kits may incorporate any of the preferred features mentioned in connection to the various methods and uses of the invention described herein. Thus, the invention provides a kit for detecting a tau-associated disease or condition or of a predisposition to a tau-associated disease or condition in a body sample of an individual, and comprises at least one or more antibodies of the present invention, preferably the antibody ADx210 and/or ADx215. In particular, the test kit comprises a container holding a packaged combination of reagents in predetermined amounts, such as one or more antibodies according to the present invention, with in instructions for performing the diagnostic assay. Where the antibody is labeled with an enzyme, the kit will include substrates and co-factors required by the enzyme. Further additives may be included such as stabilizers, buffers and the like. The kit comprising one or more antibodies of the present invention may be used to discriminate for instance early stage Alzheimer's dementia form other types of dementia in an individual. The kit comprising one or more antibodies of the present invention may be used to identify compositions which interfere with formation or stability of phosphorylated tau aggregates. The kit may incorporate suitable controls to ensure that the method and test is working properly. The kit may for that purpose incorporate one or more peptides of the present invention. Preferably, the kit incorporates a peptide Characteristics of the one or more antibodies and of the one or more peptides are summarized elsewhere in the detailed description and in the experimental part below.

FIGURES

FIG. 1: Accumulation of oligomeric tau is dependent on the yeast growth characteristics. A pho85Δ yeast strain transformed with a HIS6-PG-TEV-hTau (2N/4R) plasmid was inoculated in SD-URA medium. Subsequent sampling at different OD's was followed by protein extraction and non-reducing SDS-PAGE. Tau was detected with the ADx215 monoclonal antibody. Besides monomeric tau (~75 kDa), higher weight dimeric and higher oligomeric species of tau can be detected.

Figure 2:
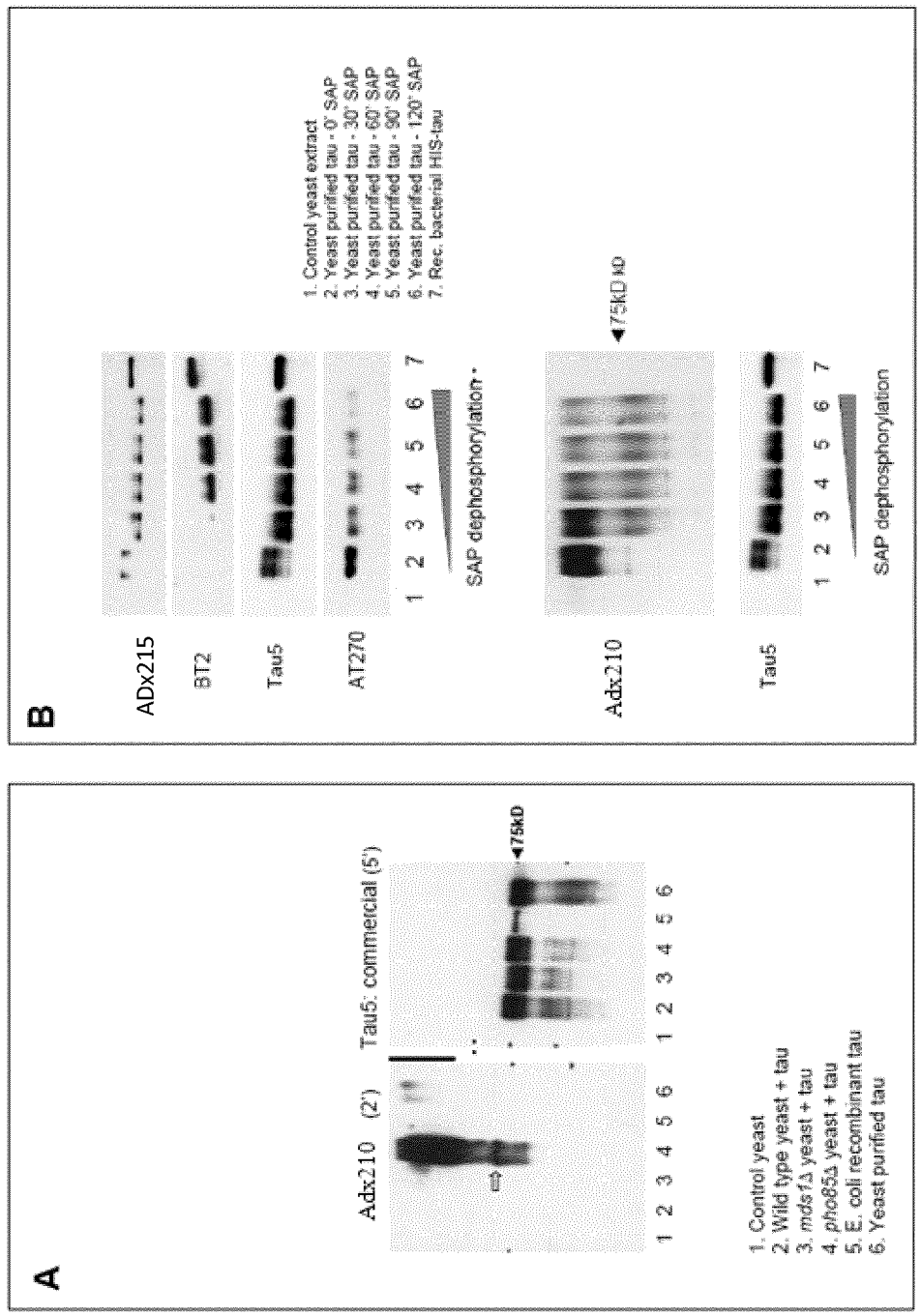

FIG. 2: Selectivity for tau aggregates and phosphorylation dependency of anti-tau mAbs of the invention. A) Western blot analysis of recombinant HIS-tagged tau obtained from E. coli and protein extracts obtained from control and humanized yeast strains using the commercial pan-tau antibody Tau-5 and ADx210 mAb as indicated. The number between brackets refers to the exposure time. The solid bar refers to high molecular weight and oligomeric tau and the small arrow in the picture of ADx210 to a presumable tau dimer. B) Western blot analysis of purified tau obtained from the pho85Δ strain before and after treatment with shrimp alkaline phosphatase (SAP) following different time intervals as indicated. Recombinant HIS-tagged tau obtained from E. coli served as control. The pan-tau antibody Tau-5, the phosphorylation-specific antibody AT270, and the antibody BT2 recognizing non-phosphorylated tau, were used in addition to the novel mAbs ADx215 and ADx210.

Figure 3:
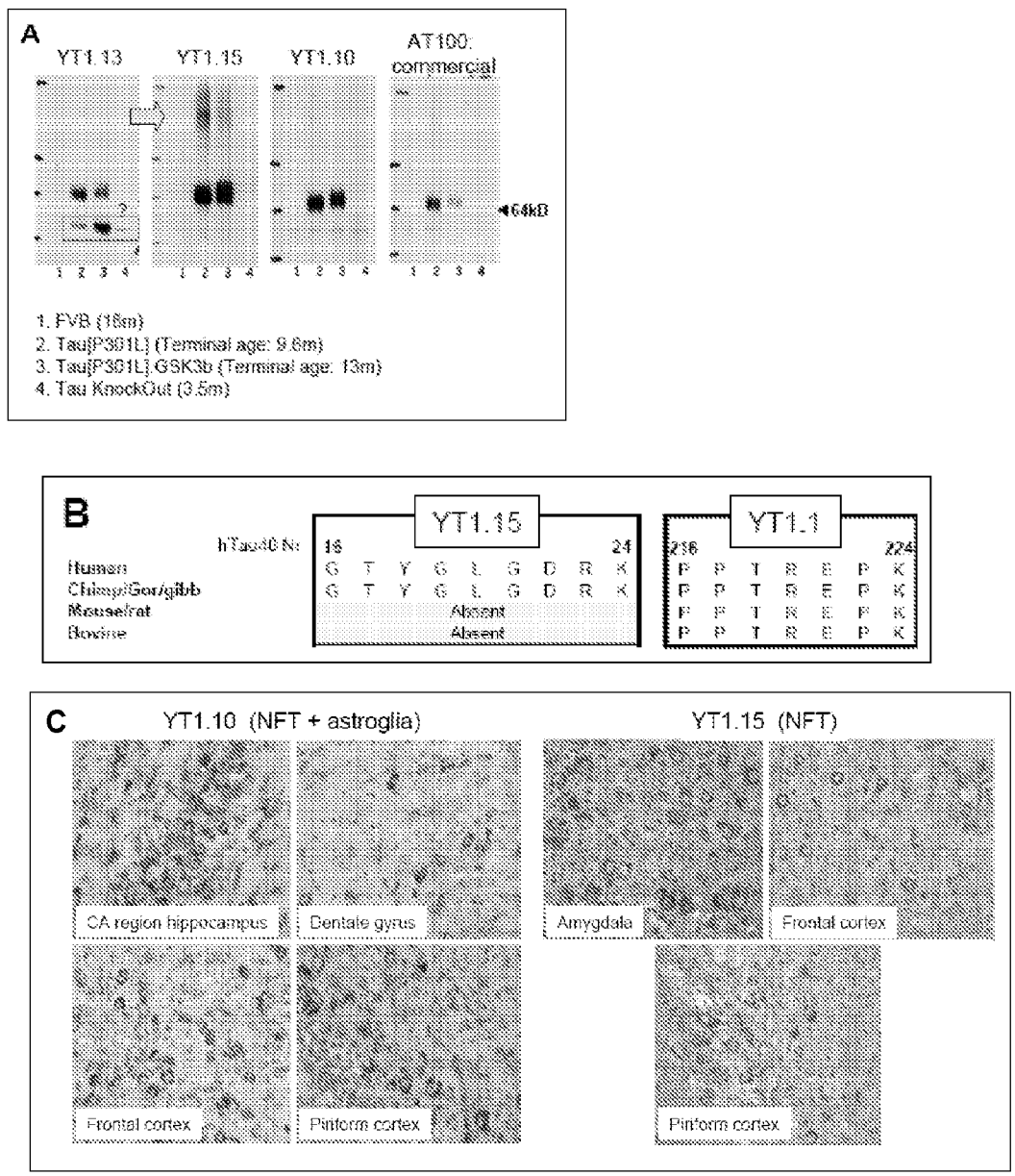

FIG. 3: Analysis of the novel mAbs on samples of transgenic mice and human brain. A) Western blot analysis of brain extracts from control mice (FVB), knock-out mice and transgenic (Tg) mice expressing a clinical mutant of human tau (Tau-P301L). The age of the mice is indicated between brackets. The arrow on the second blot indicates high molecular weight tau complexes. The antibodies used are ADx215 (YT1.15), ADx210 (YT1.10) and the commercial phosphorylation-specific antibody AT100 (exposure time of 30 min for ADx210 (YT1.10) and AT100, and 30 sec for ADx215 (YT1.15)). B) Tau epitope sequence recognized by ADx201 (YT1.1) and ADx215 (YT1.15). C) Immunohistochemical analysis of different regions of the Tau-P301L Tg mouse using ADx215 (YT1.15) and ADX210 (YT1.10) for immunodetection.

Figure 4:
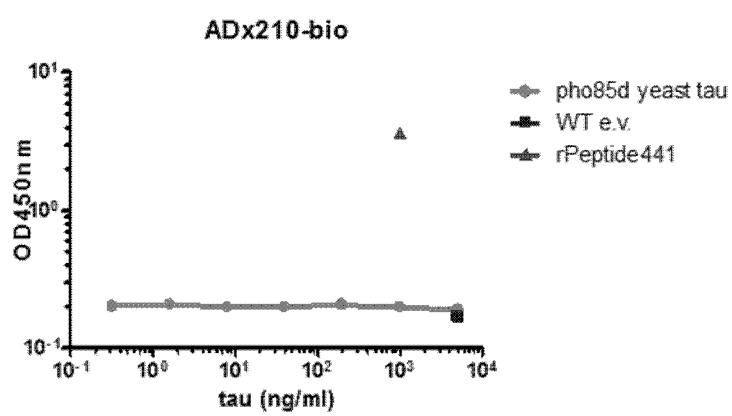
Figure 4:
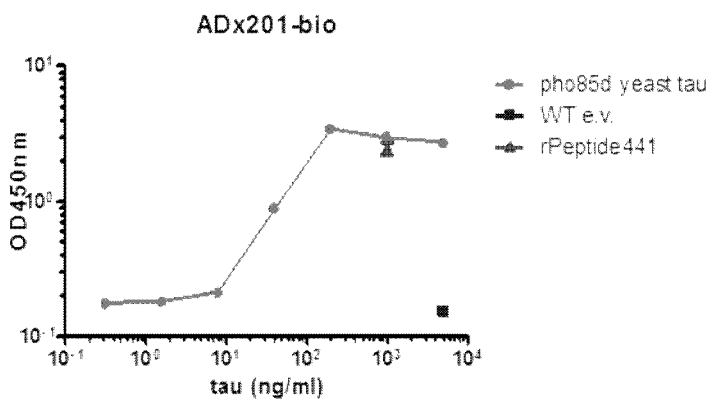

FIG. 4: Immunodetection of aggregated tau from pho85d yeast in ELISA with the pan-tau antibody ADx201 and the antibody ADx210.

FIG. 5: Epitope mapping of the monoclonal antibody ADx215. A) Visualization of the epitopes relative to different tau constructs based on Western Blot results. B) Minimal epitope recognized by the monoclonal antibody ADx215 following Pepscan.

FIG. 6 (sheets 6/11 to 11/11 of Drawings): Sequences SEQ ID NO. 1 to SEQ ID NO. 29 as referred to throughout this specification.

EXAMPLES

1. Humanized Tau Models

When purified from the humanized yeast strains, protein tau maintains its (hyper)phosphorylation status and its propensity to seed the formation of tau filaments as shown (Vandebroek et al., 2005). Mass spectrometry study confirmed 13 different phosphorylation sites in yeast-purified human tau, all of which were previously reported in AD brain (data provided by J. Gobom, U. Goteborg, Sweden; data not shown).

2. Generation of Antibodies Specific for Aggregated Tau.

Yeast-purified tau was used for the immunization of BALB/C mice. After fusion and screening of monoclonal antibodies (mAbs), 15 clones were selected based on the difference in immunoreactivity toward recombinant non-phosphorylated tau purified from bacteria and tau isolated from yeast.

3. Phosphorylation Specificity of Antibodies Specific for Aggregated Tau.

The phosphorylation specificity was initially tested on extracts obtained from the humanized wild type yeast strain and its congenic mds1Δ and pho85Δ mutants that display reduced and increased tau phosphorylation. Recombinant tau produced by *E. coli* served as control.

As shown in FIG. 2A, mAbs such as ADX210 showed an increased affinity for hyperphosphorylated tau as present in the pho85Δ mutant, where it specifically recognized high molecular weight and presumably oligomeric tau complexes. The antibody did not react with *E. coli*-produced recombinant tau, indicative for its phosphorylation dependency. In contrast, ADx215 detected both tau obtained from yeast and *E. coli* and as such this mAb displayed a similar immunoreactivity as that obtained with the commercial pan-tau mAb Tau-5, known to be phosphorylation-independent. Note, however, that ADx215 has a much higher affinity (reduced exposure time) and that it clearly recognized some of the high molecular weight tau complexes in the yeast samples.

Confirmation of the phosphorylation specificity of the novel mAbs was obtained by analysis of humanized yeast extracts treated with alkaline phosphatase as shown in FIG. 2B. The results obtained for ADX210 demonstrate that dephosphorylation leads to disassembly of the tau complexes back to the monomeric form, corroborating the hypothesis that tau (hyper)phosphorylation is required for tau aggregation.

4. Detection of Oligomeric Tau in Human Brain and Human Tau Transgenic Mice Models.

Human tau must acquire the phosphorylation epitopes and the conformational change required to drive the formation of higher order oligomeric complexes in an AD brain. Such selected Mabs, i.e ADX210 and ADx 215 can be used to stain hyperphosphorylated TAU protein neurofibrillary tangles brain regions and the high affinity mAb ADx215 can specifically detected high molecular weight tau complexes from brain extracts from late stage AD patient.

Western blot analysis of brain extracts obtained from control mice (wild type, i.e. FVB, and tau-KO) and transgenics expressing human tau-P301L demonstrated that Mabs ADx215 (YT1.15), ADx210 (YT1.10) and AT100 specifically recognized human tau and not endogenous mouse tau (data provided by F. Van Leuven, K.U.Leuven; FIG. 3A). For ADx215 (YT1.15) this result was confirmed by epitope mapping as shown in FIG. 3B. Immunohistochemical analysis revealed that two of the selected Mabs, i.e ADx210 (YT1.10) and ADx215 (YT1.15), stained tangles in different regions of the brain in aged Tg mice (data provided by F. Van Leuven, K.U.Leuven; FIG. 3C). Furthermore, the high affinity Mab ADx215 (YT1.15) specifically detected high molecular weight tau complexes in brain extracts of Tg mice (FIG. 3A) Combined these data confirmed that, when expressed in yeast, human tau must acquire the phosphorylation epitopes and the conformational change required to drive the formation of higher order oligomeric complexes as seen in AD brain.

5. Immunodetection of Aggregated Tau in ELISA.

For the preparation of an aggregated tau-specific ELISA, plates are coated with one or more different capturing antibodies specific for aggregated tau.

To perform the ELISA test, the sample to be tested is added to the plates. Optionally, as a positive control, purified aggregated tau is added to separate wells of the ELISA plate. Optionally, as a standard, known amounts of purified aggregated tau are added to separate wells of the ELISA plate. Next, after washing of the plates, bound aggregated tau is detected using a secondary antibody capable of binding to aggregated tau. This can be an antibody which recognizes total tau, such as tau-5 or HT-7, a phosphorylation-specific anti-tau antibody, such as AT270, or a second aggregated tau-specific antibody, or a combination of two or more such antibodies.

Alternatively, the capturing antibodies used to coat the plates are an antibody which recognizes total tau, such as tau-5 or HT-7, a phosphorylation-specific anti-tau antibody such as AT270, or an aggregated tau-specific antibody, or a combination of two or more such antibodies, and bound aggregated tau is detected using an aggregated tau-specific antibody or a combination of two or more such antibodies.

Binding of the secondary antibodies can be visualized by measuring activity of an enzyme coupled directly or indirectly (e.g. via streptavidin-biotin binding) to the secondary antibodies, such as alkaline phosphatase or luciferase. Alternatively, binding of the secondary antibodies can be visualized by measuring fluorescence emitted by a fluorochrome such as phycoerythrin or a fluorescent protein coupled directly or indirectly to the secondary antibodies. Also, binding of the secondary antibodies can be visualized indirectly by using tertiary antibodies binding specifically to the secondary antibodies, followed by visualization of binding of these tertiary antibodies to the secondary antibodies.

The sample to be tested can be cerebrospinal fluid (CSF), whole blood, plasma or serum, or any other sample.

A Nunc ELISA plate was coated with 100 μl/well of 5 μg/ml ADx215 for 1 hour at 37° C. Subsequently, the coatings medium was replaced with 0.5% casein in PBS for blocking (300 μl/well) at 37° C. for one hour. Meanwhile, a dilution series of pho85d yeast tau extract was prepared from 5000 ng/ml till 320 pg/ml, which was placed on the ADx215 coated plate for 1 hour at 37° C. After washing three times with 0.05% Tween20-PBS, biotinylated detection antibody (ADx201-bio or ADx210-bio, ADx201 is a pan-tau antibody) was added for 1 hour at 37° C. After three rounds of washing, streptavidine-HRP conjugate (Jackson) was placed on the plate for 30 min at 37° C. Subsequent to washing (3 times), the amount of peroxidase was measured using a H2O2/TMB substrate solution for 30 min at room temperature. Finally, the reaction was stopped with 100 μl of 1N H2SO4 and read at 450 nm.

Interpretation: This preparation of pho85d yeast tau extract did not contain enough oligomeric tau to be detected by AD210-bio.

6. Immunodetection of Aggregated Tau Using xMAP Technology.

As an alternative to ELISA, immunodetection of aggregated tau can be performed in a bead-based assay like the Luminex® xMAP® technology, allowing for simultaneous multiparametric analysis like described for the INNO-BIA AlzBio3 (Olsson et al., 2005).

For the preparation of an aggregated tau-specific xMAP® assay, beads are coated with one or more different capturing antibodies specific for aggregated tau.

To perform the xMAP® assay, the sample to be tested is added to the antibody-coated beads. Next, after washing of the beads, bound aggregated tau is detected using a secondary antibody capable of binding to aggregated tau. This can be an antibody which recognizes total tau, such as tau-5 or HT-7, a phosphorylation-specific anti-tau antibody, such as AT270, or a second aggregated tau-specific antibody, or a combination of two or more antibodies.

Alternatively, the capturing antibodies used to coat the beads are an antibody which recognizes total tau, such as tau-5 or HT-7, a phosphorylation-specific anti-tau antibody such as AT270, or an aggregated tau-specific antibody, or a combination of two or more such antibodies, and bound aggregated tau is detected using an aggregated tau-specific antibody or a combination of two or more such antibodies.

Binding of the secondary antibodies can be visualized by measuring fluorescence emitted by a fluorochrome such as phycoerythrin or a fluorescent protein coupled directly or indirectly to the secondary antibodies. Also, binding of the secondary antibodies can be visualized indirectly by using tertiary antibodies binding to the secondary antibodies, followed by visualization of binding of these tertiary antibodies.

The sample to be tested can be cerebrospinal fluid (CSF), whole blood, plasma or serum, or any other sample.

7. Diagnosis of Tauopathies Using Antibodies Specific for Aggregated Tau.

Samples of patients suffering from a tauopathy and control subjects are tested for the presence or absence of aggregated tau using the aggregated tau-specific antibodies of the invention. Aggregated tau is detected by any of the methods described above, or any other method making use of the aggregated tau-specific antibodies of the invention.

Aggregated tau can be detected in a majority x % of samples of patients suffering from a tauopathy, but only in a minority y % of samples from control subjects. The sensitivity of a diagnostic test for a tauopathy, based upon the aggregated tau as a disease marker is then x/100, while the specificity of the diagnostic test is then (100−y)/100.

As an alternative, samples of patients suffering from a tauopathy and control subjects are tested for the amount of aggregated tau using the aggregated tau-specific antibodies of the invention. Aggregated tau is quantified by any of the methods described above, or any other method making use of the aggregated tau-specific antibodies of the invention.

On average, more aggregated tau is present in samples of patients suffering from a tauopathy than in samples of control subjects. Therefore, careful selection of a threshold value above which a subject is classified as suffering from a tauopathy allows to obtain the desired sensitivity and/or specificity of the diagnostic test.

For each amount of aggregated tau measured, the sensitivity and 1-specificity is calculated for a test in which this value is the threshold value, above which a subject is classified as suffering from a tauopathy. The curve wherein for each amount of aggregated tau measured, sensitivity (Y-axis) is plotted versus 1-specificity (X-axis) is the receiver operating characteristic (ROC) curve. The threshold value for which $specificity^2 + sensitivity^2$ is closest to 1 might be considered as the best threshold value for the test. Alternatively, higher sensitivity or specificity might be desired, which is obtained by decreasing or increasing the threshold value, respectively.

8. Identification of Compositions Interfering with Tau Aggregation.

The antibodies of the present invention allow for the detection, qualification and/or quantification of aggregated tau in a sample, and thus allow to identify compositions which interfere with aggregation of tau and/or with stability of aggregated tau.

Aggregated tau can be obtained by purification from a humanized yeast model as described before (Vandebroek et al., 2005). Aggregated tau is then incubated with the composition to be tested. After incubation, the amount of aggregated tau in the incubated sample is determined using the antibodies of the invention, and compared with the amount of aggregated tau in a sample that has not been incubated with the composition. If the amount of aggregated tau in the incubated sample is different from the amount of aggregated tau in a sample that has not been incubated with the composition, it can be concluded that the tested composition has interfered with the stability of aggregated tau. An example of such composition is alkaline phosphatase, as is shown in FIG. 2B.

Tau aggregates can be formed in vitro by incubation of tau purified from a humanized yeast model as described before (Vandebroek et al., 2005). During this in vitro aggregate formation, the composition to be tested is added. After incubation, the amount of aggregated tau is determined using the antibodies of the invention, and compared with the amount of in vitro aggregated tau which was not exposed to the composition. If the amount of aggregated tau in the exposed sample is different from the amount of aggregated tau in a sample that has not been exposed to the composition, it can be concluded that the tested composition has interfered with the formation of aggregated tau.

9. Epitope Mapping of Tau Monoclonal Antibodies.

Standard techniques were used to express full size human tau, two N-terminal mutants, and one C-terminal mutant in *E. coli*. All constructs were mTNF-His6 fusions permitting control on expression by an anti-his monoclonal. Cell supernatant was run on gel and western blotted. For some of the monoclonals the epitope or region was already known (BT2, AT120 & BT3) and these monoclonals were used to control and optimize the method. Table 1 provides an overview of the location of the epitope in human Tau (full size Tau, N-terminal short Tau, N-terminal long Tau, C-terminal Tau) recognized by the monoclonal antibodies tested.

TABLE 1

| Location of the epitope in recognized by the monoclonal antibodies tested | | | | |
| --- | --- | --- | --- | --- |
| mab | full size | N-term short | N-term long | C-term |
| His6 | + | + | + | + |
| BT2 | + | − | + | + |
| YT1.1 | + | − | + | + |
| YT1.15 | + | + | + | − |
| AT120 | + | − | + | + |
| BT3 | + | + | + | − |

From these experiments we could conclude that (FIG. 5A). To further refine the epitope-mapping we conducted a Pepscan to further delineate the epitopes by testing antibodies on small overlapping peptides The amino acid sequence covering the first 163 aa of the short version of human tau were communicated to Pepscan. The sequence contains one known epitope, HT7 (Vanmechelen, E. et al., 2000) and epitopes of three antibodies, which were mapped to the N-terminus of tau, including YT 1.15, all IgG1 subtype monoclonal antibodies. Using miniPEPSCAN cards with overlapping 15-mers, epitope mapping was performed as described in Slootstra et al, 1995. As remark we have to point that for the Pepscan 10 µg/ml of the monoclonal had to be used to obtain a signal, where usually 1 ng/ml is enough. This could be due to presentation of the peptides on a fixed carrier, or can have to do with the (short) length of the peptide missing the correct conformation. The results are shown in FIG. 5B.

ADx215 (YT1.15) was identified as being aa 16-24 or GTYGLGDRK (SEQ ID NO. 27). This is a new epitope not yet described in literature. Minimal epitope requirements were confirmed on newly synthesized peptides from a source different from Pepscan. Similar to other tau antibodies (Gamblin, T. C., 2005), for optimal recognition of minimal epitope $G_{16}$-$K_{18}$, a N-terminal part of tau predicted to form an α-helix (DeLeys, R. et al., 1995) is required and thus the sequence needed in a synthetic peptide to serve as epitope for YT1.15 as a calibrator is $E_7$FEVMEDHAG$_{16}$TYGLGDRK$_{24}$ (SEQ ID NO. 29).

REFERENCE LIST (1994). Current protocols in Human Genetics., N. C. Dracapoli, J. L. Haines, B. R. Korf, D. T. Moir, C. C. Morton, C. E. Seidman, J. G. Seidman, and D. R. Smith, eds. John Wiley & Sons, Inc.).

Almagro, J. C. and Fransson, J. Humanization of antibodies. Front. Biosci. 13:1619-33., 1619-1633. Jan. 1, 2008.
Ref Type: Journal Ames, Robert S., Tornetta, Mark A., Deen, Keith, Jones, Christopher S., Swift, Ann M., and Ganguly, Subinay. Conversion of murine Fabs isolated from a combinatorial phage display library to full length immunoglobulins. Journal of Immunological Methods 184[2], 177-186. 18Aug. 1995.
Ref Type: Journal Asuni, A. A., Boutajangout, A., Quartermain, D., and Sigurdsson, E. M. Immunotherapy targeting pathological tau conformers in a tangle mouse model reduces brain pathology with associated functional improvements. J Neurosci. 27[34], 9115-9129. 22 Aug. 2007.
Ref Type: Journal Better, M., Chang, C. P., Robinson, R. R., and Horwitz, A. H. *Escherichia coli* secretion of an active chimeric antibody fragment. Science. %20; 240[4855], 1041-1043. 1988.
Ref Type: Journal Boder, E. T., Midelfort, K. S., and Wittrup, K. D. Directed evolution of antibody fragments with monovalent femtomolar antigen-binding affinity. Proc Natl Acad Sci U S. A. 97[20], 10701-10705. 26 Sep. 2000.
Ref Type: Journal Borras, L., Gunde, T., Tietz, J., Bauer, U., Hulmann-Cottier, V., Grimshaw, J. P., and Urech, D. M. Generic approach for the generation of stable humanized single-chain Fv fragments from rabbit monoclonal antibodies. J Biol Chem. %19; 285[12], 9054-9066. 2010.
Ref Type: Journal Braak, H. and Braak, E. Neuropathological stageing of Alzheimer-related changes. Acta Neuropathol. 82[4], 239-259. 1991.
Ref Type: Journal Brinkmann, Ulrich, Chowdhury, Partha S., Roscoe, Donna M., and Pastan, Ira. Phage display of disulfide-stabilized Fv fragments. Journal of Immunological Methods 182[1], 41-50. 1995.
Ref Type: Journal Buée-Scherrer, V., Condamines, O., Mourton-Gilles, C., Jakes, R., Goedert, M., Pau, B., and Delacourte, A. AD2, a phosphorylation-dependent monoclonal antibody directed against tau proteins found in Alzheimer's disease. Brain Res Mol Brain Res. 39[1-2], 79-88. 1996.
Ref Type: Journal Burton, D. R. and Barbas, C. F., III. Human antibodies from combinatorial libraries. Adv. Immunol. 57:191-280., 191-280. 1994.
Ref Type: Journal Carmel, G., Mager, E. M., Binder, L. I., and Kuret, J. The structural basis of monoclonal antibody Alz50's selectivity for Alzheimer's disease pathology. J Biol Chem 271 [51], 32789-32795. 20 Dec. 1996.
Ref Type: Journal Davies, J. and Riechmann, L. Affinity improvement of single antibody VH domains: residues in all three hypervariable regions affect antigen binding. Immunotechnology. 2[3], 169-179. 1996.

DeLeys, R. et al. Mapping and Sequence Requirements of the Phosphorylation-Sensitive Epitopes Recognized by the Monoclonal Antibodies Tau1, BT2, and AT8. Peptides in Immunology. Edited by C. H. Schneider, 1995 John Wiley & Sons. Ltd pp 239-244
Ref Type: Journal De Pascalis, R., Iwahashi, M., Tamura, M., Padlan, E. A., Gonzales, N. R., Santos, A. D., Giuliano, M., Schuck, P., Schlom, J., and Kashmiri, S. V. Grafting of "abbreviated" complementarity-determining regions containing specificity-determining residues essential for ligand contact to engineer a less immunogenic humanized monoclonal antibody. J Immunol. 169[6], 3076-3084. 15 Sep. 2002.
Ref Type: Journal Delves, P., Martin, S., Burton, D., and Roitt, I. (2006). Roitt's Essential Immunology. Wiley-Blackwell).

Drewes, G. MARKing tau for tangles and toxicity. Trends Biochem Sci. 29[10], 548-555. 2004.
Ref Type: Journal Emadi, S., Barkhordarian, H., Wang, M. S., Schulz, P., and Sierks, M. R. Isolation of a human single chain antibody fragment against oligomeric alpha-synuclein that inhibits aggregation and prevents alpha-synuclein-induced toxicity. J Mol Biol. 368[4], 1132-1144. 11 May 2007.
Ref Type: Journal Emadi, S., Kasturirangan, S., Wang, M. S., Schulz, P., and Sierks, M. R. Detecting morphologically distinct oligomeric forms of alpha-synuclein. J Biol Chem. 284[17], 11048-11058. 24 Apr. 2009.
Ref Type: Journal Furukawa, K., Shirai, H., Azuma, T., and Nakamura, H. A role of the third complementarity-determining region in the affinity maturation of an antibody. J Biol Chem. %20; 276[29], 27622-27628. 2001.

Gamblin, T. C. Potential structure/function relationships of predicted secondary structural elements of tau. Biochim. Biophys. Acta 1739, 140-149 (2005)

Ref Type: Journal
Goedert, M., Spillantini, M. G., Jakes, R., Rutherford, D., and Crowther, R. A. Multiple isoforms of human microtubule-associated protein tau: sequences and localization in neurofibrillary tangles of Alzheimer's disease. Neuron. 3[4], 519-526. 1989.
Ref Type: Journal
Gram, H., Marconi, L. A., Barbas, C. F., III, Collet, T. A., Lerner, R. A., and Kang, A. S. In vitro selection and affinity maturation of antibodies from a naive combinatorial immunoglobulin library. Proc Natl Acad Sci U S. A. 89[8], 3576-3580. 15 Apr. 1992.
Ref Type: Journal
Greenberg, S. G. and Davies, P. A preparation of Alzheimer paired helical filaments that displays distinct tau proteins by polyacrylamide gel electrophoresis. Proc. Natl. Acad. Sci. U.S.A. 87[15], 5827-5831. 1990.
Ref Type: Journal
Hamdane, M., Dourlen, P., Bretteville, A., Sambo, A. V., Ferreira, S., Ando, K., Kerdraon, O., Begard, S., Geay, L., Lippens, G., Sergeant, N., Delacourte, A., Maurage, C. A., Galas, M. C., and Buee, L. Pin1 allows for differential Tau dephosphorylation in neuronal cells. Mol Cell Neurosci. 32[1-2], 155-160. 2006.
Ref Type: Journal
Harding, F. A., Stickler, M. M., Razo, J., and DuBridge, R. B. The immunogenicity of humanized and fully human antibodies: residual immunogenicity resides in the CDR regions. MAbs. 2[3], 256-265. 2010.
Ref Type: Journal
Huston, J. S., Mudgett-Hunter, M., Tai, M. S., McCartney, J., Warren, F., Haber, E., and Oppermann, H. Protein engineering of single-chain Fv analogs and fusion proteins. Methods Enzymol. 203:46-88., 46-88. 1991.
Ref Type: Journal
Jicha, G. A., Bowser, R., Kazam, I. G., and Davies, P. Alz-50 and MC-1, a new monoclonal antibody raised to paired helical filaments, recognize conformational epitopes on recombinant tau. J Neurosci Res. 48[2], 128-132. 15 Apr. 1997.
Ref Type: Journal
Jicha, G. A., Weaver, C., Lane, E., Vianna, C., Kress, Y., Rockwood, J., and Davies, P. cAMP-dependent protein kinase phosphorylations on tau in Alzheimer's disease. J Neurosci 19[17], 7486-7494. 1 Sep. 1999.
Ref Type: Journal
Jones, P., Dear, P., Foote, J., Neuberger, M., Winter, G. Replacing the complementarity-determining regions in a human antibody with those from a mouse. Nature 321 [6069]: 522-525. 1986.
Ref Type: Journal
Josephs, K. A., Whitwell, J. L., Ahmed, Z., Shiung, M. M., Weigand, S. D., Knopman, D. S., Boeve, B. F., Parisi, J. E., Petersen, R. C., Dickson, D. W., and Jack, C. R., Jr. Beta-amyloid burden is not associated with rates of brain atrophy. Ann Neurol. 63[2], 204-212. 2008.
Ref Type: Journal
Kabat, E. A., Te Wu, T., Perry, H. M., Gottesman, K. S., and Foeller, C. (1991). Sequences of proteins of immunological interest. US Department of Health and Human Services, Public Health Service, National Institutes of Health, Bethesda).
Kashmiri, S. V., De Pascalis, R., Gonzales, N. R., and Schlom, J. SDR grafting—a new approach to antibody humanization. Methods. 36[1], 25-34. 2005.
Ref Type: Journal
Kayed, R., Canto, I., Breydo, L., Rasool, S., Lukacsovich, T., Wu, J., Albay, R., III, Pensalfini, A., Yeung, S., Head, E., Marsh, J. L., and Glabe, C. Conformation dependent monoclonal antibodies distinguish different replicating strains or conformers of prefibrillar abeta oligomers. Mol Neurodegener. 5[1], 57. 13 Dec. 2010.
Ref Type: Journal
Kettleborough, C. A., Ansell, K. H., Allen, R. W., Rosell-Vives, E., Gussow, D. H., and Bendig, M. M. Isolation of tumor cell-specific single-chain Fv from immunized mice using phage-antibody libraries and the re-construction of whole antibodies from these antibody fragments. Eur. J Immunol. 24[4], 952-958. 1994.
Ref Type: Journal
Krebs, J. E., Goldstein, E. S., and Kilpatrick, S. T. (2009). Lewin's Genes X. Jones & Bartlett Publishers).
Mandelkow, E. M., Stamer, K., Vogel, R., Thies, E., and Mandelkow, E. Clogging of axons by tau, inhibition of axonal traffic and starvation of synapses. Neurobiol. Aging. 24[8], 1079-1085. 2003.
Ref Type: Journal
Mercken, M., Vandermeeren, M., Lubke, U., Six, J., Boons, J., Van, de, V, Martin, J. J., and Gheuens, J. Monoclonal antibodies with selective specificity for Alzheimer Tau are directed against phosphatase-sensitive epitopes. Acta Neuropathol. (Berl.) 84[3], 265-272. 1992.
Ref Type: Journal
Mullinax, R. L., Gross, E. A., Hay, B. N., Amberg, J. R., Kubitz, M. M., and Sorge, J. A. Expression of a heterodimeric Fab antibody protein in one cloning step. Biotechniques. 12[6], 864-869. 1992.
Ref Type: Journal
Nelson, A. L. Antibody fragments: hope and hype. MAbs. 2[1], 77-83. 2010.
Ref Type: Journal
Novak, M., Kabat, J., and Wischik, C. M. Molecular characterization of the minimal protease resistant tau unit of the Alzheimer's disease paired helical filament. EMBO J. 12[1], 365-370. 1993.
Ref Type: Journal
Oddo, S., Vasilevko, V., Caccamo, A., Kitazawa, M., Cribbs, D. H., and LaFerla, F. M. Reduction of soluble Abeta and tau, but not soluble Abeta alone, ameliorates cognitive decline in transgenic mice with plaques and tangles. J Biol Chem. 281[51], 39413-39423. 22 Dec. 2006.
Ref Type: Journal
Olsson, A., Vanderstichele, H., Andreasen, N., De Meyer, G., Wallin, A., Holmberg, B., Rosengren, L., Vanmechelen, E., and Blennow, K. Simultaneous measurement of beta-amyloid(1-42), total tau, and phosphorylated tau (Thr181) in cerebrospinal fluid by the xMAP technology. Clin Chem 51[2], 336-345. 2005.
Ref Type: Journal
Padlan, E. A., Abergel, C., and Tipper, J. P. Identification of specificity-determining residues in antibodies. FASEB J. 9[1], 133-139. 1995.
Ref Type: Journal
Persic, L., Roberts, A., Wilton, J., Cattaneo, A., Bradbury, A., and Hoogenboom, H. R. An integrated vector system for the eukaryotic expression of antibodies or their fragments after selection from phage display libraries. Gene. 187[1], 9-18. 10 Mar. 1997.
Ref Type: Journal
Rader, C., Cheresh, D. A., and Barbas, C. F., III. A phage display approach for rapid antibody humanization: designed combinatorial V gene libraries. Proc Natl Acad Sci U S. A. 95[15], 8910-8915. 21 Jul. 1998.

Ref Type: Journal
Sambrook, J. and Russell, D. W. (2001). Molecular cloning: A Laboratory Manual., F. Ausubel, ed. (Cold Spring Harbor, N.Y.: Cold Spring Harbor Laboratory Press).
Santacruz, K., Lewis, J., Spires, T., Paulson, J., Kotilinek, L., Ingelsson, M., Guimaraes, A., DeTure, M., Ramsden, M., McGowan, E., Forster, C., Yue, M., Orne, J., Janus, C., Mariash, A., Kuskowski, M., Hyman, B., Hutton, M., and Ashe, K. H. Tau suppression in a neurodegenerative mouse model improves memory function. Science. 309 [5733], 476-481. 15 Jul. 2005.
Ref Type: Journal
Sawai, H., Yamasaki, N., Shigeta, M., Komori, S., Karasuyama, H., Koyama, K., and Isojima, S. Direct production of the Fab fragment derived from the sperm immobilizing antibody using polymerase chain reaction and cDNA expression vectors. Am J Reprod. Immunol. 34[1], 26-34. 1995.
Ref Type: Journal
Short, M. K., Krykbaev, R. A., Jeffrey, P. D., and Margolies, M. N. Complementary combining site contact residue mutations of the anti-digoxin Fab 26-10 permit high affinity wild-type binding. J Biol Chem. 277[19], 16365-16370. 10 May 2002.
Ref Type: Journal
Shu, L., Qi, C. F., Schlom, J., and Kashmiri, S. V. Secretion of a single-gene-encoded immunoglobulin from myeloma cells. Proc Natl Acad Sci U S. A. 90[17], 7995-7999. 1 Sep. 1993.
Ref Type: Journal
Sigurdsson, E. M. Immunotherapy targeting pathological tau protein in Alzheimer's disease and related tauopathies. J Alzheimers. Dis. 15[2], 157-168. 2008.
Ref Type: Journal
Skerra, A. and Pluckthun, A. Assembly of a functional immunoglobulin Fv fragment in *Escherichia coli*. Science. %20; 240[4855], 1038-1041. 1988.
Slootstra, J. W. et al. Screening of a small set of random peptides: a new strategy to identify synthetic peptides that mimic epitopes. J Mol Recognit. 10, 217-224 (1997)
Ref Type: Journal
Tarawneh, R. and Holtzman, D. M. Critical issues for successful immunotherapy in Alzheimer's disease: development of biomarkers and methods for early detection and intervention. CNS. Neurol Disord. Drug Targets. 8[2], 144-159. 2009.
Ref Type: Journal
Tarditi, A., Caricasole, A., and Terstappen, G. Therapeutic targets for Alzheimer's disease. Expert Opin. Ther Targets. 13[5], 551-567. 2009.
Ref Type: Journal
Thompson, J., Pope, T., Tung, J. S., Chan, C., Hollis, G., Mark, G., and Johnson, K. S. Affinity maturation of a high-affinity human monoclonal antibody against the third hypervariable loop of human immunodeficiency virus: use of phage display to improve affinity and broaden strain reactivity. J Mol Biol. 256[1], 77-88. 16 Feb. 1996.
Ref Type: Journal
van Berckel, B. N. and Scheltens, P. Getting a grip on Alzheimer's disease: imaging amyloid in the brain. Lancet Neurol. 6[3], 204-206. 2007.
Ref Type: Journal
Vandebroek, T., Terwel, D., Vanhelmont, T., Gysemans, M., Van Haesendonck, C., Engelborghs, Y., Winderickx, J., and Van Leuven, F. Microtubule binding and clustering of human Tau-4R and Tau-P301L proteins isolated from yeast deficient in orthologues of glycogen synthase kinase-3beta or cdk5. J Biol Chem. 281[35], 25388-25397. 1 Sep. 2006.
Ref Type: Journal
Vandebroek, T., Vanhelmont, T., Terwel, D., Borghgraef, P., Lemaire, K., Snauwaert, J., Wera, S., Van Leuven, F., and Winderickx, J. Identification and isolation of a hyperphosphorylated, conformationally changed intermediate of human protein tau expressed in yeast. Biochemistry. 44[34], 11466-11475. 30 Aug. 2005.
Ref Type: Journal
Vanhelmont, T., Vandebroek, T., De Vos, A., Terwel, D., Lemaire, K., Anandhakumar, J., Franssens, V., Swinnen, E., Van Leuven, F., and Winderickx, J. Serine-409 phosphorylation and oxidative damage define aggregation of human protein tau in yeast. FEMS. Yeast. Res. 10[8], 992-1005. 2010.
Vanmechelen, E. et al. Quantification of tau phosphorylated at threonine 181 in human cerebrospinal fluid: a sandwich ELISA with a synthetic phosphopeptide for standardization. Neurosci Lett 285, 49-52 (2000
Ref Type: Journal
Vaughan, T. J., Osbourn, J. K., and Tempest, P. R. Human antibodies by design. Nat Biotechnol. 16[6], 535-539. 1998.
Ref Type: Journal
Vechterova, L., Kontsekova, E., Zilka, N., Ferencik, M., Ravid, R., and Novak, M. DC11: a novel monoclonal antibody revealing Alzheimer's disease-specific tau epitope. Neuroreport. %20; 14[1], 87-91. 2003.
Ref Type: Journal
Vincke, C., Loris, R., Saerens, D., Martinez-Rodriguez, S., Muyldermans, S., and Conrath, K. General strategy to humanize a camelid single-domain antibody and identification of a universal humanized nanobody scaffold. J Biol Chem. 284[5], 3273-3284. 30 Jan. 2009.
Ref Type: Journal
Weiner, H. L. and Frenkel, D. Immunology and immunotherapy of Alzheimer's disease. Nat Rev Immunol. 6[5], 404-416. 2006.
Ref Type: Journal
Yang, W. P., Green, K., Pinz-Sweeney, S., Briones, A. T., Burton, D. R., and Barbas, C. F., III. CDR walking mutagenesis for the affinity maturation of a potent human anti-HIV-1 antibody into the picomolar range. J Mol Biol. 254[3], 392-403. 1 Dec. 1995.
Ref Type: Journal
Zheng-Fischhofer, Q., Biernat, J., Mandelkow, E. M., Illenberger, S., Godemann, R., and Mandelkow, E. Sequential phosphorylation of Tau by glycogen synthase kinase-3beta and protein kinase A at Thr212 and Ser214 generates the Alzheimer-specific epitope of antibody AT100 and requires a paired-helical-filament-like conformation. Eur J Biochem 252[3], 542-552. 15 Mar. 1998.
Ref Type: Journal

| Sequence Listing Free Text | |
|---|---|
| SEQ ID NO. 10 | ADx210 CDR of the light chain variable region |
| SEQ ID NO. 11 | ADx210 CDR of the light chain variable region |
| SEQ ID NO. 12 | ADx210 CDR of the light chain variable region |
| SEQ ID NO. 13 | ADx210 CDR of the light chain variable region |
| SEQ ID NO. 14 | ADx210 CDR of the light chain variable region |
| SEQ ID NO. 15 | Heavy chain variable region of ADx210 |
| SEQ ID NO. 16 | Light chain variable region of ADx210 |
| SEQ ID NO. 17 | subpart of the Heavy chain variable region of ADx210 |
| SEQ ID NO. 18 | Light chain variable region of an isoform of ADx210 |

| Sequence Listing Free Text | |
|---|---|
| SEQ ID NO. 19 | ADx215 CDR of the heavy chain variable region |
| SEQ ID NO. 20 | ADx215 CDR of the heavy chain variable region |
| SEQ ID NO. 21 | ADx215 CDR of the heavy chain variable region |
| SEQ ID NO. 22 | ADx215 CDR of the light chain variable region |
| SEQ ID NO. 23 | ADx215 CDR of the light chain variable region |
| SEQ ID NO. 24 | ADx215 CDR of the light chain variable region |
| SEQ ID NO. 25 | ADx215 CDR of the light chain variable region |
| SEQ ID NO. 26 | ADx215 CDR of the light chain variable region |
| SEQ ID NO. 27 | Tau epitope recognized by ADx215 |
| SEQ ID NO. 28 | Tau epitope recognized by ADx215 |
| SEQ ID NO. 29 | Tau epitope recognized by ADx215 |
| SEQ ID NO. 30 | Tau epitope recognized by ADx201 |
| SEQ ID NO. 31 | Tau epitope |
| SEQ ID NO. 32 | Tau epitope |
| SEQ ID NO. 33 | Tau epitope |
| SEQ ID NO. 34 | Tau epitope |
| SEQ ID NO. 35 | Tau epitope |
| SEQ ID NO. 36 | Tau epitope |
| SEQ ID NO. 37 | Tau epitope |
| SEQ ID NO. 38 | Tau epitope |
| SEQ ID NO. 39 | Tau epitope |
| SEQ ID NO. 40 | Tau epitope |
| SEQ ID NO. 41 | Tau epitope |
| SEQ ID NO. 42 | Tau epitope |
| SEQ ID NO. 43 | Tau epitope |
| SEQ ID NO. 44 | Tau epitope |
| SEQ ID NO. 45 | Tau epitope |
| SEQ ID NO. 46 | Tau epitope |
| SEQ ID NO. 47 | Tau epitope |
| SEQ ID NO. 48 | Tau epitope |
| SEQ ID NO. 49 | Tau epitope |
| SEQ ID NO. 50 | Tau epitope |
| SEQ ID NO. 51 | Tau epitope |
| SEQ ID NO. 52 | RGD peptide |
| SEQ ID NO. 53 | RGD peptide |

The invention claimed is:

1. An isolated tau antibody, antibody-like scaffold or antibody fragment comprising a light chain variable region that comprises in a CDR1 region an amino acid sequence as set out in SEQ ID NO: 22, in a CDR2 region an amino acid sequence as set out in SEQ ID NO: 23, and in a CDR3 region an amino acid sequence as set out in SEQ ID NO: 24; and a heavy chain variable region that comprises in a CDR1 region an amino acid sequence as set out in SEQ ID NO: 19, in a CDR2 region an amino acid sequence as set out in SEQ ID NO: 20 and in a CDR3 region an amino acid sequence as set out in SEQ ID NO: 21.

* * * * *

SEQUENCE LISTING

```
<160> NUMBER OF SEQ ID NOS: 53

<210> SEQ ID NO 1
<211> LENGTH: 758
<212> TYPE: PRT
<213> ORGANISM: Homo Sapiens

<400> SEQUENCE: 1

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Glu Ser Pro Leu
            35                  40                  45

Gln Thr Pro Thr Glu Asp Gly Ser Glu Glu Pro Gly Ser Glu Thr Ser
        50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Glu Pro Glu Ser
        115                 120                 125

Gly Lys Val Val Gln Glu Gly Phe Leu Arg Glu Pro Gly Pro Pro Gly
    130                 135                 140

Leu Ser His Gln Leu Met Ser Gly Met Pro Gly Ala Pro Leu Leu Pro
145                 150                 155                 160

Glu Gly Pro Arg Glu Ala Thr Arg Gln Pro Ser Gly Thr Gly Pro Glu
                165                 170                 175

Asp Thr Glu Gly Gly Arg His Ala Pro Glu Leu Leu Lys His Gln Leu
            180                 185                 190

Leu Gly Asp Leu His Gln Glu Gly Pro Pro Leu Lys Gly Ala Gly Gly
        195                 200                 205

Lys Glu Arg Pro Gly Ser Lys Glu Glu Val Asp Glu Asp Arg Asp Val
    210                 215                 220

Asp Glu Ser Ser Pro Gln Asp Ser Pro Pro Ser Lys Ala Ser Pro Ala
225                 230                 235                 240
```

-continued

```
Gln Asp Gly Arg Pro Pro Gln Thr Ala Ala Arg Glu Ala Thr Ser Ile
            245                 250                 255

Pro Gly Phe Pro Ala Glu Gly Ala Ile Pro Leu Pro Val Asp Phe Leu
        260                 265                 270

Ser Lys Val Ser Thr Glu Ile Pro Ala Ser Glu Pro Asp Gly Pro Ser
    275                 280                 285

Val Gly Arg Ala Lys Gly Gln Asp Ala Pro Leu Glu Phe Thr Phe His
290                 295                 300

Val Glu Ile Thr Pro Asn Val Gln Lys Glu Gln Ala His Ser Glu Glu
305                 310                 315                 320

His Leu Gly Arg Ala Ala Phe Pro Gly Ala Pro Gly Glu Gly Pro Glu
                325                 330                 335

Ala Arg Gly Pro Ser Leu Gly Glu Asp Thr Lys Glu Ala Asp Leu Pro
            340                 345                 350

Glu Pro Ser Glu Lys Gln Pro Ala Ala Ala Pro Arg Gly Lys Pro Val
        355                 360                 365

Ser Arg Val Pro Gln Leu Lys Ala Arg Met Val Ser Lys Ser Lys Asp
    370                 375                 380

Gly Thr Gly Ser Asp Asp Lys Lys Ala Lys Thr Ser Thr Arg Ser Ser
385                 390                 395                 400

Ala Lys Thr Leu Lys Asn Arg Pro Cys Leu Ser Pro Lys His Pro Thr
                405                 410                 415

Pro Gly Ser Ser Asp Pro Leu Ile Gln Pro Ser Ser Pro Ala Val Cys
            420                 425                 430

Pro Glu Pro Pro Ser Ser Pro Lys Tyr Val Ser Ser Val Thr Ser Arg
        435                 440                 445

Thr Gly Ser Ser Gly Ala Lys Glu Met Lys Leu Lys Gly Ala Asp Gly
    450                 455                 460

Lys Thr Lys Ile Ala Thr Pro Arg Gly Ala Ala Pro Pro Gly Gln Lys
465                 470                 475                 480

Gly Gln Ala Asn Ala Thr Arg Ile Pro Ala Lys Thr Pro Pro Ala Pro
                485                 490                 495

Lys Thr Pro Pro Ser Ser Gly Glu Pro Pro Lys Ser Gly Asp Arg Ser
            500                 505                 510

Gly Tyr Ser Ser Pro Gly Ser Pro Gly Thr Pro Gly Ser Arg Ser Arg
        515                 520                 525

Thr Pro Ser Leu Pro Thr Pro Pro Thr Arg Glu Pro Lys Lys Val Ala
    530                 535                 540

Val Val Arg Thr Pro Pro Lys Ser Pro Ser Ser Ala Lys Ser Arg Leu
545                 550                 555                 560

Gln Thr Ala Pro Val Pro Met Pro Asp Leu Lys Asn Val Lys Ser Lys
                565                 570                 575

Ile Gly Ser Thr Glu Asn Leu Lys His Gln Pro Gly Gly Gly Lys Val
            580                 585                 590

Gln Ile Ile Asn Lys Lys Leu Asp Leu Ser Asn Val Gln Ser Lys Cys
        595                 600                 605

Gly Ser Lys Asp Asn Ile Lys His Val Pro Gly Gly Gly Ser Val Gln
    610                 615                 620

Ile Val Tyr Lys Pro Val Asp Leu Ser Lys Val Thr Ser Lys Cys Gly
625                 630                 635                 640

Ser Leu Gly Asn Ile His His Lys Pro Gly Gly Gly Gln Val Glu Val
                645                 650                 655
```

```
Lys Ser Glu Lys Leu Asp Phe Lys Asp Arg Val Gln Ser Lys Ile Gly
            660                 665                 670

Ser Leu Asp Asn Ile Thr His Val Pro Gly Gly Asn Lys Lys Ile
        675                 680                 685

Glu Thr His Lys Leu Thr Phe Arg Glu Asn Ala Lys Ala Lys Thr Asp
        690                 695                 700

His Gly Ala Glu Ile Val Tyr Lys Ser Pro Val Val Ser Gly Asp Thr
705                 710                 715                 720

Ser Pro Arg His Leu Ser Asn Val Ser Ser Thr Gly Ser Ile Asp Met
            725                 730                 735

Val Asp Ser Pro Gln Leu Ala Thr Leu Ala Asp Glu Val Ser Ala Ser
            740                 745                 750

Leu Ala Lys Gln Gly Leu
            755

<210> SEQ ID NO 2
<211> LENGTH: 441
<212> TYPE: PRT
<213> ORGANISM: Homo Sapiens

<400> SEQUENCE: 2

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Pro Thr Arg Glu Pro Lys
    210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270
```

```
Gly Lys Val Gln Ile Ile Asn Lys Lys Leu Asp Leu Ser Asn Val Gln
            275                 280                 285

Ser Lys Cys Gly Ser Lys Asp Asn Ile Lys His Val Pro Gly Gly Gly
        290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
                325                 330                 335

Val Glu Val Lys Ser Glu Lys Leu Asp Phe Lys Asp Arg Val Gln Ser
            340                 345                 350

Lys Ile Gly Ser Leu Asp Asn Ile Thr His Val Pro Gly Gly Gly Asn
                355                 360                 365

Lys Lys Ile Glu Thr His Lys Leu Thr Phe Arg Glu Asn Ala Lys Ala
370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
                405                 410                 415

Ile Asp Met Val Asp Ser Pro Gln Leu Ala Thr Leu Ala Asp Glu Val
                420                 425                 430

Ser Ala Ser Leu Ala Lys Gln Gly Leu
            435                 440

<210> SEQ ID NO 3
<211> LENGTH: 383
<212> TYPE: PRT
<213> ORGANISM: Homo Sapiens

<400> SEQUENCE: 3

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Ala Glu Glu Ala
        35                  40                  45

Gly Ile Gly Asp Thr Pro Ser Leu Glu Asp Glu Ala Ala Gly His Val
    50                  55                  60

Thr Gln Ala Arg Met Val Ser Lys Ser Lys Asp Gly Thr Gly Ser Asp
65                  70                  75                  80

Asp Lys Lys Ala Lys Gly Ala Asp Gly Lys Thr Lys Ile Ala Thr Pro
                85                  90                  95

Arg Gly Ala Ala Pro Pro Gly Gln Lys Gly Gln Ala Asn Ala Thr Arg
            100                 105                 110

Ile Pro Ala Lys Thr Pro Pro Ala Pro Lys Thr Pro Pro Ser Ser Gly
        115                 120                 125

Glu Pro Pro Lys Ser Gly Asp Arg Ser Gly Tyr Ser Ser Pro Gly Ser
    130                 135                 140

Pro Gly Thr Pro Gly Ser Arg Ser Arg Thr Pro Ser Leu Pro Thr Pro
145                 150                 155                 160

Pro Thr Arg Glu Pro Lys Lys Val Ala Val Val Arg Thr Pro Pro Lys
                165                 170                 175

Ser Pro Ser Ser Ala Lys Ser Arg Leu Gln Thr Ala Pro Val Pro Met
            180                 185                 190

Pro Asp Leu Lys Asn Val Lys Ser Lys Ile Gly Ser Thr Glu Asn Leu
```

```
            195                 200                 205
Lys His Gln Pro Gly Gly Lys Val Gln Ile Ile Asn Lys Lys Leu
210                 215                 220

Asp Leu Ser Asn Val Gln Ser Lys Cys Gly Ser Lys Asp Asn Ile Lys
225                 230                 235                 240

His Val Pro Gly Gly Gly Ser Val Gln Ile Val Tyr Lys Pro Val Asp
                245                 250                 255

Leu Ser Lys Val Thr Ser Lys Cys Gly Ser Leu Gly Asn Ile His His
                260                 265                 270

Lys Pro Gly Gly Gly Gln Val Glu Val Lys Ser Glu Lys Leu Asp Phe
                275                 280                 285

Lys Asp Arg Val Gln Ser Lys Ile Gly Ser Leu Asp Asn Ile Thr His
290                 295                 300

Val Pro Gly Gly Gly Asn Lys Lys Ile Glu Thr His Lys Leu Thr Phe
305                 310                 315                 320

Arg Glu Asn Ala Lys Ala Lys Thr Asp His Gly Ala Glu Ile Val Tyr
                325                 330                 335

Lys Ser Pro Val Val Ser Gly Asp Thr Ser Pro Arg His Leu Ser Asn
                340                 345                 350

Val Ser Ser Thr Gly Ser Ile Asp Met Val Asp Ser Pro Gln Leu Ala
                355                 360                 365

Thr Leu Ala Asp Glu Val Ser Ala Ser Leu Ala Lys Gln Gly Leu
370                 375                 380

<210> SEQ ID NO 4
<211> LENGTH: 352
<212> TYPE: PRT
<213> ORGANISM: Homo Sapiens

<400> SEQUENCE: 4

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Ala Glu Glu Ala
            35                  40                  45

Gly Ile Gly Asp Thr Pro Ser Leu Glu Asp Glu Ala Ala Gly His Val
        50                  55                  60

Thr Gln Ala Arg Met Val Ser Lys Ser Lys Asp Gly Thr Gly Ser Asp
65                  70                  75                  80

Asp Lys Lys Ala Lys Gly Ala Asp Gly Lys Thr Lys Ile Ala Thr Pro
                85                  90                  95

Arg Gly Ala Ala Pro Pro Gly Gln Lys Gly Gln Ala Asn Ala Thr Arg
            100                 105                 110

Ile Pro Ala Lys Thr Pro Pro Ala Pro Lys Thr Pro Pro Ser Ser Gly
        115                 120                 125

Glu Pro Pro Lys Ser Gly Asp Arg Ser Gly Tyr Ser Ser Pro Gly Ser
130                 135                 140

Pro Gly Thr Pro Gly Ser Arg Ser Arg Thr Pro Ser Leu Pro Thr Pro
145                 150                 155                 160

Pro Thr Arg Glu Pro Lys Lys Val Ala Val Val Arg Thr Pro Pro Lys
                165                 170                 175

Ser Pro Ser Ser Ala Lys Ser Arg Leu Gln Thr Ala Pro Val Pro Met
            180                 185                 190
```

```
Pro Asp Leu Lys Asn Val Lys Ser Lys Ile Gly Ser Thr Glu Asn Leu
            195                 200                 205

Lys His Gln Pro Gly Gly Lys Val Gln Ile Val Tyr Lys Pro Val
    210                 215                 220

Asp Leu Ser Lys Val Thr Ser Lys Cys Gly Ser Leu Gly Asn Ile His
225                 230                 235                 240

His Lys Pro Gly Gly Gly Gln Val Glu Val Lys Ser Glu Lys Leu Asp
                245                 250                 255

Phe Lys Asp Arg Val Gln Ser Lys Ile Gly Ser Leu Asp Asn Ile Thr
                260                 265                 270

His Val Pro Gly Gly Gly Asn Lys Lys Ile Glu Thr His Lys Leu Thr
            275                 280                 285

Phe Arg Glu Asn Ala Lys Ala Lys Thr Asp His Gly Ala Glu Ile Val
    290                 295                 300

Tyr Lys Ser Pro Val Val Ser Gly Asp Thr Ser Pro Arg His Leu Ser
305                 310                 315                 320

Asn Val Ser Ser Thr Gly Ser Ile Asp Met Val Asp Ser Pro Gln Leu
                325                 330                 335

Ala Thr Leu Ala Asp Glu Val Ser Ala Ser Leu Ala Lys Gln Gly Leu
            340                 345                 350

<210> SEQ ID NO 5
<211> LENGTH: 412
<212> TYPE: PRT
<213> ORGANISM: Homo Sapiens

<400> SEQUENCE: 5

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Ala Glu Ala Gly Ile Gly
65                  70                  75                  80

Asp Thr Pro Ser Leu Glu Asp Glu Ala Ala Gly His Val Thr Gln Ala
                85                  90                  95

Arg Met Val Ser Lys Ser Lys Asp Gly Thr Gly Ser Asp Asp Lys Lys
            100                 105                 110

Ala Lys Gly Ala Asp Gly Lys Thr Lys Ile Ala Thr Pro Arg Gly Ala
        115                 120                 125

Ala Pro Pro Gly Gln Lys Gly Gln Ala Asn Ala Thr Arg Ile Pro Ala
    130                 135                 140

Lys Thr Pro Pro Ala Pro Lys Thr Pro Ser Ser Gly Glu Pro Pro
145                 150                 155                 160

Lys Ser Gly Asp Arg Ser Gly Tyr Ser Ser Pro Gly Ser Pro Gly Thr
                165                 170                 175

Pro Gly Ser Arg Ser Arg Thr Pro Ser Leu Pro Thr Pro Pro Thr Arg
            180                 185                 190

Glu Pro Lys Lys Val Ala Val Val Arg Thr Pro Pro Lys Ser Pro Ser
        195                 200                 205

Ser Ala Lys Ser Arg Leu Gln Thr Ala Pro Val Pro Met Pro Asp Leu
    210                 215                 220
```

-continued

```
Lys Asn Val Lys Ser Lys Ile Gly Ser Thr Glu Asn Leu Lys His Gln
225                 230                 235                 240

Pro Gly Gly Gly Lys Val Gln Ile Ile Asn Lys Lys Leu Asp Leu Ser
            245                 250                 255

Asn Val Gln Ser Lys Cys Gly Ser Lys Asp Asn Ile Lys His Val Pro
        260                 265                 270

Gly Gly Gly Ser Val Gln Ile Val Tyr Lys Pro Val Asp Leu Ser Lys
    275                 280                 285

Val Thr Ser Lys Cys Gly Ser Leu Gly Asn Ile His His Lys Pro Gly
290                 295                 300

Gly Gly Gln Val Glu Val Lys Ser Glu Lys Leu Asp Phe Lys Asp Arg
305                 310                 315                 320

Val Gln Ser Lys Ile Gly Ser Leu Asp Asn Ile Thr His Val Pro Gly
                325                 330                 335

Gly Gly Asn Lys Lys Ile Glu Thr His Lys Leu Thr Phe Arg Glu Asn
            340                 345                 350

Ala Lys Ala Lys Thr Asp His Gly Ala Glu Ile Val Tyr Lys Ser Pro
        355                 360                 365

Val Val Ser Gly Asp Thr Ser Pro Arg His Leu Ser Asn Val Ser Ser
370                 375                 380

Thr Gly Ser Ile Asp Met Val Asp Ser Pro Gln Leu Ala Thr Leu Ala
385                 390                 395                 400

Asp Glu Val Ser Ala Ser Leu Ala Lys Gln Gly Leu
                405                 410

<210> SEQ ID NO 6
<211> LENGTH: 776
<212> TYPE: PRT
<213> ORGANISM: Homo Sapiens

<400> SEQUENCE: 6

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Glu Pro Glu Ser
        115                 120                 125

Gly Lys Val Val Gln Glu Gly Phe Leu Arg Glu Pro Gly Pro Pro Gly
    130                 135                 140

Leu Ser His Gln Leu Met Ser Gly Met Pro Gly Ala Pro Leu Leu Pro
145                 150                 155                 160

Glu Gly Pro Arg Glu Ala Thr Arg Gln Pro Ser Gly Thr Gly Pro Glu
                165                 170                 175

Asp Thr Glu Gly Gly Arg His Ala Pro Glu Leu Leu Lys His Gln Leu
```

```
                    180                 185                 190
Leu Gly Asp Leu His Gln Glu Gly Pro Pro Leu Lys Gly Ala Gly Gly
            195                 200                 205

Lys Glu Arg Pro Gly Ser Lys Glu Val Asp Glu Asp Arg Asp Val
    210                 215                 220

Asp Glu Ser Ser Pro Gln Asp Ser Pro Ser Lys Ala Ser Pro Ala
225                 230                 235                 240

Gln Asp Gly Arg Pro Pro Gln Thr Ala Ala Arg Glu Ala Thr Ser Ile
                245                 250                 255

Pro Gly Phe Pro Ala Glu Gly Ala Ile Pro Leu Pro Val Asp Phe Leu
            260                 265                 270

Ser Lys Val Ser Thr Glu Ile Pro Ala Ser Glu Pro Asp Gly Pro Ser
            275                 280                 285

Val Gly Arg Ala Lys Gly Gln Asp Ala Pro Leu Glu Phe Thr Phe His
            290                 295                 300

Val Glu Ile Thr Pro Asn Val Gln Lys Glu Gln Ala His Ser Glu Glu
305                 310                 315                 320

His Leu Gly Arg Ala Ala Phe Pro Gly Ala Pro Gly Glu Gly Pro Glu
                325                 330                 335

Ala Arg Gly Pro Ser Leu Gly Glu Asp Thr Lys Glu Ala Asp Leu Pro
            340                 345                 350

Glu Pro Ser Glu Lys Gln Pro Ala Ala Ala Pro Arg Gly Lys Pro Val
            355                 360                 365

Ser Arg Val Pro Gln Leu Lys Ala Arg Met Val Ser Lys Ser Lys Asp
            370                 375                 380

Gly Thr Gly Ser Asp Asp Lys Lys Ala Lys Thr Ser Thr Arg Ser Ser
385                 390                 395                 400

Ala Lys Thr Leu Lys Asn Arg Pro Cys Leu Ser Pro Lys His Pro Thr
                405                 410                 415

Pro Gly Ser Ser Asp Pro Leu Ile Gln Pro Ser Ser Pro Ala Val Cys
            420                 425                 430

Pro Glu Pro Pro Ser Ser Pro Lys Tyr Val Ser Ser Val Thr Ser Arg
            435                 440                 445

Thr Gly Ser Ser Gly Ala Lys Glu Met Lys Leu Lys Gly Ala Asp Gly
            450                 455                 460

Lys Thr Lys Ile Ala Thr Pro Arg Gly Ala Ala Pro Gly Gln Lys
465                 470                 475                 480

Gly Gln Ala Asn Ala Thr Arg Ile Pro Ala Lys Thr Pro Pro Ala Pro
                485                 490                 495

Lys Thr Pro Pro Ser Ser Ala Thr Lys Gln Val Gln Arg Arg Pro Pro
            500                 505                 510

Pro Ala Gly Pro Arg Ser Glu Arg Gly Glu Pro Pro Lys Ser Gly Asp
            515                 520                 525

Arg Ser Gly Tyr Ser Ser Pro Gly Ser Pro Gly Thr Pro Gly Ser Arg
            530                 535                 540

Ser Arg Thr Pro Ser Leu Pro Thr Pro Pro Thr Arg Glu Pro Lys Lys
545                 550                 555                 560

Val Ala Val Val Arg Thr Pro Pro Lys Ser Pro Ser Ser Ala Lys Ser
                565                 570                 575

Arg Leu Gln Thr Ala Pro Val Pro Met Pro Asp Leu Lys Asn Val Lys
            580                 585                 590

Ser Lys Ile Gly Ser Thr Glu Asn Leu Lys His Gln Pro Gly Gly Gly
            595                 600                 605
```

-continued

Lys Val Gln Ile Ile Asn Lys Leu Asp Leu Ser Asn Val Gln Ser
            610                 615                 620

Lys Cys Gly Ser Lys Asp Asn Ile Lys His Val Pro Gly Gly Ser
625                 630                 635                 640

Val Gln Ile Val Tyr Lys Pro Val Asp Leu Ser Lys Val Thr Ser Lys
                645                 650                 655

Cys Gly Ser Leu Gly Asn Ile His His Lys Pro Gly Gly Gln Val
            660                 665                 670

Glu Val Lys Ser Glu Lys Leu Asp Phe Lys Asp Arg Val Gln Ser Lys
            675                 680                 685

Ile Gly Ser Leu Asp Asn Ile Thr His Val Pro Gly Gly Asn Lys
            690                 695                 700

Lys Ile Glu Thr His Lys Leu Thr Phe Arg Glu Asn Ala Lys Ala Lys
705                 710                 715                 720

Thr Asp His Gly Ala Glu Ile Val Tyr Lys Ser Pro Val Val Ser Gly
                725                 730                 735

Asp Thr Ser Pro Arg His Leu Ser Asn Val Ser Ser Thr Gly Ser Ile
            740                 745                 750

Asp Met Val Asp Ser Pro Gln Leu Ala Thr Leu Ala Asp Glu Val Ser
            755                 760                 765

Ala Ser Leu Ala Lys Gln Gly Leu
            770                 775

<210> SEQ ID NO 7
<211> LENGTH: 381
<212> TYPE: PRT
<213> ORGANISM: Homo Sapiens

<400> SEQUENCE: 7

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Ala Glu Ala Gly Ile Gly
65                  70                  75                  80

Asp Thr Pro Ser Leu Glu Asp Glu Ala Ala Gly His Val Thr Gln Ala
                85                  90                  95

Arg Met Val Ser Lys Ser Lys Asp Gly Thr Gly Ser Asp Asp Lys Lys
            100                 105                 110

Ala Lys Gly Ala Asp Gly Lys Thr Lys Ile Ala Thr Pro Arg Gly Ala
        115                 120                 125

Ala Pro Pro Gly Gln Lys Gly Gln Ala Asn Ala Thr Arg Ile Pro Ala
    130                 135                 140

Lys Thr Pro Pro Ala Pro Lys Thr Pro Pro Ser Ser Gly Glu Pro Pro
145                 150                 155                 160

Lys Ser Gly Asp Arg Ser Gly Tyr Ser Ser Pro Gly Ser Pro Gly Thr
                165                 170                 175

Pro Gly Ser Arg Ser Arg Thr Pro Ser Leu Pro Thr Pro Pro Thr Arg
            180                 185                 190

Glu Pro Lys Lys Val Ala Val Val Arg Thr Pro Pro Lys Ser Pro Ser

```
                195                 200                 205
Ser Ala Lys Ser Arg Leu Gln Thr Ala Pro Val Pro Met Pro Asp Leu
210                 215                 220
Lys Asn Val Lys Ser Lys Ile Gly Ser Thr Glu Asn Leu Lys His Gln
225                 230                 235                 240
Pro Gly Gly Gly Lys Val Gln Ile Val Tyr Lys Pro Val Asp Leu Ser
                245                 250                 255
Lys Val Thr Ser Lys Cys Gly Ser Leu Gly Asn Ile His His Lys Pro
            260                 265                 270
Gly Gly Gly Gln Val Glu Val Lys Ser Glu Lys Leu Asp Phe Lys Asp
            275                 280                 285
Arg Val Gln Ser Lys Ile Gly Ser Leu Asp Asn Ile Thr His Val Pro
        290                 295                 300
Gly Gly Gly Asn Lys Lys Ile Glu Thr His Lys Leu Thr Phe Arg Glu
305                 310                 315                 320
Asn Ala Lys Ala Lys Thr Asp His Gly Ala Glu Ile Val Tyr Lys Ser
                325                 330                 335
Pro Val Val Ser Gly Asp Thr Ser Pro Arg His Leu Ser Asn Val Ser
            340                 345                 350
Ser Thr Gly Ser Ile Asp Met Val Asp Ser Pro Gln Leu Ala Thr Leu
            355                 360                 365
Ala Asp Glu Val Ser Ala Ser Leu Ala Lys Gln Gly Leu
        370                 375                 380

<210> SEQ ID NO 8
<211> LENGTH: 410
<212> TYPE: PRT
<213> ORGANISM: Homo Sapiens

<400> SEQUENCE: 8

Met Ala Glu Pro Arg Gln Glu Phe Glu Val Met Glu Asp His Ala Gly
1               5                   10                  15
Thr Tyr Gly Leu Gly Asp Arg Lys Asp Gln Gly Gly Tyr Thr Met His
            20                  25                  30
Gln Asp Gln Glu Gly Asp Thr Asp Ala Gly Leu Lys Glu Ser Pro Leu
        35                  40                  45
Gln Thr Pro Thr Glu Asp Gly Ser Glu Glu Pro Gly Ser Glu Thr Ser
    50                  55                  60
Asp Ala Lys Ser Thr Pro Thr Ala Glu Asp Val Thr Ala Pro Leu Val
65                  70                  75                  80
Asp Glu Gly Ala Pro Gly Lys Gln Ala Ala Ala Gln Pro His Thr Glu
                85                  90                  95
Ile Pro Glu Gly Thr Thr Ala Glu Glu Ala Gly Ile Gly Asp Thr Pro
            100                 105                 110
Ser Leu Glu Asp Glu Ala Ala Gly His Val Thr Gln Ala Arg Met Val
        115                 120                 125
Ser Lys Ser Lys Asp Gly Thr Gly Ser Asp Asp Lys Lys Ala Lys Gly
    130                 135                 140
Ala Asp Gly Lys Thr Lys Ile Ala Thr Pro Arg Gly Ala Ala Pro Pro
145                 150                 155                 160
Gly Gln Lys Gly Gln Ala Asn Ala Thr Arg Ile Pro Ala Lys Thr Pro
                165                 170                 175
Pro Ala Pro Lys Thr Pro Pro Ser Ser Gly Glu Pro Pro Lys Ser Gly
            180                 185                 190
```

Asp Arg Ser Gly Tyr Ser Ser Pro Gly Ser Pro Gly Ser
            195                 200                 205

Arg Ser Arg Thr Pro Ser Leu Pro Thr Pro Thr Arg Glu Pro Lys
    210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
            245                 250                 255

Lys Ser Lys Ile Gly Ser Thr Glu Asn Leu Lys His Gln Pro Gly Gly
            260                 265                 270

Gly Lys Val Gln Ile Val Tyr Lys Pro Val Asp Leu Ser Lys Val Thr
            275                 280                 285

Ser Lys Cys Gly Ser Leu Gly Asn Ile His His Lys Pro Gly Gly Gly
            290                 295                 300

Gln Val Glu Val Lys Ser Glu Lys Leu Asp Phe Lys Asp Arg Val Gln
305                 310                 315                 320

Ser Lys Ile Gly Ser Leu Asp Asn Ile Thr His Val Pro Gly Gly Gly
            325                 330                 335

Asn Lys Lys Ile Glu Thr His Lys Leu Thr Phe Arg Glu Asn Ala Lys
            340                 345                 350

Ala Lys Thr Asp His Gly Ala Glu Ile Val Tyr Lys Ser Pro Val Val
            355                 360                 365

Ser Gly Asp Thr Ser Pro Arg His Leu Ser Asn Val Ser Ser Thr Gly
            370                 375                 380

Ser Ile Asp Met Val Asp Ser Pro Gln Leu Ala Thr Leu Ala Asp Glu
385                 390                 395                 400

Val Ser Ala Ser Leu Ala Lys Gln Gly Leu
            405                 410

<210> SEQ ID NO 9
<211> LENGTH: 16
<212> TYPE: PRT
<213> ORGANISM: Artificial Sequence
<220> FEATURE:
<223> OTHER INFORMATION: ADx210 CDR of the light chain variable region

<400> SEQUENCE: 9

Arg Ser Ser Glu Ser Ile Val His Ser Ser Gly Lys Thr Tyr Leu Glu
1               5                   10                  15

<210> SEQ ID NO 10
<211> LENGTH: 7
<212> TYPE: PRT
<213> ORGANISM: Artificial Sequence
<220> FEATURE:
<223> OTHER INFORMATION: ADx210 CDR of the light chain variable region

<400> SEQUENCE: 10

Glu Val Ser Asn Arg Phe Ser
1               5

<210> SEQ ID NO 11
<211> LENGTH: 9
<212> TYPE: PRT
<213> ORGANISM: Artificial Sequence
<220> FEATURE:
<223> OTHER INFORMATION: ADx210 CDR of the light chain variable region

<400> SEQUENCE: 11

Phe Gln Gly Ser His Val Pro Trp Thr

```
1               5

<210> SEQ ID NO 12
<211> LENGTH: 10
<212> TYPE: PRT
<213> ORGANISM: Artificial Sequence
<220> FEATURE:
<223> OTHER INFORMATION: ADx210 CDR of the heavy chain variable region

<400> SEQUENCE: 12

Gly Phe Thr Phe Ser Asn Phe Gly Met His
1               5                   10

<210> SEQ ID NO 13
<211> LENGTH: 17
<212> TYPE: PRT
<213> ORGANISM: Artificial Sequence
<220> FEATURE:
<223> OTHER INFORMATION: ADx210 CDR of the heavy chain variable region

<400> SEQUENCE: 13

Tyr Ile Thr Ser Gly Ser Ser Ile Tyr Tyr Ala Asp Thr Val Lys
1               5                   10                  15

Gly

<210> SEQ ID NO 14
<211> LENGTH: 11
<212> TYPE: PRT
<213> ORGANISM: Artificial Sequence
<220> FEATURE:
<223> OTHER INFORMATION: ADx210 CDR of the heavy chain variable region

<400> SEQUENCE: 14

Ser Val Pro Tyr Gly Tyr Gly Leu Phe Asp Tyr
1               5                   10

<210> SEQ ID NO 15
<211> LENGTH: 138
<212> TYPE: PRT
<213> ORGANISM: Artificial Sequence
<220> FEATURE:
<223> OTHER INFORMATION: Heavy chain variable region of ADx210

<400> SEQUENCE: 15

Val Gln Leu Gln Glu Ser Gly Gly Gly Leu Val Gln Pro Gly Gly Ser
1               5                   10                  15

Arg Lys Leu Ser Cys Ala Ala Ser Gly Phe Thr Phe Ser Asn Phe Gly
            20                  25                  30

Met His Trp Val Arg Gln Ala Pro Asp Lys Gly Leu Glu Trp Val Ala
        35                  40                  45

Tyr Ile Thr Ser Gly Ser Ser Ile Tyr Tyr Ala Asp Thr Val Lys
    50                  55                  60

Gly Arg Phe Thr Ile Ser Arg Asp Asn Pro Lys Asn Thr Leu Phe Leu
65                  70                  75                  80

Gln Met Thr Ser Leu Arg Ser Glu Asp Thr Ala Met Tyr Tyr Cys Ala
                85                  90                  95

Arg Ser Val Pro Tyr Gly Tyr Gly Leu Phe Asp Tyr Trp Gly Arg Gly
            100                 105                 110

Thr Thr Leu Thr Val Ser Ser Ala Lys Thr Thr Pro Ser Val Tyr
        115                 120                 125

Pro Leu Ala Pro Gly Ser Ala Ala Gln Thr
        130                 135
```

<210> SEQ ID NO 16
<211> LENGTH: 130
<212> TYPE: PRT
<213> ORGANISM: Artificial Sequence
<220> FEATURE:
<223> OTHER INFORMATION: Light chain variable region of ADx210

<400> SEQUENCE: 16

```
Leu Pro Val Arg Leu Val Leu Met Ser Trp Ile Pro Ala Ser Ser
1               5                   10                  15

Ser Asp Val Leu Met Thr Gln Ile Pro Val Ser Leu Ser Val Ser Leu
            20                  25                  30

Gly Asp Gln Ala Ser Ile Ser Cys Arg Ser Ser Glu Ser Ile Val His
            35                  40                  45

Ser Ser Gly Lys Thr Tyr Leu Glu Trp Tyr Leu Gln Lys Pro Gly Gln
        50                  55                  60

Ser Pro Lys Leu Leu Ile Tyr Glu Val Ser Asn Arg Phe Ser Gly Val
65                  70                  75                  80

Pro Asp Arg Phe Ser Gly Ser Gly Ser Gly Thr Asp Phe Thr Leu Lys
                85                  90                  95

Ile Ser Arg Val Glu Ala Glu Asp Leu Gly Val Tyr Tyr Cys Phe Gln
            100                 105                 110

Gly Ser His Val Pro Trp Thr Phe Gly Gly Gly Thr Lys Leu Glu Ile
            115                 120                 125

Lys Arg
    130
```

<210> SEQ ID NO 17
<211> LENGTH: 132
<212> TYPE: PRT
<213> ORGANISM: Artificial Sequence
<220> FEATURE:
<223> OTHER INFORMATION: subpart of the Heavy chain variable region of
      ADx210

<400> SEQUENCE: 17

```
Val Gln Leu Gln Glu Ser Gly Gly Gly Leu Val Gln Pro Gly Gly Ser
1               5                   10                  15

Arg Lys Leu Ser Cys Ala Ala Ser Gly Phe Thr Phe Ser Asn Phe Gly
            20                  25                  30

Met His Trp Val Arg Gln Ala Pro Asp Lys Gly Leu Glu Trp Val Ala
            35                  40                  45

Tyr Ile Thr Ser Gly Ser Ser Ile Tyr Tyr Ala Asp Thr Val Lys
        50                  55                  60

Gly Arg Phe Thr Ile Ser Arg Asp Asn Pro Lys Asn Thr Leu Phe Leu
65                  70                  75                  80

Gln Met Thr Ser Leu Arg Ser Glu Asp Thr Ala Met Tyr Tyr Cys Ala
                85                  90                  95

Arg Ser Val Pro Tyr Gly Tyr Gly Leu Phe Asp Tyr Trp Gly Arg Gly
            100                 105                 110

Thr Thr Leu Thr Val Ser Ser Ala Lys Thr Thr Pro Pro Ser Val Tyr
            115                 120                 125

Pro Leu Ala Pro
    130
```

<210> SEQ ID NO 18
<211> LENGTH: 131

<212> TYPE: PRT
<213> ORGANISM: Artificial Sequence
<220> FEATURE:
<223> OTHER INFORMATION: Light chain variable region of an isoform of
      ADx210

<400> SEQUENCE: 18

Lys Leu Pro Val Arg Leu Leu Val Leu Met Ser Trp Ile Pro Ala Ser
1               5                   10                  15

Ser Ser Asp Val Leu Met Thr Gln Ile Pro Val Ser Leu Ser Val Ser
            20                  25                  30

Leu Gly Asp Gln Ala Ser Ile Ser Cys Arg Ser Ser Glu Ser Ile Val
        35                  40                  45

His Ser Ser Gly Lys Thr Tyr Leu Glu Trp Tyr Leu Gln Lys Pro Gly
    50                  55                  60

Gln Ser Pro Lys Leu Leu Ile Tyr Glu Val Ser Asn Arg Phe Ser Gly
65                  70                  75                  80

Val Pro Asp Arg Phe Ser Gly Ser Gly Ser Gly Thr Asp Phe Thr Leu
                85                  90                  95

Lys Ile Ser Arg Val Glu Ala Glu Asp Leu Gly Val Tyr Tyr Cys Phe
            100                 105                 110

Gln Gly Ser His Val Pro Trp Thr Phe Gly Gly Gly Thr Lys Leu Glu
        115                 120                 125

Ile Lys Arg
    130

<210> SEQ ID NO 19
<211> LENGTH: 10
<212> TYPE: PRT
<213> ORGANISM: Artificial Sequence
<220> FEATURE:
<223> OTHER INFORMATION: ADx215 CDR of the heavy chain variable region

<400> SEQUENCE: 19

Gly Phe Asn Phe Arg Ser Tyr Gly Met Ser
1               5                   10

<210> SEQ ID NO 20
<211> LENGTH: 17
<212> TYPE: PRT
<213> ORGANISM: Artificial Sequence
<220> FEATURE:
<223> OTHER INFORMATION: ADx215 CDR of the heavy chain variable region

<400> SEQUENCE: 20

Thr Ile Ser Ser Gly Gly Asn Tyr Thr Tyr Tyr Pro Asp Ser Val Lys
1               5                   10                  15

Gly

<210> SEQ ID NO 21
<211> LENGTH: 8
<212> TYPE: PRT
<213> ORGANISM: Artificial Sequence
<220> FEATURE:
<223> OTHER INFORMATION: ADx215 CDR of the heavy chain variable region

<400> SEQUENCE: 21

Ser Phe Tyr Gly Ala Phe Asp Tyr
1               5

<210> SEQ ID NO 22
<211> LENGTH: 16

```
<212> TYPE: PRT
<213> ORGANISM: Artificial Sequence
<220> FEATURE:
<223> OTHER INFORMATION: ADx215 CDR of the light chain variable region

<400> SEQUENCE: 22

Arg Ser Ser Gln Asn Ile Leu His Ser Asn Gly Asn Thr Tyr Leu Glu
1               5                   10                  15

<210> SEQ ID NO 23
<211> LENGTH: 7
<212> TYPE: PRT
<213> ORGANISM: Artificial Sequence
<220> FEATURE:
<223> OTHER INFORMATION: ADx215 CDR of the light chain variable region

<400> SEQUENCE: 23

Lys Val Ser Ser Arg Phe Ser
1               5

<210> SEQ ID NO 24
<211> LENGTH: 9
<212> TYPE: PRT
<213> ORGANISM: Artificial Sequence
<220> FEATURE:
<223> OTHER INFORMATION: ADx215 CDR of the light chain variable region

<400> SEQUENCE: 24

Phe Gln Gly Ser Leu Val Pro Trp Thr
1               5

<210> SEQ ID NO 25
<211> LENGTH: 182
<212> TYPE: PRT
<213> ORGANISM: Artificial Sequence
<220> FEATURE:
<223> OTHER INFORMATION: ADx215 Heavy chain variable region

<400> SEQUENCE: 25

Asp Phe Gly Leu Ser Trp Val Phe Leu Ala Leu Ile Leu Lys Gly Ile
1               5                   10                  15

Gln Cys Glu Val Gln Leu Val Glu Ser Gly Gly Asp Leu Val Lys Pro
            20                  25                  30

Gly Gly Ser Leu Lys Leu Ser Cys Ala Ala Ser Gly Phe Asn Phe Arg
        35                  40                  45

Ser Tyr Gly Met Ser Trp Val Arg Gln Thr Pro Asp Lys Arg Leu Glu
    50                  55                  60

Trp Val Ala Thr Ile Ser Ser Gly Gly Asn Tyr Thr Tyr Tyr Pro Asp
65                  70                  75                  80

Ser Val Lys Gly Arg Phe Thr Ile Ser Arg Asp Asn Ala Lys Asn Ile
                85                  90                  95

Leu Tyr Leu Gln Met Ser Ser Leu Asn Ser Glu Asp Thr Ala Leu Tyr
            100                 105                 110

Tyr Cys Thr Tyr Ser Phe Tyr Gly Ala Phe Asp Tyr Trp Gly Gln Gly
        115                 120                 125

Thr Thr Leu Thr Val Ser Ser Ala Lys Thr Thr Pro Pro Ser Val Tyr
    130                 135                 140

Pro Leu Ala Pro Gly Ser Ala Ala Gln Thr Asn Ser Met Val Thr Leu
145                 150                 155                 160

Gly Cys Leu Val Lys Gly Tyr Phe Pro Glu Pro Val Thr Val Thr Trp
                165                 170                 175
```

Asn Ser Gly Ser Leu Ser
            180

<210> SEQ ID NO 26
<211> LENGTH: 148
<212> TYPE: PRT
<213> ORGANISM: Artificial Sequence
<220> FEATURE:
<223> OTHER INFORMATION: ADx215 Light chain variable region

<400> SEQUENCE: 26

Lys Leu Pro Val Arg Leu Leu Val Leu Met Phe Trp Ile Pro Ala Ser
1               5                   10                  15

Ser Ser Asp Val Leu Met Thr Gln Thr Pro Leu Ser Leu Pro Val Ser
            20                  25                  30

Leu Gly Asp Gln Ala Ser Ile Ser Cys Arg Ser Ser Gln Asn Ile Leu
        35                  40                  45

His Ser Asn Gly Asn Thr Tyr Leu Glu Trp Tyr Leu Gln Lys Pro Gly
    50                  55                  60

Gln Ser Pro Lys Leu Leu Ile Tyr Lys Val Ser Ser Arg Phe Ser Gly
65                  70                  75                  80

Val Pro Asp Arg Phe Ser Gly Ser Gly Ser Gly Thr Asp Phe Thr Leu
                85                  90                  95

Lys Ile Thr Arg Val Glu Ala Glu Asp Leu Gly Val Tyr Tyr Cys Phe
            100                 105                 110

Gln Gly Ser Leu Val Pro Trp Thr Phe Gly Gly Gly Thr Lys Leu Glu
        115                 120                 125

Ile Arg Arg Ala Asp Ala Ala Pro Thr Val Ser Ile Phe Pro Pro Ser
    130                 135                 140

Ser Glu Gln Leu
145

<210> SEQ ID NO 27
<211> LENGTH: 9
<212> TYPE: PRT
<213> ORGANISM: Artificial Sequence
<220> FEATURE:
<223> OTHER INFORMATION: Tau epitope recognized by ADx215

<400> SEQUENCE: 27

Gly Thr Tyr Gly Leu Gly Asp Arg Lys
1               5

<210> SEQ ID NO 28
<211> LENGTH: 9
<212> TYPE: PRT
<213> ORGANISM: Artificial Sequence
<220> FEATURE:
<223> OTHER INFORMATION: Tau epitope recognized by ADx215

<400> SEQUENCE: 28

Glu Phe Glu Val Met Glu Asp His Ala
1               5

<210> SEQ ID NO 29
<211> LENGTH: 18
<212> TYPE: PRT
<213> ORGANISM: Artificial Sequence
<220> FEATURE:
<223> OTHER INFORMATION: Tau epitope recognized by ADx215

<400> SEQUENCE: 29

```
Glu Phe Glu Val Met Glu Asp His Ala Gly Thr Tyr Gly Leu Gly Asp
1               5                   10                  15

Arg Lys
```

<210> SEQ ID NO 30
<211> LENGTH: 7
<212> TYPE: PRT
<213> ORGANISM: Artificial Sequence
<220> FEATURE:
<223> OTHER INFORMATION: Tau epitope recognized by ADx201

<400> SEQUENCE: 30

```
Pro Pro Thr Arg Glu Pro Lys
1               5
```

<210> SEQ ID NO 31
<211> LENGTH: 15
<212> TYPE: PRT
<213> ORGANISM: Artificial Sequence
<220> FEATURE:
<223> OTHER INFORMATION: Tau epitope

<400> SEQUENCE: 31

```
Met Ala Glu Pro Arg Gln Glu Phe Glu Val Met Glu Asp His Ala
1               5                   10                  15
```

<210> SEQ ID NO 32
<211> LENGTH: 15
<212> TYPE: PRT
<213> ORGANISM: Artificial Sequence
<220> FEATURE:
<223> OTHER INFORMATION: Tau epitope

<400> SEQUENCE: 32

```
Ala Glu Pro Arg Gln Glu Phe Glu Val Met Glu Asp His Ala Gly
1               5                   10                  15
```

<210> SEQ ID NO 33
<211> LENGTH: 15
<212> TYPE: PRT
<213> ORGANISM: Artificial Sequence
<220> FEATURE:
<223> OTHER INFORMATION: Tau epitope

<400> SEQUENCE: 33

```
Glu Pro Arg Gln Glu Phe Glu Val Met Glu Asp His Ala Gly Thr
1               5                   10                  15
```

<210> SEQ ID NO 34
<211> LENGTH: 15
<212> TYPE: PRT
<213> ORGANISM: Artificial Sequence
<220> FEATURE:
<223> OTHER INFORMATION: Tau epitope

<400> SEQUENCE: 34

```
Pro Arg Gln Glu Phe Glu Val Met Glu Asp His Ala Gly Thr Tyr
1               5                   10                  15
```

<210> SEQ ID NO 35
<211> LENGTH: 15
<212> TYPE: PRT
<213> ORGANISM: Artificial Sequence
<220> FEATURE:
<223> OTHER INFORMATION: Tau epitope

<400> SEQUENCE: 35

```
Arg Gln Glu Phe Glu Val Met Glu Asp His Ala Gly Thr Tyr Gly
 1               5                  10                  15

<210> SEQ ID NO 36
<211> LENGTH: 15
<212> TYPE: PRT
<213> ORGANISM: Artificial Sequence
<220> FEATURE:
<223> OTHER INFORMATION: Tau epitope

<400> SEQUENCE: 36

Gln Glu Phe Glu Val Met Glu Asp His Ala Gly Thr Tyr Gly Leu
 1               5                  10                  15

<210> SEQ ID NO 37
<211> LENGTH: 15
<212> TYPE: PRT
<213> ORGANISM: Artificial Sequence
<220> FEATURE:
<223> OTHER INFORMATION: Tau epitope

<400> SEQUENCE: 37

Glu Phe Glu Val Met Glu Asp His Ala Gly Thr Tyr Gly Leu Gly
 1               5                  10                  15

<210> SEQ ID NO 38
<211> LENGTH: 15
<212> TYPE: PRT
<213> ORGANISM: Artificial Sequence
<220> FEATURE:
<223> OTHER INFORMATION: Tau epitope

<400> SEQUENCE: 38

Phe Glu Val Met Glu Asp His Ala Gly Thr Tyr Gly Leu Gly Asp
 1               5                  10                  15

<210> SEQ ID NO 39
<211> LENGTH: 15
<212> TYPE: PRT
<213> ORGANISM: Artificial Sequence
<220> FEATURE:
<223> OTHER INFORMATION: Tau epitope

<400> SEQUENCE: 39

Glu Val Met Glu Asp His Ala Gly Thr Tyr Gly Leu Gly Asp Arg
 1               5                  10                  15

<210> SEQ ID NO 40
<211> LENGTH: 15
<212> TYPE: PRT
<213> ORGANISM: Artificial Sequence
<220> FEATURE:
<223> OTHER INFORMATION: Tau epitope

<400> SEQUENCE: 40

Val Met Glu Asp His Ala Gly Thr Tyr Gly Leu Gly Asp Arg Lys
 1               5                  10                  15

<210> SEQ ID NO 41
<211> LENGTH: 15
<212> TYPE: PRT
<213> ORGANISM: Artificial Sequence
<220> FEATURE:
<223> OTHER INFORMATION: Tau epitope

<400> SEQUENCE: 41
```

```
Met Glu Asp His Ala Gly Thr Tyr Gly Leu Gly Asp Arg Lys Asp
1               5                   10                  15
```

<210> SEQ ID NO 42
<211> LENGTH: 15
<212> TYPE: PRT
<213> ORGANISM: Artificial Sequence
<220> FEATURE:
<223> OTHER INFORMATION: Tau epitope

<400> SEQUENCE: 42

```
Glu Asp His Ala Gly Thr Tyr Gly Leu Gly Asp Arg Lys Asp Gln
1               5                   10                  15
```

<210> SEQ ID NO 43
<211> LENGTH: 15
<212> TYPE: PRT
<213> ORGANISM: Artificial Sequence
<220> FEATURE:
<223> OTHER INFORMATION: Tau epitope

<400> SEQUENCE: 43

```
Asp His Ala Gly Thr Tyr Gly Leu Gly Asp Arg Lys Asp Gln Gly
1               5                   10                  15
```

<210> SEQ ID NO 44
<211> LENGTH: 15
<212> TYPE: PRT
<213> ORGANISM: Artificial Sequence
<220> FEATURE:
<223> OTHER INFORMATION: Tau epitope

<400> SEQUENCE: 44

```
His Ala Gly Thr Tyr Gly Leu Gly Asp Arg Lys Asp Gln Gly Gly
1               5                   10                  15
```

<210> SEQ ID NO 45
<211> LENGTH: 15
<212> TYPE: PRT
<213> ORGANISM: Artificial Sequence
<220> FEATURE:
<223> OTHER INFORMATION: Tau epitope

<400> SEQUENCE: 45

```
Ala Gly Thr Tyr Gly Leu Gly Asp Arg Lys Asp Gln Gly Gly Tyr
1               5                   10                  15
```

<210> SEQ ID NO 46
<211> LENGTH: 15
<212> TYPE: PRT
<213> ORGANISM: Artificial Sequence
<220> FEATURE:
<223> OTHER INFORMATION: Tau epitope

<400> SEQUENCE: 46

```
Gly Thr Tyr Gly Leu Gly Asp Arg Lys Asp Gln Gly Gly Tyr Thr
1               5                   10                  15
```

<210> SEQ ID NO 47
<211> LENGTH: 15
<212> TYPE: PRT
<213> ORGANISM: Artificial Sequence
<220> FEATURE:
<223> OTHER INFORMATION: Tau epitope

<400> SEQUENCE: 47

```
Thr Tyr Gly Leu Gly Asp Arg Lys Asp Gln Gly Gly Tyr Thr Met
```

```
<210> SEQ ID NO 48
<211> LENGTH: 15
<212> TYPE: PRT
<213> ORGANISM: Artificial Sequence
<220> FEATURE:
<223> OTHER INFORMATION: Tau epitope

<400> SEQUENCE: 48

Tyr Gly Leu Gly Asp Arg Lys Asp Gln Gly Gly Tyr Thr Met His
1               5                   10                  15

<210> SEQ ID NO 49
<211> LENGTH: 15
<212> TYPE: PRT
<213> ORGANISM: Artificial Sequence
<220> FEATURE:
<223> OTHER INFORMATION: Tau epitope

<400> SEQUENCE: 49

Gly Leu Gly Asp Arg Lys Asp Gln Gly Gly Tyr Thr Met His Gln
1               5                   10                  15

<210> SEQ ID NO 50
<211> LENGTH: 15
<212> TYPE: PRT
<213> ORGANISM: Artificial Sequence
<220> FEATURE:
<223> OTHER INFORMATION: Tau epitope

<400> SEQUENCE: 50

Leu Gly Asp Arg Lys Asp Gln Gly Gly Tyr Thr Met His Gln Asp
1               5                   10                  15

<210> SEQ ID NO 51
<211> LENGTH: 15
<212> TYPE: PRT
<213> ORGANISM: Artificial Sequence
<220> FEATURE:
<223> OTHER INFORMATION: Tau epitope

<400> SEQUENCE: 51

Gly Asp Arg Lys Asp Gln Gly Gly Tyr Thr Met His Gln Asp Gln
1               5                   10                  15

<210> SEQ ID NO 52
<211> LENGTH: 4
<212> TYPE: PRT
<213> ORGANISM: Artificial Sequence
<220> FEATURE:
<223> OTHER INFORMATION: RGD peptide

<400> SEQUENCE: 52

Arg Gly Asp Ser
1

<210> SEQ ID NO 53
<211> LENGTH: 10
<212> TYPE: PRT
```

```
<213> ORGANISM: Artificial Sequence
<220> FEATURE:
<223> OTHER INFORMATION: RGD peptide

<400> SEQUENCE: 53

Arg Gly Asp Ser Pro Ala Ser Ser Lys Pro
1               5                   10
```